US012692514B2

(12) United States Patent
Mitragotri et al.

(10) Patent No.: US 12,692,514 B2
(45) Date of Patent: Jul. 28, 2026

(54) LIVING CELLS ENGINEERED WITH POLYPHENOL-FUNCTIONALIZED BIOLOGICALLY ACTIVE NANOCOMPLEXES

(71) Applicant: PRESIDENT AND FELLOWS OF HARVARD COLLEGE, Cambridge, MA (US)

(72) Inventors: Samir Mitragotri, Lexington, MA (US); Zongmin Zhao, Cambridge, MA (US); Junling Guo, Cambridge, MA (US)

(73) Assignee: PRESIDENT AND FELLOWS OF HARVARD COLLEGE

( * ) Notice: Subject to any disclaimer, the term of this patent is extended or adjusted under 35 U.S.C. 154(b) by 747 days.

(21) Appl. No.: 17/998,945

(22) PCT Filed: May 26, 2021

(86) PCT No.: PCT/US2021/034132
§ 371 (c)(1),
(2) Date: Nov. 16, 2022

(87) PCT Pub. No.: WO2021/242794
PCT Pub. Date: Dec. 2, 2021

(65) Prior Publication Data
US 2023/0173095 A1      Jun. 8, 2023

Related U.S. Application Data

(60) Provisional application No. 63/031,614, filed on May 29, 2020.

(51) Int. Cl.
| | |
|---|---|
| A61K 47/69 | (2017.01) |
| A61K 35/18 | (2015.01) |
| A61K 39/00 | (2006.01) |
| A61K 40/10 | (2025.01) |
| A61K 40/42 | (2025.01) |
| A61K 47/68 | (2017.01) |
| A61K 48/00 | (2006.01) |
| C12N 15/86 | (2006.01) |

(52) U.S. Cl.
CPC .............. *C12N 15/86* (2013.01); *A61K 35/18* (2013.01); *A61K 39/0011* (2013.01); *A61K 40/10* (2025.01); *A61K 40/42* (2025.01); *A61K 47/6849* (2017.08); *A61K 47/6901* (2017.08); *A61K 48/0033* (2013.01); *A61K 2239/31* (2023.05); *C12N 2750/14143* (2013.01); *C12N 2750/14171* (2013.01)

(58) Field of Classification Search
CPC ............................ A61K 47/6941; A61K 35/18
See application file for complete search history.

(56) References Cited

U.S. PATENT DOCUMENTS

| | | | |
|---|---|---|---|
| 6,355,270 B1 | 3/2002 | Ferrari et al. | |
| 6,998,393 B2 | 2/2006 | Jin et al. | |
| 2009/0258057 A1 | 10/2009 | Swiston et al. | |
| 2011/0038939 A1 | 2/2011 | Lvov et al. | |
| 2012/0195939 A1 | 8/2012 | Nadal-Ginard | |
| 2013/0045162 A1 | 2/2013 | Lillard et al. | |
| 2015/0010630 A1 | 1/2015 | Llamas et al. | |
| 2016/0331802 A1 | 11/2016 | Li et al. | |
| 2017/0266317 A1 | 9/2017 | Polak et al. | |
| 2018/0243440 A1 | 8/2018 | Muzykantov et al. | |
| 2020/0376137 A1 | 12/2020 | Mitragotri et al. | |
| 2022/0323603 A1* | 10/2022 | Mitragotri .............. | A61K 35/18 |

FOREIGN PATENT DOCUMENTS

| | | | |
|---|---|---|---|
| WO | 2004032970 A1 | 4/2004 | |
| WO | 2009134866 A2 | 11/2009 | |
| WO | 2019139892 A1 | 7/2019 | |

OTHER PUBLICATIONS

Chen et al. (RSC Adv. Mar. 10, 2022;12(13):7689-7711).*
Han et al. (Angew. Chem. Int. Ed. 59, Mar. 20, 2020).*
Ma "Establishment and in vitro evaluation of CPT-11-PLGA nanoparticle erythrocyte system", pp. 15-25, Published date: Mar. 15, 2017 [English Translation Provided].
Pan et al. "Nanoparticle properties modulate their attachment and effect on carrier red blood cells." Scientific Reports 8.1: 1615 (2018).
Chambers et al. "Long Circulating Nanoparticles via Adhesion on Red Blood Cells: Mechanism and Extended Circulation" Experimental Biology and Medicine 232:958-966 (2007).
Ma Yu. "Establishment and in vitro evaluation of CPT-11-PLGA nanoparticle erythrocyte system", Master's Degree Thesis from Southeast University, Published Mar. 15, 2017.
Brenner et al., "Red blood cel-hitchhiking boosts delivery of nanocarriers to chosen organs by orders of magnitude." Nature Communications 9(1): Dec. 1, 2018.
Han et al., "Polyphenol-Medicated Assembly of Proteins for Engineering Functional Materials." Angewandte Chemie International Edition 59(36): 15618-15625 (Mar. 20, 2020).
Shin et al., "Targeting protein and peptide therapeutics to the heart via tannic acid modification." Nature Biomedical Engineering 2(5) 304-317 (Apr. 30, 2018).
Zhao et al., "Engineering of Living Cells with Polyphenol-Functionalized Biologically Active Nanocomplexes." Advanced Materials 32(49): 2003492 (Nov. 4, 2020).
Chu et al. "Photosensitization Priming of Tumor Microenvironments Improves Delivery of Nanotherapeutics via Neutrophil Infiltration" Advanced Materials 29:1701021 (2017).

(Continued)

*Primary Examiner* — Gary B Nickol
(74) *Attorney, Agent, or Firm* — NIXON PEABODY LLP; David S. Resnick; Nicole D. Kling

(57) ABSTRACT

Described herein are functionalizing nanocomplexes comprising one or more polyphenol molecules; and one or more biomolecules. Further described herein are functionalized cells comprising one or more of the nanocomplexes. In some embodiments, the biomolecules can be therapeutic agents and the functionalized cells can be administered to patients to provide improved delivery (e.g., dosing and specificity) of the therapeutic agent.

14 Claims, 37 Drawing Sheets

(56)                    References Cited

OTHER PUBLICATIONS

Fahmy et al. "Nanosystems for Simultaneous Imaging and Drug Delivery to T Cells" The AAPS Journal 9:19 (2007).

Park et al. "Hyaluronic acid-coated nanparticles for targeted photodynamic theapy of cancer guided by near-infrared and MR imaging." Carbohydrate Polymers 157:476-483 (2016).

Shields et al. "Cellular backpacks for macrophage immunotherapy." Sci Adv 6:1-12 (2020).

Steenblock et al. "An Artificial Antigen-presenting Cell with Pracrine Delivery of IL-2 Impacts the Magnitude and Direction of the T Cell Reponse." TBC 40:34883-34592 (2011).

Tang et al. "Enhancing T cell therapy through TCR signaling-responsive nanoparticle drug delivery" Nat Biotechnol 36:707-716 (2018).

Warren et al. "A novel binding assy to assess specificity of monoclonal antibodies." J Immunol Methods 305:33-38 (2005).

Zhang et al. "Hyaluronic Acid-Chitosan Nanoparticles to Deliver Gd-DTPA for MR Cancer Imaging." Nanomaterials 5:1379-1396 (2015).

Steenblock et al. "A Comprehensive Platform for Ex Vivo T-cell Expansion Based on Biodegradable Polymeric Artificial Antigen-presenting Cells." Molecular Therapy 16(4):765-772 (2008).

Anselmo et al., "Delivering Nanoparticles to Lungs while Avoiding Liver and Spleen through Adsorption on Red Blood Cells" ACS NANO 7(12):11129-11137 (2013).

Pang et al., "Primary M1 macrophages as multifunctional carrier combined with PLGA nanoparticle delivering anticancer drug for efficient glioma therapy." Drug Delivery 25(1):1922-1931 (2018).

Rezvantalab et al., "PLGA-Based Nanoparticles in Cancer Treatment" Frontiers in Pharmacology 9:1663-9812 (2018).

Zelepukin et al., "Nanoparticle-based drug delivery via RBC-hitchhiking for the inhibition of lung metastases growth." Nanoscale 11(4):1636-1646 (2019).

Anselmo et al., "Cell-mediated delivery of nanoparticles: taking advantage of circulatory cells to target nanoparticles." Journal of Controlled Release 190:531-541 (2014).

Anselmo et al., "Monocyte-mediated delivery of polymeric backpacks to inflamed tissues: a generalized strategy to deliver drugs to treat inflammation." Journal of Controlled Release 199:29-36 (2015).

Ayer et al., "Cell-mediated delivery of synthetic nano-and microparticles." Journal of Controlled Release 259:92-104 (2017).

Guo et al. "Light-driven fine chemical production in yeast biohybrids." Science 362(6416): 813-816 (2018).

Guo et al. "Modular assembly of superstructures from polyphenol-functionalized building blocks." Nature Nanotechnology 11(12): 1105-1111 (2016).

Lv et al. "Polymers for cytosolic protein delivery." Biomaterials 218: 119358 (2019).

Quan et al. "Protein-polyphenol conjugates: Antioxidant property, functionalities and their applications." Trends in Food Science & Technology 91: 507-517 (2019).

Reitzer et al. "Polyphenols at interfaces." Advances in Colloid and Interface Science 257: 31-41 (2018).

Shields et al. "Induction of lymphoidlike stroma and immune escape by tumors that express the chemokine CCL21." Science 328.5979 (2010): 749-752.

Villa et al., "Red blood cells: supercarriers for drugs, biologicals, and nanoparticles and inspiration for advanced delivery systems." Advanced Drug Delivery Reviews 106:88-103 (2016).

Von Staszewski et al. "Nanocomplex formation between β-lactoglobulin or caseinomacropeptide and green tea polyphenols: Impact on protein gelation and polyphenols antiproliferative activity." Journal of Functional Foods 4(4): 800-809 (2012).

Xu et al. "Natural polyphenols as versatile platforms for material engineering and surface functionalization." Progress in Polymer Science 87: 165-196 (2018).

Kapoor et al. "PLGA: a unique polymer for drug delivery." Therapeutic delivery 6.1: 41-58 (2015).

Luk et al. "Safe and immunocompatible nanocarriers cloaked in RBC membranes for drug delivery to treat solid tumors." Theranostics 6.7: 1004-1011 (2016).

Apte et al. "VEGF in Singally and Disease: Beyond Discovery and Development." Cell 176:1248-1264 (Mar. 7, 2019).

* cited by examiner

ERYTHROCYTE SEM

ASSEMBLY OF NANOCOMPLEXES

TO *FIG. 1E*

FROM *FIG. 1D*

ERYTHROCYTE$_{WP}$

TOP VIEW

→ TO *FIG. 1F*

CONCAVE

Erythrocyte only
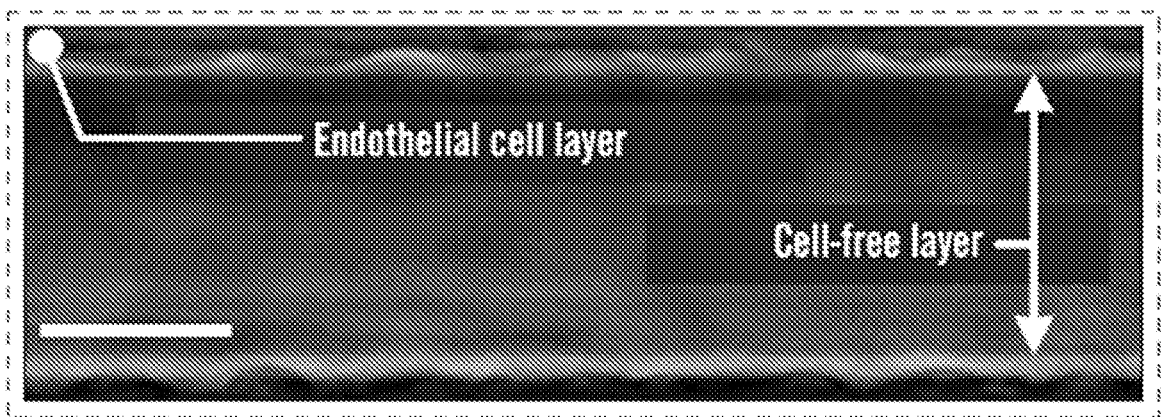
Erythrocyte$_{WP}$
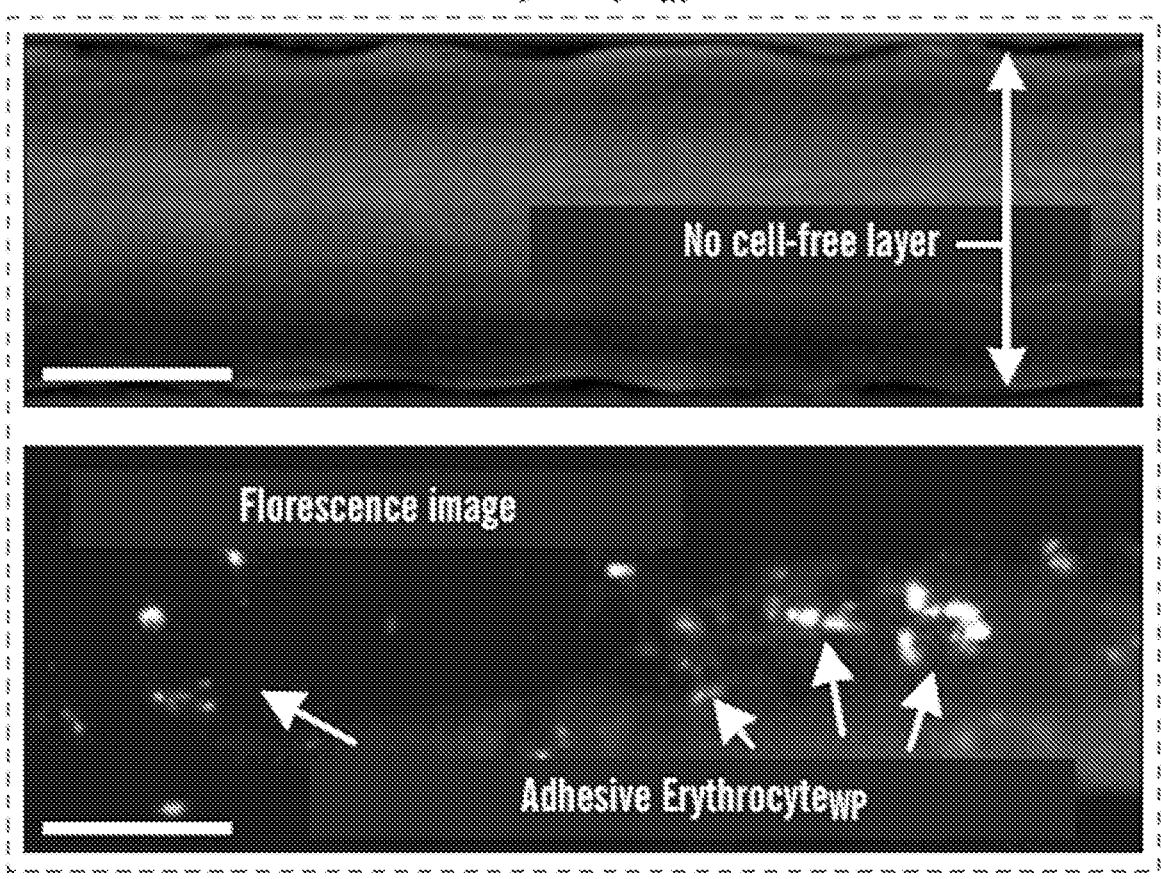
*FIG. 3H*

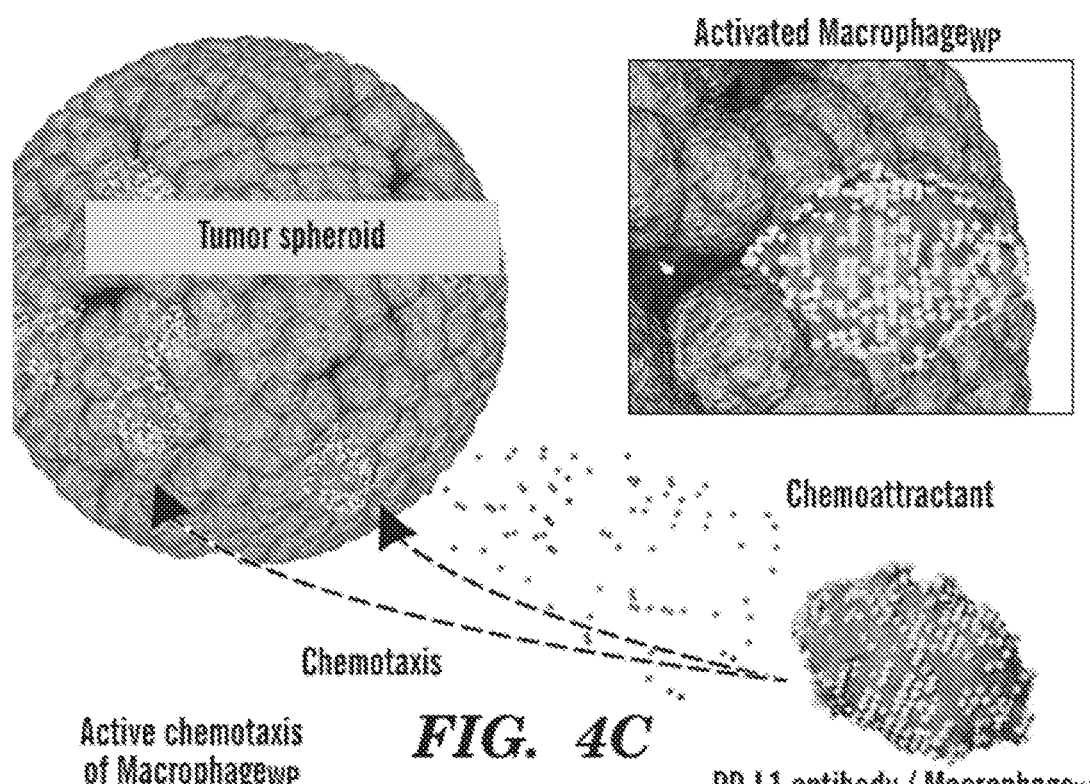
*FIG. 4C*
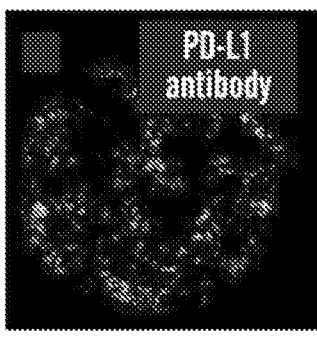
*FIG. 4D*
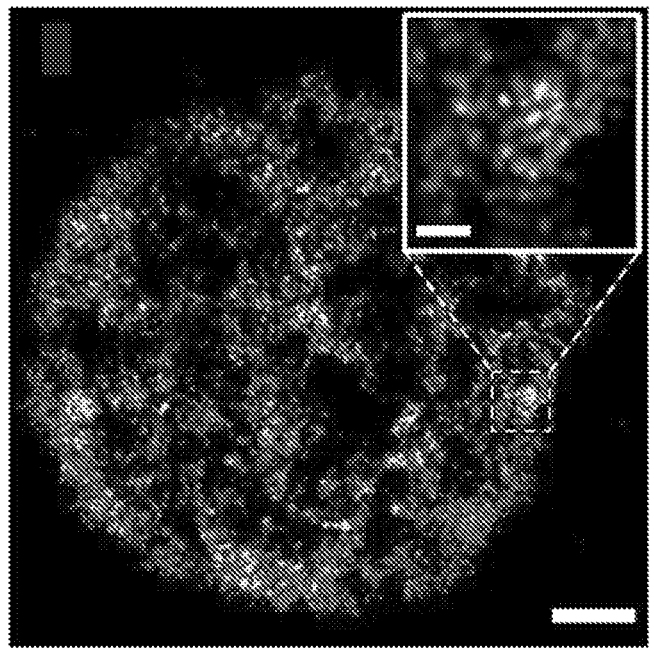
*FIG. 4E*
*FIG. 4F*

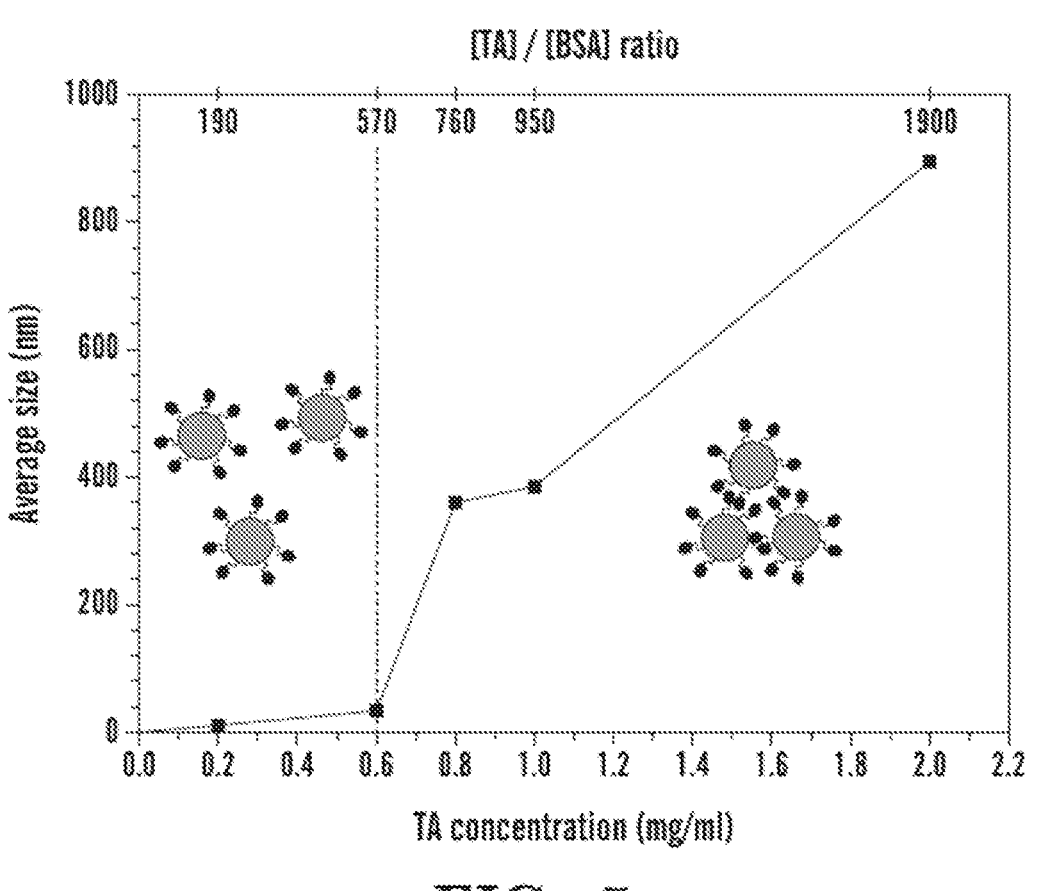
*FIG. 5*
Protein nanocomplexes
mRNA nanocomplexes
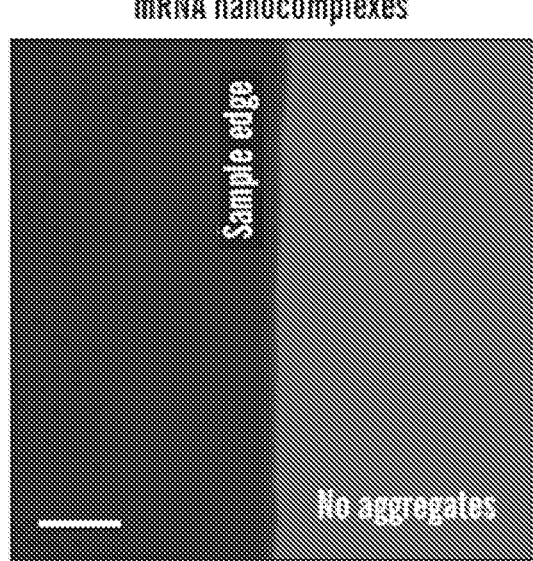
*FIG. 6A*          *FIG. 6B*

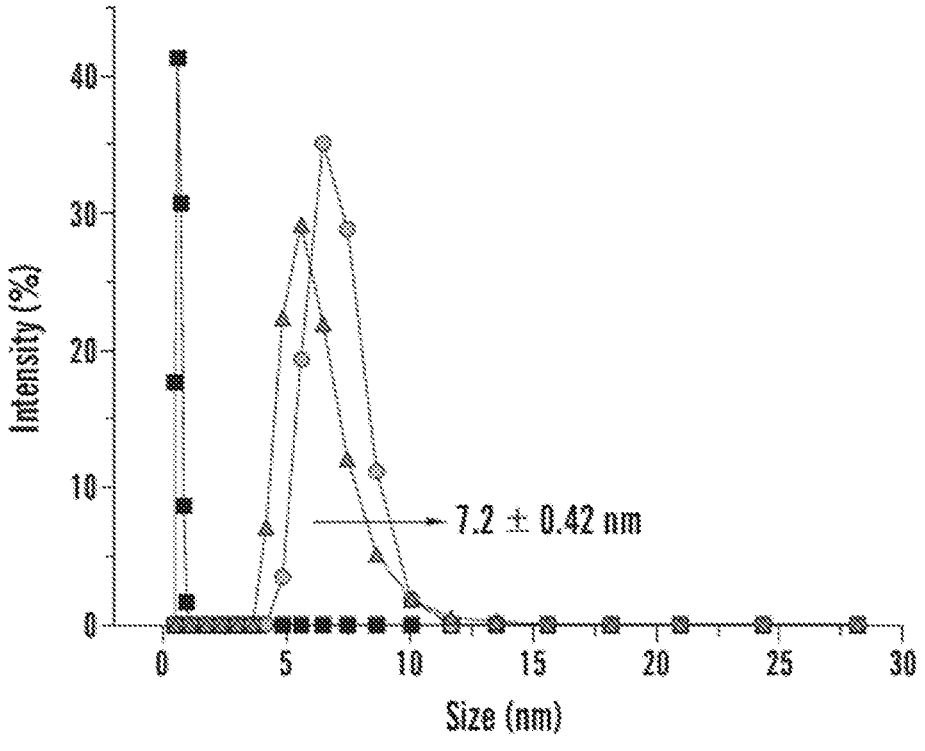
*FIG. 7*
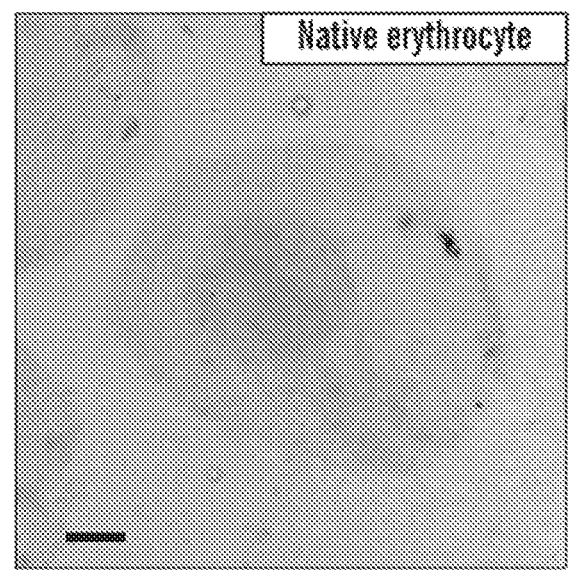
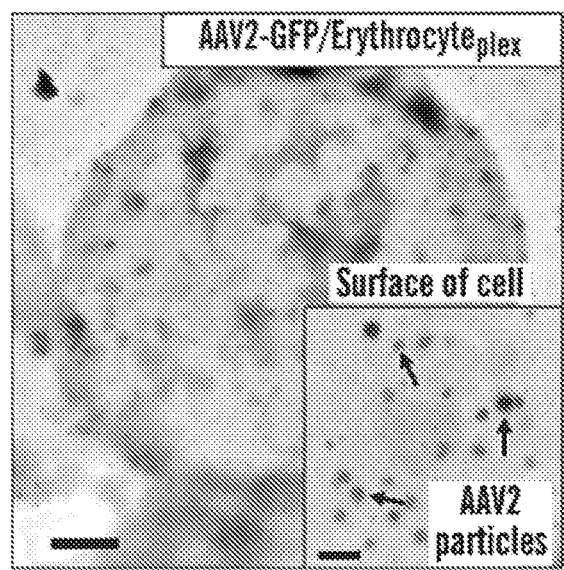
*FIG. 8A*    *FIG. 8B*

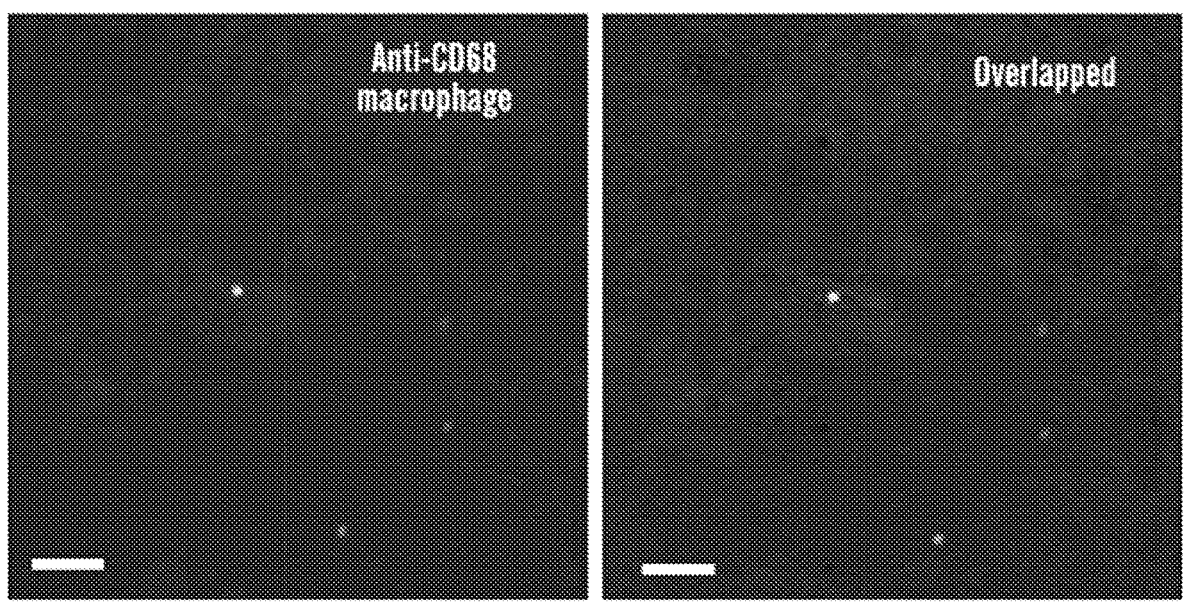
*FIG. 13A*        *FIG. 13B*
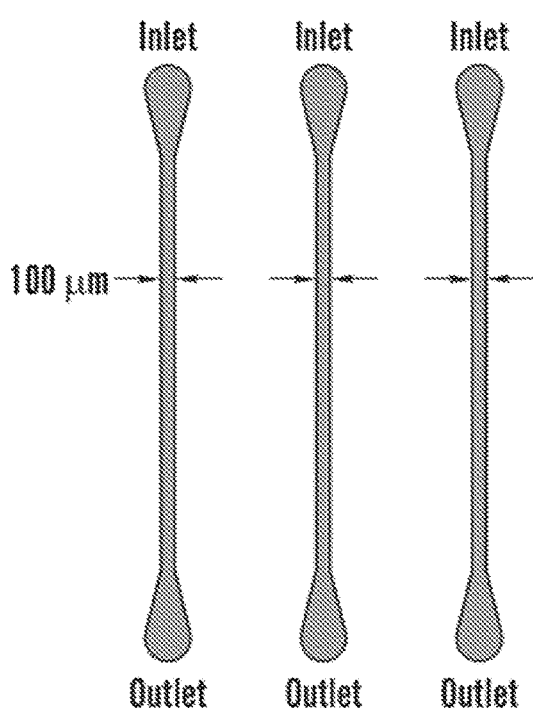
*FIG. 14*

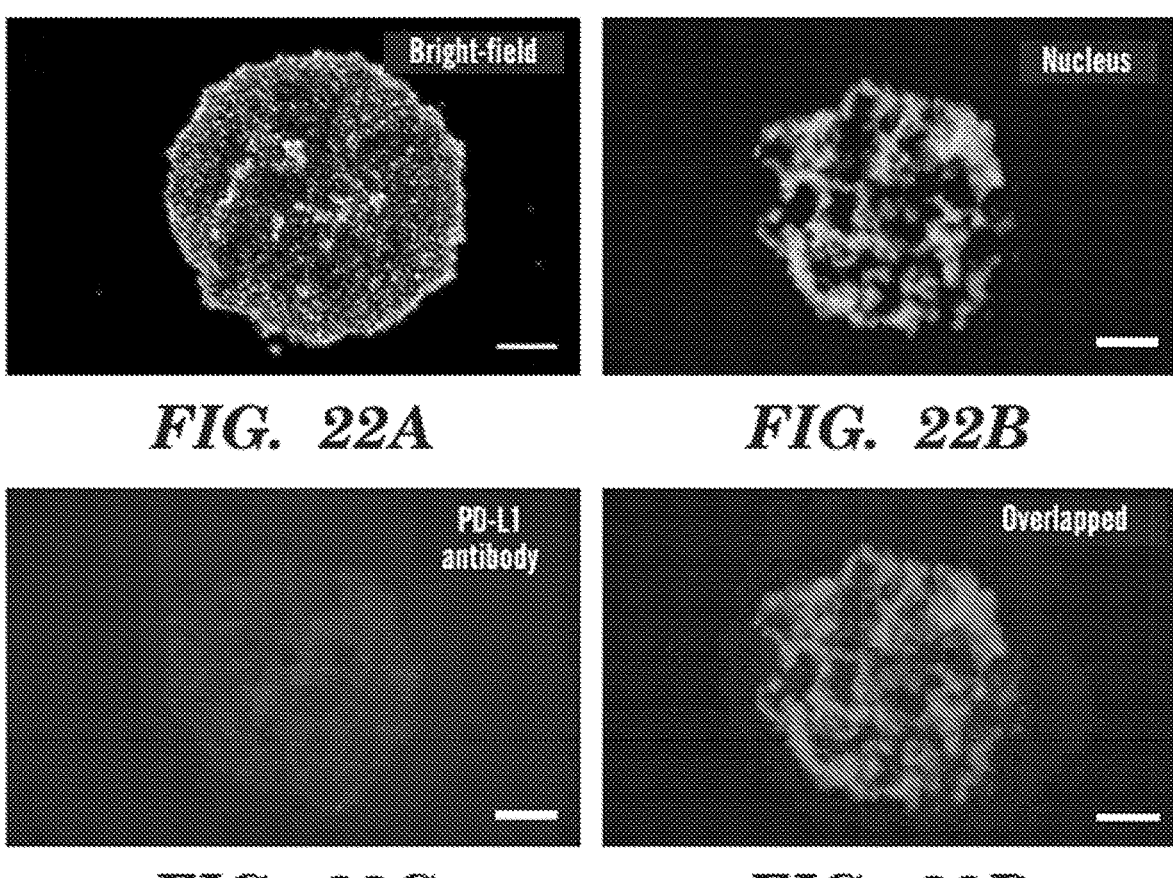
*FIG. 22A*          *FIG. 22B*
*FIG. 22C*          *FIG. 22D*
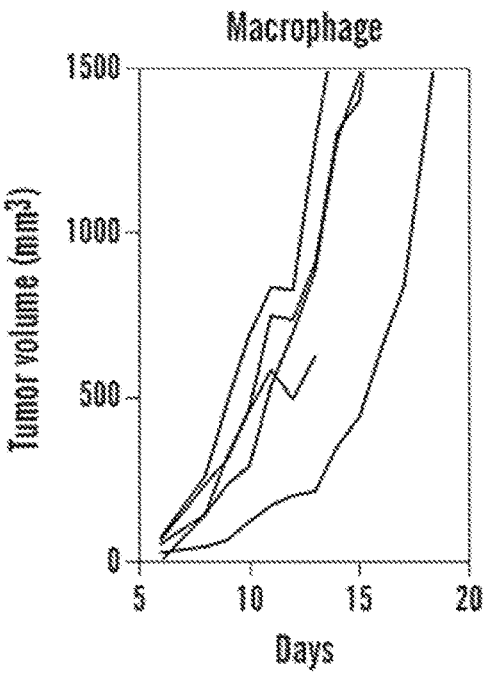
*FIG. 23*

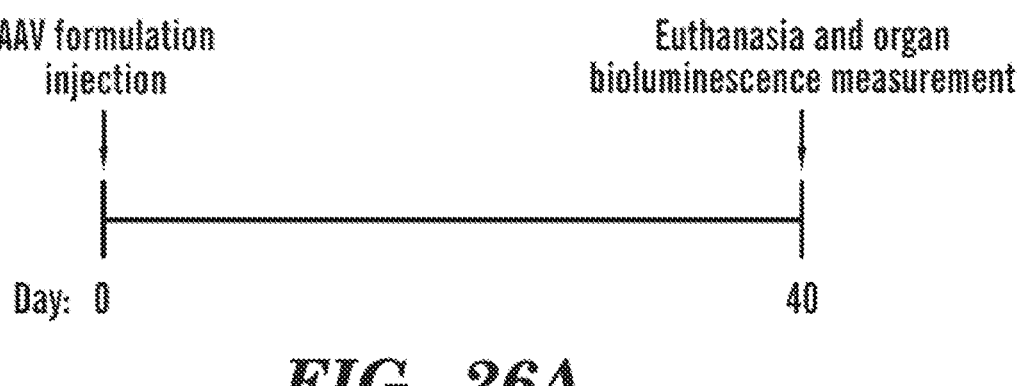
*FIG. 26A*
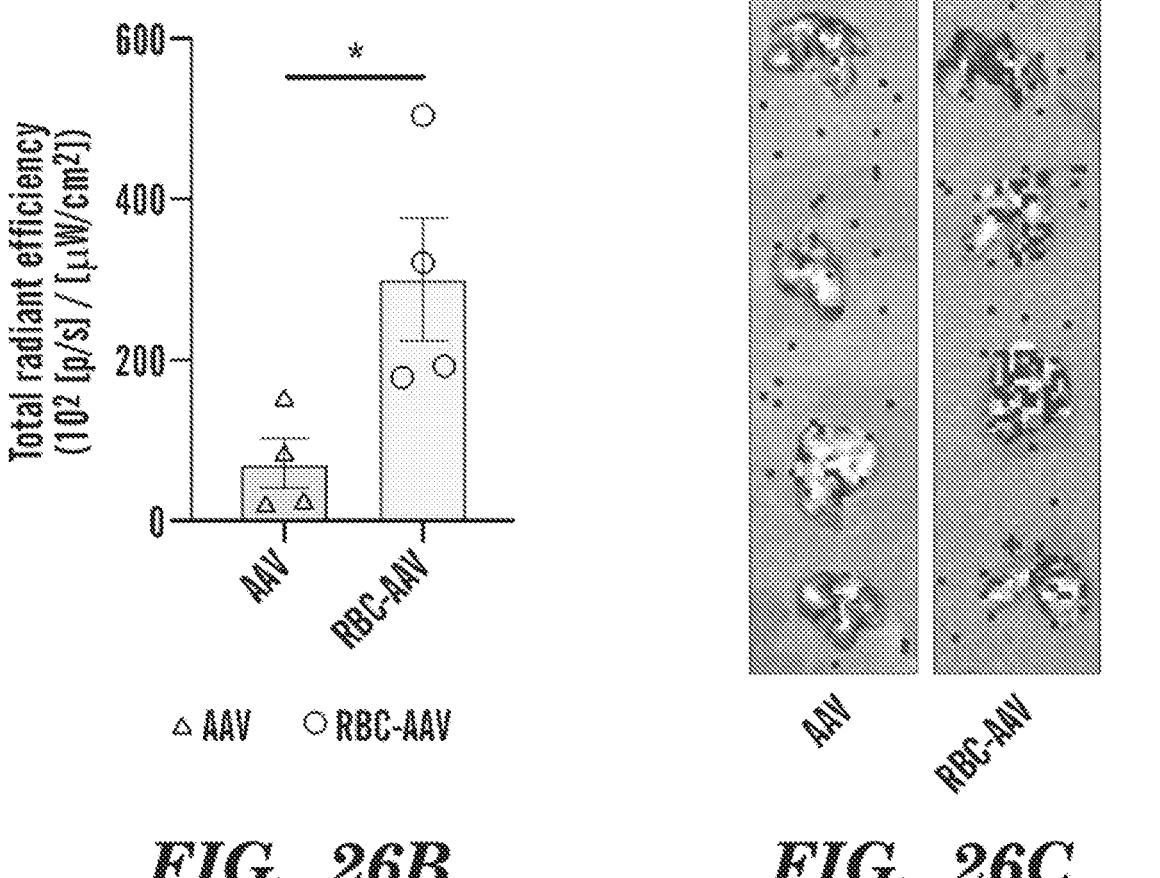
*FIG. 26B*                    *FIG. 26C*

AAV
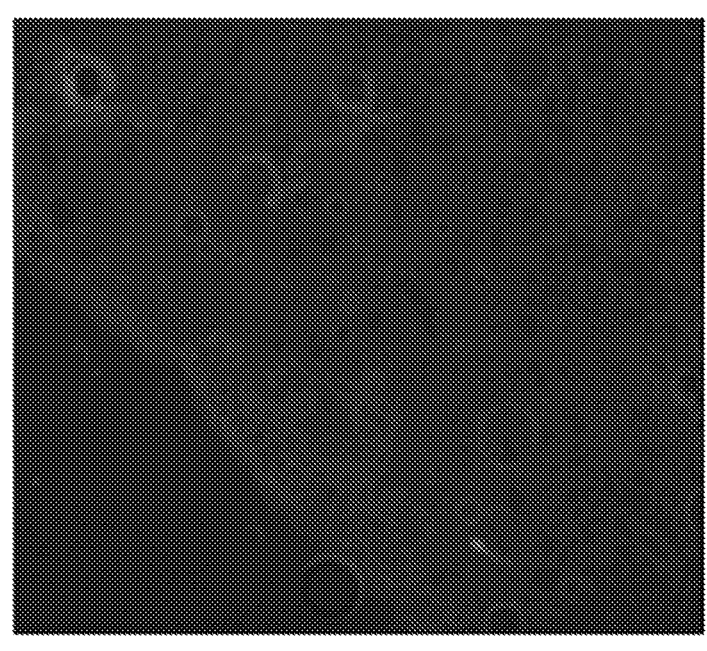
RBC-AAV
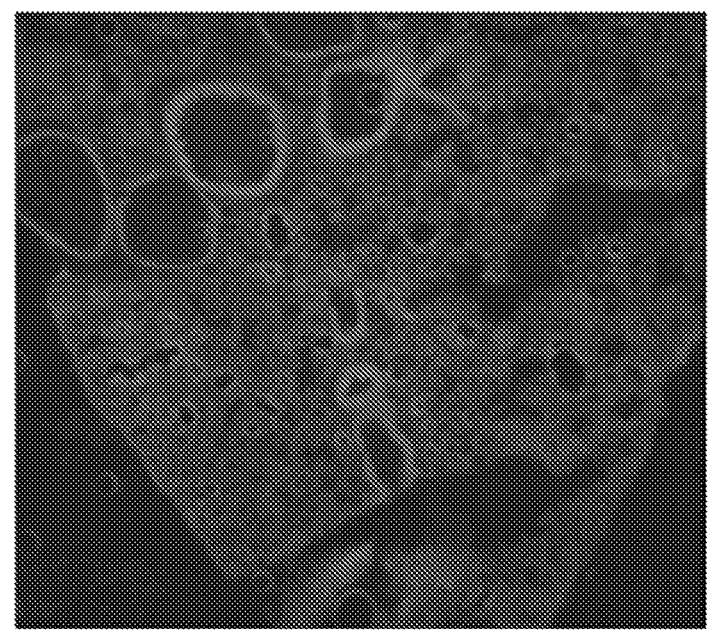
*FIG. 26D*

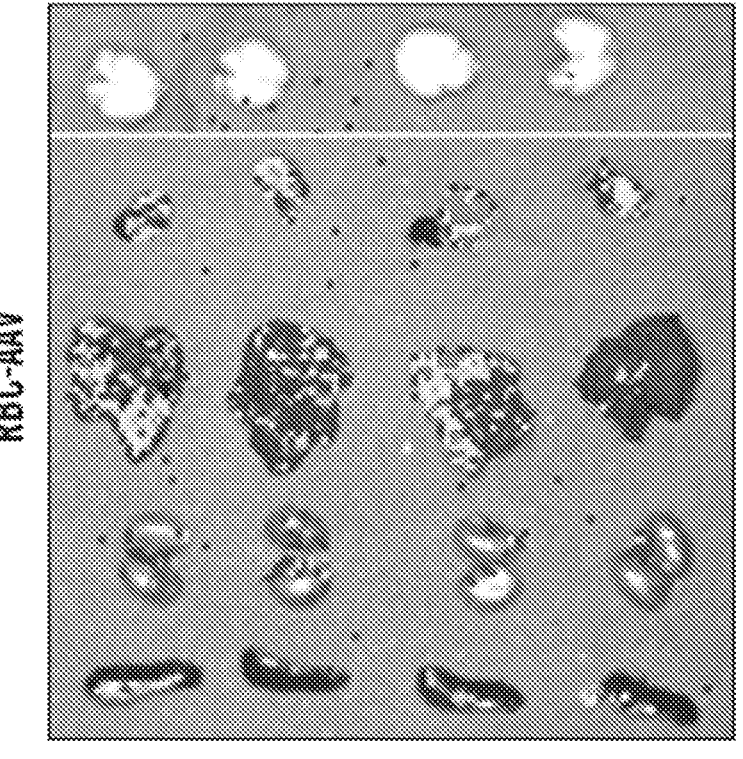
RBC-AAV
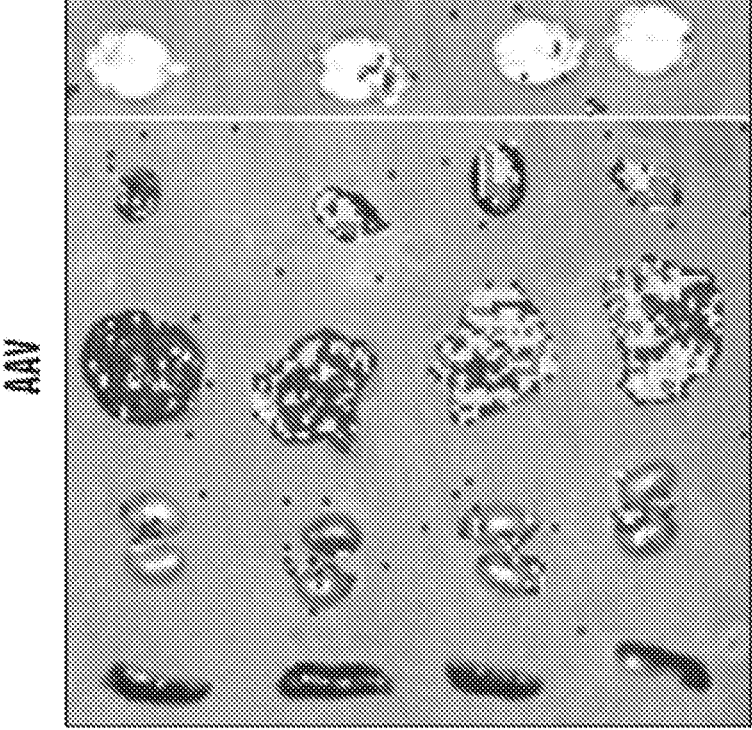
AAV
*FIG. 26F*

LIVING CELLS ENGINEERED WITH POLYPHENOL-FUNCTIONALIZED BIOLOGICALLY ACTIVE NANOCOMPLEXES

CROSS-REFERENCE TO RELATED APPLICATIONS

This application is a 35 U.S.C. § 371 National Phase Entry Application of International Application No. PCT/US2021/034132 filed May 26, 2021, which designates the U.S. and claims benefit under 35 U.S.C. § 119(e) of U.S. Provisional Application No. 63/031,614 filed May 29, 2020, the contents of which are incorporated herein by reference in their entireties.

TECHNICAL FIELD

The technology described herein relates to functionalizing nanocomplexes to alter or modulate the activity of mammalian cells.

BACKGROUND

Functionalization of living cells—the addition of biomolecules that provide new or modulated activity to the cells—has proven difficult. Methods of adding biomolecules to the cell surface often destroy or deactivate the biomolecule, damage or alter the cell in undesired way, or are time-consuming and specific to a particular biomolecule. Additionally, attempts to add biomolecules to a cell surface often result in internalization of the biomolecules (e.g., in Xu et al. EPPSCI 2018 87:165-196). A platform that permits rapid functionalization with a variety of biomolecules will have wide-ranging therapeutic applications, both in using cells to deliver therapeutic molecules, and in controlling cellular activity via functionalization to utilize therapeutic activity of the cells themselves.

SUMMARY

Described herein is the discovery of a nanocomplex system that permits a wide array of chemically divergent biomolecules to be readily adhered to mammalian cells without: 1) denaturing the biomolecules, 2) subjecting the biomolecules to phagocytosis or other internalization processes, or 3) damaging the mammalian cell. Such functionalization of mammalian cells has not been previously demonstrated and the success of this method is particularly surprising given the differences in mammalian cell surfaces and synthetic surfaces used in much prior work.

In one aspect of any of the embodiments, described herein is a functionalizing nanocomplex comprising: one or more polyphenol molecules; and one or more biomolecules. In some embodiments of any of the aspects, the one or more polyphenols collectively comprise at least one galloyl moiety and/or at least one catechol moiety. In some embodiments of any of the aspects, the one or more polyphenols collectively comprise at least one galloyl moiety and at least one catechol moiety. In some embodiments of any of the aspects, the one or more polyphenols each comprise at least one galloyl moiety and at least one catechol moiety. In some embodiments of any of the aspects, the polyphenol is tannic acid.

In some embodiments of any of the aspects, the stoichiometric ratio of polyphenol molecules to biomolecules is 570 or less relative polyphenol. In some embodiments of any of the aspects, the stoichiometric ratio of tannic acid molecules to biomolecules is 190 to 570. In some embodiments of any of the aspects, the stoichiometric ratio of tannic acid molecules to biomolecules is 190.

In some embodiments of any of the aspects, the biomolecule and/or active agent is a nucleic acid, protein, viral particle, viral vector, alkaloid, polysaccharide, anthocyanin, lipid, antiviral drug, antibiotic, chemotherapeutic, or combination thereof. In some embodiments of any of the aspects, the biomolecule and/or active agent comprises or is a protein. In some embodiments of any of the aspects, the biomolecule and/or active agent is ovalbumin, serum albumin, interleukin-4, an antibody or antibody reagent, cholera toxin subunit B, biotin, cytokine, or lectin. In some embodiments of any of the aspects, the antibody or antibody reagent is specific for an immune checkpoint protein.

In one aspect of any of the embodiments, described herein is a functionalized mammalian cell comprising at least one functionalizing nanocomplex as described herein, wherein the at least one functionalizing nanocomplex is adhered to the surface of the cell. In some embodiments of any of the aspects, the cell is a hematopoietic cell. In some embodiments of any of the aspects, the cell is an erythrocyte, T cell, monocyte, macrophage, neutrophil or natural killer cell. In some embodiments of any of the aspects, the biomolecule and/or active agent is an antibody or antibody reagent specific for an immune checkpoint protein and the cell is a macrophage. In some embodiments of any of the aspects, the biomolecule and/or active agent is an antibody or antibody reagent, cytokine, antiviral drug, antibiotic, or siRNA and the cell is a erythrocyte. In some embodiments of any of the aspects, the biomolecule and/or active agent is an antibody or antibody reagent, siRNA, or chemotherapeutic and the cell is a natural killer cell. In some embodiments of any of the aspects, the biomolecule and/or active agent is cytokine and the cell is a T cell. In some embodiments of any of the aspects, the biomolecule and/or active agent is an anti-inflammatory drug and the cell is a neutrophil. In some embodiments of any of the aspects, functionalizing nanocomplexes collectively comprising 10 to 1 trillion biomolecules are adhered to the surface of the cell.

In one aspect of any of the embodiments, described herein is a method of functionalizing a mammalian cell, the method comprising: a) combining one or more polyphenol molecules and one or more biomolecules; and b) contacting a mammalian cell with the combination resulting from step a; whereby a functionalizing nanocomplex forms and adheres to the surface of the cell.

In one aspect of any of the embodiments, described herein is a method of administering a biomolecule and/or active agent to a patient in need of treatment with the biomolecule, the method comprising administering a functionalized cell as described herein to the patient. In one aspect of any of the embodiments, described herein is a functionalized cell as described herein, for use in a method of administering a biomolecule and/or active agent to a patient in need of treatment with the biomolecule, the method comprising administering the functionalized cell as described herein to the patient. In some embodiments of any of the aspects, the cell is autologous to the patient. In some embodiments of any of the aspects, the cell is a erythrocyte and a plurality of the biomolecule and/or active agent administered to the patient is delivered to the lungs. In some embodiments of any of the aspects, the cell is a macrophage and a plurality of the biomolecule and/or active agent administered to the patient is delivered to the brain, a tumor, or a site of inflammation or autoimmune inflammation. In some embodiments of any of the aspects, the cell is a natural killer cell and a plurality of the biomolecule and/or active agent administered to the patient is delivered to a tumor. In some embodiments of any of the aspects, the cell is a T cell and a plurality of the biomolecule and/or active agent administered to the patient is delivered to a tumor. In some embodiments of any of the aspects, the cell is a neutrophil and a plurality of the biomolecule and/or active agent administered to the patient is delivered to the lungs or a site of inflammation.

BRIEF DESCRIPTION OF THE DRAWINGS

(FIG. 1A) Schematic diagram of the complexation between biomolecules and polyphenols. The polyphenol moieties can functionalize the biomolecules and still maintain the biological functions. (FIG. 1B) Versatile toolbox of cellular systems. We demonstrate the surface engineering of seven types of cells, including majorly circulatory and immune cells. (FIG. 1C) The assembled biomolecule-cell complex (Cellwrap) through the polyphenol-directed interfacial interactions on the surface of a cell. (FIG. 1D) Scanning electron microscopy (SEM) image of a naïve erythrocyte. (FIG. 1E) Optical microscopy image of Erythrocyte$_{plex}$ integrated with ovalbumin (OVA). Erythrocyte$_{plex}$ maintained the characteristic geometry of naïve erythrocytes with a typical concaved structure. (FIG. 1F) A wide range of biomolecules were used to demonstrate the versatile toolbox of biological payloads for the Cellwrap. This toolbox includes three main categories of biomolecules, including proteins, nucleic acids, and biological conjugators. Scale bars are 1 μm (FIG. 1D) and 5 μm (FIGS. 1E, 1F).

(FIG. 2A) Circular dichroism spectroscopy of BSA and polyphenol-functionalized BSA nanocomplexes. Though an increase in tannic acid concentration leads to a decrease in peak intensity, the feature of an α-helix structure maintained. (FIG. 2B) Relative activity of interleukin-4 and the formed interleukin-4 nanocomplexes with different concentrations of tannic acid (measured by ELISA assay). The addition of Fe$^{3+}$ (0.36 mg mL$^{-1}$) facilitated the interfacial assembly on the surfaces of cells during the Cellwrap formation process. (FIG. 2C) TEM images of a naïve erythrocyte and a BSA/Erythrocyte$_{plex}$. The reconstructed heat-map images show the difference of microtopology of cell surfaces due to the formation of nanostructured networks. (FIG. 2D) Cargo protein release kinetics from Erythrocyte$_{plex}$. PBS and FBS media simulate the in vitro assembly condition and serum environment, respectively. (FIG. 2E) Agglutination of erythrocyte and OVA/Erythrocyte$_{plex}$ was visualized using a U-shaped bottom plate, with aggregated Erythrocyte$_{plex}$ forming a diffused lattice. Polystyrene nanoparticles were used as a demonstration of nanoparticle-caused cytotoxicity to erythrocyte. (FIG. 2F) Osmotic fragility curves of Erythrocyte$_{plex}$ with different amounts of polyphenol-functionalized OVA nanocomplexes after immediate exposure to different concentrations of NaCl. Inset shows the percent hemolysis at 73 mM NaCl. Scale bars are 1 μm (FIG. 2C) and 200 nmg (FIG. 2C, magnified areas). Variation is represented by SE (error bars) from three independent replicates for all data points.

FIGS. 3A-3I demonstrate that erythrocyte$_{plex}$ selectively target lungs via particle-free mechanisms. (FIG. 3A) IVIS images of excised mouse lungs 5 min (0.08 hours) after the administration of OVA protein only and OVA/Erythrocyte$_{plex}$. Alexa 674-conjugated OVA was used for the fluorescence signal. (FIG. 3B) Biodistribution of OVA only and OVA/Erythrocyte$_{plex}$ 5 min after intravenous (IV) administration. (FIG. 3C) Biodistribution of OVA only and OVA/Erythrocyte$_{plex}$ 6 hours after IV administration. (FIG. 3D) Biodistribution of OVA only and OVA/Erythrocyte$_{plex}$ 24 hours after IV administration. (FIG. 3E) Lung to liver ratio of OVA delivered by the control counterpart and OVA/Erythrocyte$_{plex}$ throughout the entire measurement window. (FIG. 3F) Remaining OVA delivered by Erythrocyte$_{plex}$ through the time after 24 hours post-injection. Significantly different (one-way ANOVA followed by Tukey's HSD test): ***p<0.001. Variation is represented by SE (error bars) from three independent replicates for all data points. (FIG. 3G) Confocal florescence microscopy images of lung vascular capillary sections 5 min. 6 hours, and 24 hours after IV administration of OVA/Erythrocyte$_{plex}$. White arrows indicate the distribution of delivered OVA. Vascular capillaries were stained by Alexa 488-conjugated anti-CD31 antibody. (FIG. 3H) Biomimetic perfusion chamber experiments to characterize the formation of cell-free layers during the flow of native erythrocytes (top) and endothelial adhesive property of OVA/Erythrocyte$_{plex}$ (bottom). (FIG. 3I) Simulations of the difference of native erythrocytes and OVA/Erythrocyte$_{plex}$ flowing in the vascular channels. The introduction of an adhesive parameter leads to the change of cross-stream distributions. Scale bars are 50 μm (FIG. 3G) and (FIG. 3H).

FIGS. 4A-4H demonstrate the versatile cellular toolbox of cellwrap and the engineered Macrophage$_{plex}$ for sensing and chemotaxis. (FIG. 4A) Schematic diagram of the biological functions and crosstalk between the cellular components of the immune system. (FIG. 4B) Cellwrap allows the engineering of cell-based biohybrid systems from six types of cells. Alexa 488-conjugated BSA was used to visualize the assembly of protein nanocomplexes on the cell surface. (FIG. 4C) Schematic illustration of sensing and activation of Macrophage$_{plex}$. Alexa 488-conjugated anti-PD-L1 antibody was used as a model of biologically active molecules. (FIGS. 4D-4F) Confocal fluorescence microscopy image of a representative 4T1 breast cancer tumor spheroid. (FIG. 4D) Staining represents 4′,6-diamidino-2-phenylindole (DAPI), a nuclear stain. (FIG. 4E) Staining represents Macrophage$_{plex}$ carrying Alexa 488-conjugated anti-PD-L1 antibody. (FIG. 4F) Overlapped image of (FIG. 4D) and (FIG. 4E). The signal of anti-PD-L1 antibody was observed throughout the 4T1 breast cancer tumor spheroid. Scale bars are 10 μm (FIG. 4B), 50 μm (FIGS. 4D and 4E), 100 μm, and 20 μm (FIG. 4F, and inset). (FIG. 4G) Overall tumor growth curve monitored at different time-points (n=5). Inset shows the treatment schedule. Significantly different (two-way ANOVA followed by Tukey's HSD test): ** p<0.01. Variation is represented by SE (error bars) for all data points. (FIG. 4H) Tumor growth curve of individual mice in different treatment groups. The PD-L1 only group showed a low response rate (~40%); however, the anti-PD-L1/MacrophageWP group exhibited a significant increase of the response rate (~100%).

FIG. 5 demonstrates that polyphenol-functionalized protein nanocomplex size depending on the stoichiometric ratios of tannic acid (TA) and functionalized proteins (BSA). The concentration of BSA was 24 ug mL$^{-1}$ and different concentrations of TA were prepared (from 0.2 to 2.0 mg mL$^{-1}$ in the nanocomplex solutions. The upper scale values show the corresponding stoichiometric ratios. A critical concentration of TA can be observed at 0.6 mg mL$^{-1}$ (ratio of 570) and we chose the minimum concentration of 0.2 mg mL$^1$ in our standard preparation process for the biomolecular complexation and the formation of Cell$_{plex}$.

FIGS. 6A-6B depict fluorescence microscopy images of polyphenol-functionalized protein nanocomplex (BSA) and nucleic acid nanocomplexes (mRNA). At the polyphenol concentration of 0.2 mg ml) (stoichiometric ratio of 570), the biomolecule and/or active agent nanocomplexes self-assembled from BSA and mRNA show uniform and highly homogeneous status under the florescence microscopy observation. This molecular level of polyphenol-based functionalization enables the nanoscale assembly of biomolecules on the surfaces of cells to form Cellwrap. Scale bars are 5 μm.

FIG. 7 depicts dynamic light scattering (DLS) distribution of polyphenol-functionalized protein nanocomplex and its precursors of tannic acid and BSA protein. The complexation of tannic acid and BSA leads to the formation of a slightly larger size of distribution.

FIGS. 8A-8B depict TEM images of a native erythrocyte and an AAV2-GFP/Erythrocytes$_a$. Highly distributed AAV2 nanoparticles can be observed on the surface of Erythocyteplex. The inset shows the discrete AAV2 nanoparticles with no clear changes of the viral shape. Scale bars are 1 μm and 200 nm (inset).

FIGS. 13A-13B depict florescence microscopy image and bright field overlapped images of lung vascular capillary tissues stained by Alexa 488 probe-conjugated anti-CD31 antibody. The images show no significant florescence intensity after 6 h intravenous injection of OVA/Erythrocyte$_{plex}$. The negligible fluorescence signal suggested the delivery of cargo molecules to endothelium with no involvement of phagocytosis. Scale bars are 50 μm.

FIG. 14 depicts the Synvivo Chip design (CAT #101001) to mimic the vascular channels in lung.

(FIG. 18A) no adhesion, strong deformability-induced lift. $K_1$=0.16, $K_w$=0.27, $K_g$=0.018, Kc=Kc'=0.088, Kd=Kd'=0.31. (FIG. 18B) no adhesion, weak deformability-induced lift. $K_1$=0.16, Kw=0.034, $K_g$=0.0023, Kc=Kc'=0.088, Kd=Kd'=0.31. (FIG. 18C) weak adhesion. Kl=0.1. K−1=1, Kl=0.16, Kw,=0.068, $K_g$=0.0046, $K_c$=Kc'=0.088, Kd=K$_d$'=0.31. (FIG. 18D) strong adhesion. $K_l$=500, $K_{-l}$=1, Kl=0.16,=0.068, $K_g$=0.0046, Kc=Kc'=0.088, Kd=Kd'=0.31.

FIGS. 22A-22D demonstrate there is no penetration of PD-L1 antibodies into the tumor spheroid. (FIG. 22A) Bright-field microscopy image of representative 4T1 tumor spheroid. (FIGS. 22B-22D) Confocal florescence microscopy image of a representative 4T1 breast cancer tumor spheroid. (FIG. 22B) Staining represents 4,6-diamidino-2-phenylindole (DAPI), a nuclear stain. (FIG. 22C) Staining represents Alexa 488-conjugated PD-L1 antibody. (FIG. 22D) Overlapping image of (FIG. 22B) and (FIG. 22C). No significant signal of PD-L1 antibody was observed in the area of the 4T1 breast cancer tumor spheroid. Scale bars are 50 μm.

FIG. 23 depicts tumor growth monitored of individual mice at different time-points for the group treated with macrophage cell only.

(FIG. 25A) Representative SEM images of RBCs carrying AAV9. Scale bar: 1 μm. (FIG. 25B) Representative TEM images of AAV9 binding to RBC surface. Scale bar: 1 μm. (FIG. 25C) Binding efficiency of AAV9 onto RBCs. (FIG. 25D) Estimated average number of AAV9 loaded onto one RBC.

FIGS. 26A-26F demonstrate that RBC-AAV enhanced gene expression in the lung while led to similar gene expression levels in other major organs apart from the lung as compared to free AAV. (FIG. 26A) Schematic of the study schedule. (FIG. 26B) Luciferase gene expression level as indicated by bioluminescence intensity in the lungs 40 days after AAV or RBC-AAV administration. AAV carrying a luciferase gene was used in the studies. Significantly different (two-sided student's t test): *p<0.05. (FIG. 26C) Representative IVIS bioluminescence images of lungs on day 40 post AAV formulation administration. (FIG. 26D) Representative fluorescent images of lung sections after AAV or RBC-AAV administration. AAV carrying a eGFP gene was used in the study. Fluorescence indicates the expression level of eGFP. (FIG. 26E) Luciferase gene expression level as indicated by bioluminescence intensity in different organs 40 days after AAV or RBC-AAV administration. No significant difference was detected between AAV and RBC-AAV groups in any organs (two-sided student's t test). (FIG. 26F) Representative IVIS bioluminescence images of organs on day 40 post AAV formulation administration.

(FIG. 27A) Schematic of the study schedule for measuring antibody response against AAV after dosing. (FIG. 27B) Time-course of anti-AAV9 antibody titer measured by ELISA. (FIG. 27C) Schematic of the study schedule for the re-dosing study. (FIG. 27D) Luciferase gene expression level in the lungs as indicated by bioluminescence intensity 65 days after the first dose. (FIG. 27E) Luciferase gene expression level in other major organs as indicated by bioluminescence intensity 65 days after the first dose.

DETAILED DESCRIPTION

Figures 1A, 1B, 1C:
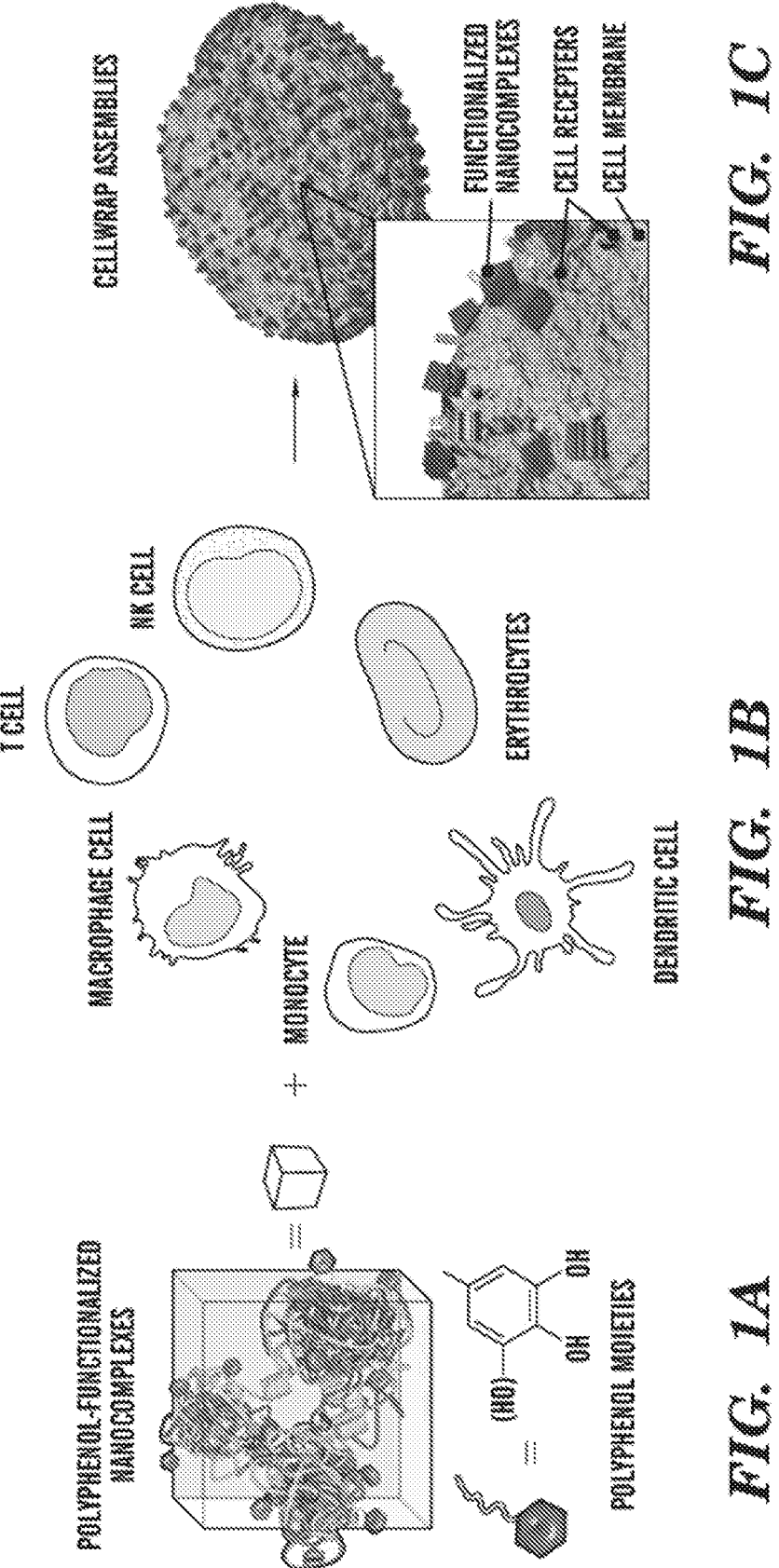
FIGS. 1A-1F demonstrate the modular assembly of cell-wrap through the assembly of polyphenol-functionalized biologically active nanocomplexes on cells.

The inventors have developed a platform for adhering diverse biomolecules to the surface of mammalian cells. The platform is referred to herein as Cellwrap (sometimes abbreviated Cellwp) or Cellplex. In some embodiments, when a specific cell type is used in the platform, the cell is specified, e.g., Erythrocytewrap or Macrophagewp. Unlike prior work in this area that resulted in internalization or denaturation of the biomolecules, the present methods and compositions provide surprising effectiveness. Cellwrap does not: 1) denature or inactivate the biomolecules, 2) result in phagocytosis or other internalization of the biomolecules by the mammalian cell, or 3) damage to the mammalian cell. Additionally, the present technology can reduce or eliminate the immune reaction to biomolecules and/or active agents. For example. FIGS. 27A-27E show that when AAV vector are delivered using the present platform, the immune reaction to the AAV is reduced, e.g., as compared to free AAV.

Accordingly, in one aspect of any of the embodiments, provided herein is a functionalizing nanocomplex comprising: a) one or more polyphenol molecules; and b) one or more biomolecules and/or active agents.

As used herein, "nanocomplex" refers to complexes of molecules, the complex having a size of about 0.1 nm to about 1000 nm. Further, the nanocomplex can be of any shape or form, e.g., spherical, rod, elliptical, cylindrical, capsule, or disc. In some embodiments of any of the aspects, the nanoparticle is of size from about 0.1 nm to about 100 nm, from about 0.1 nm to about 10 nm, or from about 1 nm to about 10 nm. In some embodiments of any of the aspects, the nanoparticle is of size from 0.1 nm to 100 nm, from 0.1 nm to 10 nm, or from 1 nm to 10 nm. In some embodiments of any of the aspects, the nanoparticle is less about 10 nm or smaller in size. In some embodiments of any of the aspects, the nanoparticle is 10 nm or smaller in size. A nanocomplex is functionalizing when it is capable of providing a new or modulated function or activity to a cell when it is adhered to the cell surface. That is, a nanocomplex is functionalizing when it comprises a molecule or moiety that can has a biological function or activity, or which can modulate the biological function or activity of a cell.

As used herein, "polyphenol" refers to a molecule comprising multiple phenol structural units. In some embodiments of any of the aspects, polyphenol is defined according to the WBSSH definition. In some embodiments of any of the aspects, the polyphenol comprises at least one galloyl moiety. In some embodiments of any of the aspects, the polyphenol comprises at least one catechol moiety. In some embodiments of any of the aspects, the polyphenol comprises at least one galloyl moiety and one catechol moiety. In some embodiments of any of the aspects, each polyphenol molecule comprises at least one galloyl moiety. In some embodiments of any of the aspects, each polyphenol molecule comprises at least one catechol moiety. In some embodiments of any of the aspects, each polyphenol molecule comprises at least one galloyl moiety and one catechol moiety. In some embodiments of any of the aspects, multiple different polyphenols can be present in the functionalizing nanocomplex. In such embodiments, the polyphenols can collective comprise at least one galloyl moiety and/or at least one catechol moiety.

As used herein, "galloyl" refers a gallic acid moiety or group found in a larger molecule. Gallic acid is depicted in Structure I.

Structure I

As used herein, "catechol" refers a moiety or group having the formula of Structure II, found in a larger molecule.

Structure II

Suitable polyphenols include but are not limited to tannins, gallic acid esters, proanthocyanins, and hydrolyzable tannins. In some embodiments of any of the aspects, the polyphenol is tannic acid. Tannic acid (1,2,3,4,6-penta-O-{3,4-dihydroxy-5-[(3,4,5-trihydroxy benzoyl)oxy]benzoyl}-D-glucopyranose) can comprise quercitannic acid or gallotannic acid. Quer. In some embodiments of any of the aspects, the polyphenols of the functionalizing nanocomplex comprise, consist of, or consist essentially of tannic acid.

Structure III (Tannic Acid)

The functionalizing nanocomplexes described herein comprise biomolecules. As used herein, "biomolecule" refers to any organic molecule that is part of or from a living organism. In some embodiments of any of the aspects, the biomolecule and/or active agent and/or active agent is an entity which is normally not present or not present at the levels being administered and/or provided to a cell, tissue or subject. A biomolecule and/or active agent and/or active agent can be selected from a group comprising: chemicals; small organic or inorganic molecules; signaling molecules; nucleic acid sequences; nucleic acid analogues; proteins; peptides; enzymes; aptamers; peptidomimetic, peptide derivative, peptide analogs, antibodies; intrabodies; biological macromolecules, extracts made from biological materials such as bacteria, plants, fungi, or animal cells or tissues; naturally occurring or synthetic compositions or functional fragments thereof. In some embodiments, the agent is any chemical, entity or moiety, including without limitation synthetic and naturally-occurring non-proteinaceous entities. Suitable biomolecules and/or active agents can include, but are not limited to: a nucleic acid (e.g., a vector, inhibitory nucleic acid, siRNA, etc), protein, viral particle, viral vector, alkaloid, polysaccharide, anthocyanin, lipid, antiviral drug, antibiotic, chemotherapeutic, or combination thereof. In some embodiments, the biomolecule and/or active agent and/or active agents comprises a protein or is a protein. In some embodiments of any of the aspects, the protein is ovalbumin, serum albumin, interleukin-4, an antibody or antibody reagent, cholera toxin subunit B, biotin, cytokine, or lectin. In some embodiments of any of the aspects, the antibody or antibody reagent is specific for an immune checkpoint protein.

A nucleic acid molecule, as described herein, can be a vector, an expression vector, an inhibitory nucleic acid, an aptamer, a template molecule or cassette (e.g., for gene editing), or a targeting molecule (e.g., for CRISPR-Cas technologies), or any other nucleic acid molecule. The nucleic acid molecule can be RNA. DNA, or synthetic or modified versions thereof.

The biomolecule(s) and/or active agent(s) and polyphenol(s) of a functionalizing nanocomplex are in combination with each other to form the nancomplex. As used herein, "in combination with" refers to two or more substances being present in the same formulation in any molecular or physical arrangement, e.g. bound to each other, complexed, etc. A nanocomplex comprises two or more molecular structures that are linked by a direct or indirect covalent or non-covalent bond. Non-covalent interactions include, but are not limited to, electrostatic interactions, hydrogen bonding interactions, van der Waals interactions, dipole-dipole interactions, $\pi$-$\pi$ stacking, magnetic interactions, and metal coordination. In some embodiments of any of the aspects, the biomolecule(s) and/or active agent(s) are complexed with the polyphenol(s) via non-covalent bonds. In some embodiments of any of the aspects, the biomolecule(s) and/or active agent(s) are complexed with the polyphenol(s) via covalent bonds.

In some embodiments of any of the aspects, a nanocomplex can comprise 2 or more, 3 or more, 4 or more, or 5 or more different polyphenols. In some embodiments of any of the aspects, a nanocomplex can comprise 2 or more, 3 or more, 4 or more, or 5 or more different biomolecules and/or active agents.

As described in the examples herein, the ratio of polyphenol molecules to biomolecules and/or active agents can influence the formation of the nanocomplexes. In some embodiments of any of the aspects, the stoichiometric ratio of polyphenol molecules to biomolecules and/or active agents is about 570:1 or less relative polyphenol molecule. In some embodiments of any of the aspects, the stoichiometric ratio of polyphenol molecules to biomolecules and/or active agents is 570:1 or less relative polyphenol molecule. In some embodiments of any of the aspects, the stoichiometric ratio of polyphenol molecules to biomolecules and/or active agents is about 190:1 or more relative polyphenol molecule. In some embodiments of any of the aspects, the stoichiometric ratio of polyphenol molecules to biomolecules and/or active agents is 190:1 or more relative polyphenol molecule. In some embodiments of any of the aspects, the stoichiometric ratio of polyphenol molecules to biomolecules and/or active agents is about 570:1 to about 190:1. In some embodiments of any of the aspects, the stoichiometric ratio of polyphenol molecules to biomolecules and/or active agents is 570:1 to 190:1.

The functionalizing nanocomplexes described herein are unique in their ability to adhere to or associate with the surface of a mammalian cell, e.g., unlike prior art molecules which cannot adhere or which are rapidly internalized. As used herein, "adhere" refers to the ability of the nanocomplex to attach to, cling to, stick to, or remain in association with the surface of the cell. Adhesion can comprise covalent and/or non-covalent interactions. In some embodiments of any of the aspects, a functionalizing nanocomplex can adhere to a mammalian cell surface for at least 1 hour, at least 2 hours, at least 6 hours, at least 12 hours, at least 24 hours, at least 48 hours, at least 2 days, at least 3 days, at least 1 week, or at least 2 weeks, e.g., before dissociating from the cell, being internalized by the cell, or degrading. In some embodiments of any of the aspects, a functionalizing nanocomplex can adhere to a mammalian cell surface for at least 24 hours, e.g., before dissociating from the cell, being internalized by the cell, or degrading. In some embodiments of any of the aspects, a functionalizing nanocomplex can adhere to a mammalian cell surface for at least 48 hours, e.g., before dissociating from the cell, being internalized by the cell, or degrading. In some embodiments of any of the aspects, at least 20%, at least 50%, at least 75%, at least 80%, at least 85%, at least 90%, or at least 95% of a population of functionalizing nanocomplex can adhere to a mammalian cell surface for at least 1 hour, at least 2 hours, at least 6 hours, at least 12 hours, at least 24 hours, at least 2 days, at least 3 days, at least 1 week, or at least 2 weeks.

In one aspect of any of the embodiments, provided herein is a functionalized mammalian cell comprising at least one functionalizing nanocomplex as described herein, wherein the at least one functionalizing nanocomplex is adhered to the surface of the cell. As used herein, "mammalian" or "mammal" refers to refers to any animal that falls within a taxonomic classification of mammals. Mammals can refer to humans or non-human primates. Mammals can refer to livestock or pets including, for example, dogs, cats, rodents (including rabbits, mice, black rats, hamsters) and the like. Mammals may refer to agricultural animals including, for example, cows, sheep, pigs, horses and the like. In some embodiments, the cell is a primate cell. In some embodiments, the cell is a human cell. In some embodiments, the cell is a dog or cat cell. In some embodiments, the cell is a murine cell. In some embodiments, the cell is autologous to a patient.

The methods and compositions described herein are contemplated for use with all mammalian cells types. In some embodiments of any of the aspects, the cell is a hematopoietic cells. In some embodiments of any of the aspects, the cell is an erythrocyte (red blood cell), T cell, monocyte, macrophage, neutrophil, or natural killer (NK) cell.

Particular combinations of biomolecules and/or active agents and cell types are contemplated herein, including:

| Biomolecule and/or active agent and/or active agent | Cell Type |
|---|---|
| An antibody or antibody reagent specific for an immune checkpoint protein | Macrophage |
| An antibody or antibody reagent, an antibody or antibody reagent specific for an immune checkpoint protein, a cytokine, antiviral drug, viral vector, antibiotic, or siRNA | Erythrocyte |
| An antibody or antibody reagent, an antibody or antibody reagent specific for an immune checkpoint protein siRNA, or chemotherapeutic | Natural killer cell |
| Cytokine | T cell |
| Anti-inflammatory drug | Neutrophil |

In some embodiments of any of the aspects, functionalizing nanocomplexes collectively comprising 10 to 1 trillion biomolecules and/or active agents are adhered to the surface of the cell. In some embodiments of any of the aspects, functionalizing nanocomplexes collectively comprising 1 to 10 trillion biomolecules and/or active agents are adhered to the surface of the cell. In some embodiments of any of the aspects, functionalizing nanocomplexes collectively comprising 100 to 1 trillion biomolecules and/or active agents are adhered to the surface of the cell. In some embodiments of any of the aspects, functionalizing nanocomplexes collectively comprising 1.000 to 1 trillion biomolecules and/or active agents are adhered to the surface of the cell. In some embodiments of any of the aspects, functionalizing nanocomplexes collectively comprising 10 to 100,00 biomolecules and/or active agents are adhered to the surface of the cell.

Functionalizing nanocomplexes as described herein can be assembled and adhered to a mammalian cell according to the protocols provided in the Examplex and the following method. In one aspect of any the embodiments, provided herein is a method of functionalizing a mammalian cell, the method comprising: a) combining one or more polyphenol molecules and one or more biomolecules and/or active agents; and b) contacting a mammalian cell with the combination resulting from step a; whereby a functionalizing nanocomplex forms and adheres to the surface of the cell. In some embodiments of any the aspects, the combining step occurs before the contacting step. In some embodiments of any the aspects, the combining step occurs at least 30 seconds, at least 1 minute, at least 5 minutes, at least 10 minutes, at least 15 minutes, at least 20 minutes, at least 30 minutes, at least 45 minutes, at least 60 minutes or more before the contacting step.

In one aspect of any of the embodiments, described herein is a method of administering a biomolecule and/or active agent and/or active agent to a patient in need of treatment with the biomolecule and/or active agent and/or active agent, the method comprising administering a functionalized mammalian cell as described herein to the patient.

In some embodiments of any of the aspects, the cell is autologous to the patient.

Particular cell types tend to accumulate to, migrate to, or travel through specific tissues and sites in the body. Accordingly, depending on the location that the user desires to deliver the biomolecule and/or active agent and/or active agent to (e.g., where a site of disease is located), particular cell types may be preferred. For example, in some embodiments of any of the aspects, the cell is an erythrocyte and a plurality of the biomolecule and/or active agent administered to the patient is delivered to the lungs. In some embodiments of any of the aspects, the cell is a macrophage and a plurality of the biomolecule and/or active agent administered to the patient is delivered to the brain, a tumor, or a site of inflammation or autoimmune inflammation. In some embodiments of any of the aspects, the cell is a natural killer cell and a plurality of the biomolecule and/or active agent administered to the patient is delivered to a tumor. In some embodiments of any of the aspects, the cell is a T cell and a plurality of the biomolecule and/or active agent administered to the patient is delivered to a tumor. In some embodiments of any of the aspects, the cell is a neutrophil and a plurality of the biomolecule and/or active agent administered to the patient is delivered to the lungs or a site of inflammation.

In some embodiments of any of the aspects, a composition as described herein, e.g., a functionalizing nanocomplex or functionalized mammalian cell, can further comprise a pharmaceutically acceptable carrier. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically, such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present disclosure can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the methods described herein that will be effective in the treatment of a particular disorder or condition will depend on the nature of the disorder or condition, and can be determined by standard clinical techniques. Suitable pharmaceutical carriers are described in Remington's Pharmaceutical Sciences, A. Osol, a standard reference text in this field of art. For example, a parenteral composition suitable for administration by injection is prepared by dissolving 1.5% by weight of active ingredient in 0.9% sodium chloride solution.

The term "carrier" in the context of a pharmaceutical carrier refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations, and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences, 18th Ed., Gennaro, ed. (Mack Publishing Co., 1990). The formulation should suit the mode of administration.

Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soy bean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23)

serum component, such as serum albumin. HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active compound. The term "pharmaceutically acceptable carrier" excludes tissue culture medium.

In some embodiments of any of the aspects, a composition as described herein, e.g., a functionalizing nanocomplex or functionalized mammalian cell, can be formulated as an oral, parenteral, intravenous, intramuscular, subcutaneous, transdermal, airway (aerosol), pulmonary, cutaneous, injection, or intratumoral formulation.

In one aspect of any of the embodiments, the composition or combination described herein is for a method of administering or delivering at least biomolecule, e.g., for the treatment of a disease. In one aspect of any of the embodiments, described herein is a method of administering at least one biomolecule and/or active agent or functionalized mammalian cell, the method comprising administering a functionalized mammalian cell as described herein. In one aspect of any of the embodiments, described herein is a method of treating a disease by administering at least one biomolecule and/or active agent or functionalized mammalian cell, the method comprising administering the functionalized mammalian cell as described herein. A biomolecule and/or active agent can be directly therapeutic, or modulate the activity of the functionalized cell such that the cell exhibits a therapeutic effect.

In one aspect of any of the embodiments, described herein is a method of administering a viral vector and/or reducing the immune clearance of viral vectors, the method comprising administering a viral particle or viral vector adhered to a cell (e.g., mammalian cell and/or a red blood cell). The adherence can be via or mediated by one or more nanocomplexes. In some embodiments of any of the aspects, the viral particle or viral vector adhered to a cell can be a functionalized cell as described herein. In some embodiments of any of the aspects, the viral particle or viral vector adhered to a cell can be a nanocomplex as described herein.

In one aspect of any of the embodiments, described herein is a method of gene therapy comprising administering a functionalized cell as described herein, wherein the biomolecule and/or active agent comprises a nucleic acid sequence, e.g., a nucleic acid sequence suitable for or configured for gene therapy. Nucleic acid sequences suitable or configured for gene therapy will vary in structure and sequence depending on the nature of the gene therapy desired. One of skill in the art is well aware of how to select and/or design such sequences. Merely by way of non-limiting example, such sequences can comprise one or more of: one or two homology arms to direct recombination, a sequence to be inserted into the genome, a sequence to direct repair of a mutation in the genome, a sequence comprising an expression cassette, and the like. In some embodiments of any of the aspects, the gene therapy target (e.g., the cells to be targeted, the cells which display the pathology or disease requiring gene therapy, or the like) is primarily in the lungs. In some embodiments of any of the aspects, the gene therapy target (e.g., the cells to be targeted, the cells which display the pathology or disease requiring gene therapy, or the like) is primarily in the brain.

In some embodiments, the methods described herein relate to treating a subject having or diagnosed as having a condition with a composition as described herein, e.g., a functionalizing nanocomplex or functionalized mammalian cell. Subjects having cancer can be identified by a physician using current methods of diagnosing cancer. Symptoms and/or complications of cancer which characterize these conditions and aid in diagnosis are well known in the art and include but are not limited to, fevers, weight loss, bumps or tumors. Tests that may aid in a diagnosis of, e.g. cancer include, but are not limited to, biopsy and imaging exams. A family history of cancer, or exposure to risk factors for cancer can also aid in determining if a subject is likely to have cancer or in making a diagnosis of cancer.

The compositions and methods described herein can be administered to a subject having or diagnosed as having a condition described herein. In some embodiments, the methods described herein comprise administering an effective amount of compositions described herein, e.g. a composition comprising a functionalizing nanocomplex or functionalized mammalian cell, to a subject in order to alleviate a symptom of a condition. As used herein, "alleviating a symptom" is ameliorating any marker or symptom associated with a condition. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, injection, or intratumoral administration. Administration can be local or systemic.

Oral administration can comprise providing tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Oral formulations can comprise discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions may be prepared by methods of pharmacy well known to those skilled in the art. See generally, Remington: The Science and Practice of Pharmacy, 21st Ed., Lippincott, Williams, and Wilkins, Philadelphia PA. (2005).

In some embodiments, parenteral administration comprises delivery to a tumor, e.g., a cancer tumor. In some embodiments of any of the aspects, a composition described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of a composition as described herein are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of an ingredient in a composition as disclosed herein can also be incorporated into the parenteral dosage forms of the disclosure, including conventional and controlled-release parenteral dosage forms.

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. For example, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the composition comprising a functionalized mammalian cell can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

The term "effective amount" as used herein refers to the amount of a composition needed to alleviate at least one or more symptom of the disease or disorder, and relates to a sufficient amount of pharmacological composition to provide the desired effect. The term "therapeutically effective amount" therefore refers to an amount of a composition that is sufficient to provide a particular effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the active compound, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for tumor growth, or inflammation, among others. The dosage can be determined by a physician and adjusted, as necessary, to suit observed effects of the treatment.

In some embodiments of any of the aspects, the composition as described herein, e.g., a composition comprising a functionalized mammalian cell, is administered as a monotherapy, e.g., another treatment for the condition is not administered to the subject.

In some embodiments of any of the aspects, the methods described herein can further comprise administering a second agent and/or treatment to the subject, e.g. as part of a combinatorial therapy, either in a composition described herein, or as a separate formulation. For example, non-limiting examples of a second agent and/or treatment for treatment of cancer can include radiation therapy, surgery, gemcitabine, cisplastin, paclitaxel, carboplatin, bortezomib, AMG479, vorinostat, rituximab, temozolomide, rapamycin, ABT-737, PI-103; alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enedivne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above. In addition, the methods of treatment can further include the use of radiation or radiation therapy. Further, the methods of treatment can further include the use of surgical treatments.

By way of non-limiting example, if a subject is to be treated for pain or inflammation according to the methods described herein, the subject can also be administered a second agent and/or treatment known to be beneficial for subjects suffering from pain or inflammation. Examples of such agents and/or treatments include, but are not limited to, non-steroidal anti-inflammatory drugs (NSAIDs-such as aspirin, ibuprofen, or naproxen); corticosteroids, including glucocorticoids (e.g. cortisol, prednisone, prednisolone, methylprednisolone, dexamethasone, betamethasone, triamcinolone, and beclometasone); methotrexate; sulfasalazine; leflunomide; anti-TNF medications; cyclophosphamide; pro-resolving drugs; mycophenolate; or opiates (e.g. endorphins, enkephalins, and dynorphin), steroids, analgesics, barbiturates, oxycodone, morphine, lidocaine, and the like.

In certain embodiments, an effective dose of a composition described herein, e.g. a composition comprising a functionalized mammalian cell, can be administered to a patient once. In certain embodiments, an effective dose a composition described herein, e.g. a composition comprising a functionalized mammalian cell, can be administered to a patient repeatedly. For systemic administration, subjects can be administered a therapeutic amount of a composition described herein, e.g. a composition comprising a functionalized mammalian cell, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more. In some embodiments of any of the aspects, the at least one biomolecule and/or active agent is present in the composition at a dose of from about 1.0-20.0 mg/kg. In some embodiments of any of the aspects, the at least one biomolecule and/or active agent is present in the composition at a dose of from 1.0-20.0 mg/kg.

Effective amounts, toxicity, and therapeutic efficacy can be determined by standard pharmaceutical procedures in cell cultures or experimental animals, e.g., for determining the minimal effective dose and/or maximal tolerated dose. The dosage can vary depending upon the dosage form employed and the route of administration utilized. A therapeutically effective dose can be estimated initially from cell culture assays. Also, a dose can be formulated in animal models to achieve a dosage range between the minimal effective dose and the maximal tolerated dose. The effects of any particular dosage can be monitored by a suitable bioassay, e.g., assay for tumor growth and/or size among others. The dosage can be determined by a physician and adjusted, as necessary, to suit observed effects of the treatment.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the composition. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition described herein, e.g. a composition comprising a functionalized mammalian cell, can be administered over a period of time, such as over a 5 minute, 10 minute, 15 minute, 20 minute, or 25 minute period.

The dosage ranges for the administration of the compositions described herein, according to the methods described herein depend upon, for example, the form of the active compound, its potency, and the extent to which symptoms, markers, or indicators of a condition described herein are desired to be reduced, for example the percentage reduction desired for symptoms or markers. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of a composition described in, e.g. the treatment of a condition described herein, or to induce a response as described herein can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. tumor growth or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy can be assessed in animal models of a condition described herein, for example treatment of cancer or autoimmune conditions. When using an experimental animal model, efficacy of treatment is evidenced when a statistically significant change in a marker is observed.

In vitro and animal model assays are provided herein which allow the assessment of a given dose of a composition described herein, e.g. a composition comprising a functionalized mammalian cell. By way of non-limiting example, the effects of a dose of a composition comprising a functionalized mammalian cell can be assessed by using the models described in the Examples herein.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level, "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomolgous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of a disease or condition. A subject can be male or female.

A subject can be one who has been previously diagnosed with or identified as suffering from or having a condition in need of treatment (e.g. cancer) or one or more complications related to such a condition, and optionally, have already undergone treatment for the condition or the one or more complications related to the condition. Alternatively, a subject can also be one who has not been previously diagnosed as having the condition or one or more complications related to the condition. For example, a subject can be one who exhibits one or more risk factors for the condition or one or more complications related to the condition or a subject who does not exhibit risk factors.

A "subject in need" of treatment for a particular condition can be a subject having that condition, diagnosed as having that condition, or at risk of developing that condition.

As used herein, the term "cancer" relates generally to a class of diseases or conditions in which abnormal cells divide without control and can invade nearby tissues. Cancer cells can also spread to other parts of the body through the blood and lymph systems. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord.

In some embodiments of any of the aspects, the cancer is a primary cancer. In some embodiments of any of the aspects, the cancer is a malignant cancer. As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood). As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor. As used herein, the term "benign" or "non-malignant" refers to tumors that may grow larger but do not spread to other parts of the body. Benign tumors are self-limited and typically do not invade or metastasize.

A "cancer cell" or "tumor cell" refers to an individual cell of a cancerous growth or tissue. A tumor refers generally to a swelling or lesion formed by an abnormal growth of cells, which may be benign, pre-malignant, or malignant. Most cancer cells form tumors, but some, e.g., leukemia, do not necessarily form tumors. For those cancer cells that form tumors, the terms cancer (cell) and tumor (cell) are used interchangeably.

As used herein the term "neoplasm" refers to any new and abnormal growth of tissue, e.g., an abnormal mass of tissue, the growth of which exceeds and is uncoordinated with that of the normal tissues. Thus, a neoplasm can be a benign neoplasm, premalignant neoplasm, or a malignant neoplasm.

A subject that has a cancer or a tumor is a subject having objectively measurable cancer cells present in the subject's body. Included in this definition are malignant, actively proliferative cancers, as well as potentially dormant tumors or micrometastases. Cancers which migrate from their original location and seed other vital organs can eventually lead to the death of the subject through the functional deterioration of the affected organs.

Examples of cancer include but are not limited to, carcinoma, lymphoma, blastoma, sarcoma, leukemia, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma (GBM); hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome A "cancer cell" is a cancerous, pre-cancerous, or transformed cell, either in vivo, ex vivo, or in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage independence, malignancy, loss of contact inhibition and density limitation of growth, growth factor or serum independence, tumor specific markers, invasiveness or metastasis, and tumor growth in suitable animal hosts such as nude mice.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function, "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing. The terms also refer to fragments or variants of the polypeptide that maintain at least 50% of the activity or effect, of the full length polypeptide. Conservative substitution variants that maintain the activity of wildtype proteins will include a conservative substitution as defined herein. The identification of amino acids most likely to be tolerant of conservative substitution while maintaining at least 50% of the activity of the wildtype is guided by, for example, sequence alignment with homologs or paralogs from other species. Amino acids that are identical between homologs are less likely to tolerate change, while those showing conservative differences are obviously much more likely to tolerate conservative change in the context of an artificial variant. Similarly, positions with non-conservative differences are less likely to be critical to function and more likely to tolerate conservative substitution in an artificial variant. Variants, fragments, and/or fusion proteins can be tested for activity, for example, by administering the variant to an appropriate animal model of a disease as described herein.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., genomic DNA or cDNA. Suitable RNA can include, e.g., mRNA.

In some embodiments of any of the aspects, the nucleic acid is an inhibitory nucleic acid. In some embodiments of any of the aspects, inhibitors of the expression of a given gene can be an inhibitory nucleic acid. As used herein, "inhibitory nucleic acid" refers to a nucleic acid molecule which can inhibit the expression of a target, e.g., double-stranded RNAs (dsRNAs), inhibitory RNAs (iRNAs), and the like. In some embodiments of any of the aspects, the inhibitory nucleic acid can be a silencing RNA (siRNA), microRNA (miRNA), or short hairpin RNA (shRNA).

Double-stranded RNA molecules (dsRNA) have been shown to block gene expression in a highly conserved regulatory mechanism known as RNA interference (RNAi). The inhibitory nucleic acids described herein can include an RNA strand (the antisense strand) having a region which is 30 nucleotides or less in length, i.e., 15-30 nucleotides in length, generally 19-24 nucleotides in length, which region is substantially complementary to at least part the targeted mRNA transcript. The use of these iRNAs enables the targeted degradation of mRNA transcripts, resulting in decreased expression and/or activity of the target.

As used herein, the term "iRNA" refers to an agent that contains RNA (or modified nucleic acids as described below herein) and which mediates the targeted cleavage of an RNA transcript via an RNA-induced silencing complex (RISC) pathway. In some embodiments of any of the aspects, an iRNA as described herein effects inhibition of the expression and/or activity of a target. In some embodiments of any of the aspects, contacting a cell with the inhibitor (e.g. an iRNA) results in a decrease in the target mRNA level in a cell by at least about 5%, about 10%, about 20%, about 30%, about 40%, about 50%, about 60%, about 70%, about 80%, about 90%, about 95%, about 99%, up to and including 100% of the target mRNA level found in the cell without the presence of the iRNA. In some embodiments of any of the aspects, administering an inhibitor (e.g. an iRNA) to a subject results in a decrease in the target mRNA level in the subject by at least about 5%, about 10%, about 20%, about 30%, about 40%, about 50%, about 60%, about 70%, about 80%, about 90%, about 95%, about 99%, up to and including 100% of the target mRNA level found in the subject without the presence of the iRNA.

In some embodiments of any of the aspects, the iRNA can be a dsRNA. A dsRNA includes two RNA strands that are sufficiently complementary to hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of the target, e.g., it can span one or more intron boundaries. The other strand (the sense strand) includes a region that is complementary to the antisense strand, such that the two strands hybridize and form a duplex structure when combined under suitable conditions. Generally, the duplex structure is between 15 and 30 base pairs in length inclusive, more generally between 18 and 25 base pairs in length inclusive, yet more generally between 19 and 24 base pairs in length inclusive, and most generally between 19 and 21 base pairs in length, inclusive. Similarly, the region of complementarity to the target sequence is between 15 and 30 base pairs in length inclusive, more generally between 18 and 25 base pairs in length inclusive, yet more generally between 19 and 24 base pairs in length inclusive, and most generally between 19 and 21 base pairs in length nucleotides in length, inclusive. In some embodiments of any of the aspects, the dsRNA is between 15 and 20 nucleotides in length, inclusive, and in other embodiments, the dsRNA is between 25 and 30 nucleotides in length, inclusive. As the ordinarily skilled person will recognize, the targeted region of an RNA targeted for cleavage will most often be part of a larger RNA molecule, often an mRNA molecule. Where relevant, a "part" of an mRNA target is a contiguous sequence of an mRNA target of sufficient length to be a substrate for RNAi-directed cleavage (i.e., cleavage through a RISC pathway), dsRNAs having duplexes as short as 9 base pairs can, under some circumstances, mediate RNAi-directed RNA cleavage. Most often a target will be at least 15 nucleotides in length, preferably 15-30 nucleotides in length.

Exemplary embodiments of types of inhibitory nucleic acids can include, e.g., siRNA, shRNA, miRNA, and/or amiRNA, which are well known in the art. One skilled in the art would be able to design further siRNA, shRNA, or miRNA to target a particular nucleic acid sequence e.g., using publically available design tools, siRNA, shRNA, or miRNA is commonly made using companies such as Dharmacon (Lafayette, CO) or Sigma Aldrich (St. Louis, MO).

In some embodiments of any of the aspects, the RNA of an iRNA, e.g., a dsRNA, is chemically modified to enhance stability or other beneficial characteristics. The nucleic acids described herein may be synthesized and/or modified by methods well established in the art, such as those described in "Current protocols in nucleic acid chemistry," Beaucage, S. L. et al. (Edrs.), John Wiley & Sons, Inc., New York, NY, USA, which is hereby incorporated herein by reference. Modifications include, for example, (a) end modifications, e.g., 5' end modifications (phosphorylation, conjugation, inverted linkages, etc.) 3' end modifications (conjugation. DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Specific examples of RNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments of any of the aspects, the modified RNA will have a phosphorus atom in its internucleoside backbone.

Modified RNA backbones can include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included. Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; others having mixed N, O, S and CH2 component parts, and oligonucleosides with heteroatom backbones, and in particular —CH2-NH—CH2-, —CH2-N(CH3)-O—CH2- [known as a methylene (methylimino) or MMI backbone], —CH2-O—N(CH3)-CH2-, —CH2-N(CH3)-N(CH3)-CH2- and —N(CH3)-CH2-CH2- [wherein the native phosphodiester backbone is represented as —O—P—O—CH2-].

In other RNA mimetics suitable or contemplated for use in iRNAs, both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen. J. et al., (2005) Nucleic Acids Research 33 (1): 439-447; Mook, OR. et al., (2007) Mol Canc Ther 6 (3): 833-843; Grunweller, A. et al., (2003) Nucleic Acids Research 31 (12): 3185-3193).

Modified RNAs can also contain one or more substituted sugar moieties. The iRNAs, e.g., dsRNAs, described herein can include one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. Exemplary suitable modifications include O[(CH2)nO]mCH3, O(CH2).nOCH3, O(CH2) nNH2, O(CH2) nCH3, O(CH2)nONH2, and O(CH2)nON [(CH2)nCH3)]2, where n and m are from 1 to about 10. In some embodiments of any of the aspects, dsRNAs include one of the following at the 2' position: C1 to C10 lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments of any of the aspects, the modification includes a 2' methoxyethoxy (2'-O—CH2CH2OCH3, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a O(CH2)2ON(CH3)2 group, also known as 2'-DMAOE, as described in examples herein below, and 2'-dimethylaminoethoxyethoxy (also known in the art as 2'-O-dimethylaminocthoxyethyl or 2'-DMAEOE), i.e., 2'-O—CH2-O—CH2-N(CH2)2, also described in examples herein below.

Other modifications include 2'-methoxy (2'-OCH3), 2'-aminopropoxy (2'-OCH2CH2CH2NH2) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide, iRNAs may also have sugar mimetics such as cyclobutyl moieties in place of the pentofuranosyl sugar.

An inhibitory nucleic acid can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Certain of these nucleobases are particularly useful for increasing the binding affinity of the inhibitory nucleic acids featured in the invention. These include 5-substituted pyrimidines, 6-azapyrimidines and N-2, N-6 and 0-6 substituted purines, including 2-aminopropyladenine, 5-propynyluracil and 5-propynylcytosine, 5-methylcytosine substitutions have been shown to increase nucleic acid duplex stability by 0.6-1.2° C. (Sanghvi. Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

The preparation of the modified nucleic acids, backbones, and nucleobases described above are well known in the art.

Another modification of an inhibitory nucleic acid featured in the invention involves chemically linking to the inhibitory nucleic acid to one or more ligands, moieties or conjugates that enhance the activity, cellular distribution, pharmacokinetic properties, or cellular uptake of the iRNA. Such moieties include but are not limited to lipid moieties such as a cholesterol moiety (Letsinger et al., Proc. Natl. Acid. Sci. USA, 1989, 86: 6553-6556), cholic acid (Manoharan et al., Biorg. Med. Chem. Let., 1994, 4: 1053-1060), a thioether, e.g., beryl-S-tritylthiol (Manoharan et al., Ann. N. Y. Acad. Sci., 1992, 660: 306-309; Manoharan et al., Biorg. Med. Chem. Let., 1993, 3: 2765-2770), a thiocholesterol (Oberhauser et al., Nucl. Acids Res., 1992, 20: 533-538), an aliphatic chain, e.g., dodecandiol or undecyl residues (Saison-Behmoaras et al., EMBO J, 1991, 10:1111-1118; Kabanov et al., FEBS Lett., 1990, 259: 327-330;

Svinarchuk et al., Biochimie, 1993, 75: 49-54), a phospholipid, e.g., di-hexadecyl-rac-glycerol or triethyl-ammonium 1,2-di-O-hexadecyl-rac-glycero-3-phosphonate (Manoharan et al., Tetrahedron Lett., 1995, 36: 3651-3654; Shea et al., Nucl. Acids Res., 1990, 18: 3777-3783), a polyamine or a polyethylene glycol chain (Manoharan et al., Nucleosides & Nucleotides, 1995, 14: 969-973), or adamantane acetic acid (Manoharan et al., Tetrahedron Lett., 1995, 36: 3651-3654), a palmityl moiety (Mishra et al., Biochim. Biophys. Acta, 1995, 1264: 229-237), or an octadecylamine or hexylaminocarbonyloxycholesterol moiety (Crooke et al., J. Pharmacol. Exp. Ther., 1996, 277: 923-937).

The term "expression" refers to the cellular processes involved in producing RNA and proteins and as appropriate, secreting proteins, including where applicable, but not limited to, for example, transcription, transcript processing, translation and protein folding, modification and processing. Expression can refer to the transcription and stable accumulation of sense (mRNA) or antisense RNA derived from a nucleic acid fragment or fragments of the invention and/or to the translation of mRNA into a polypeptide.

"Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

In some embodiments of any of the aspects, a polypeptide, nucleic acid, or cell as described herein can be engineered. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell are typically still referred to as "engineered" even though the actual manipulation was performed on a prior entity.

In some embodiments of any of the aspects, the biomolecule and/or active agent described herein is exogenous. In some embodiments of any of the aspects, the biomolecule and/or active agent described herein is ectopic. In some embodiments of any of the aspects, the biomolecule and/or active agent described herein is not endogenous.

The term "exogenous" refers to a substance present in a cell other than its native source. The term "exogenous" when used herein can refer to a nucleic acid (e.g. a nucleic acid encoding a polypeptide) or a polypeptide that has been introduced by a process involving the hand of man into a biological system such as a cell or organism in which it is not normally found and one wishes to introduce the nucleic acid or polypeptide into such a cell or organism. Alternatively, "exogenous" can refer to a nucleic acid or a polypeptide that has been introduced by a process involving the hand of man into a biological system such as a cell or organism in which it is found in relatively low amounts and one wishes to increase the amount of the nucleic acid or polypeptide in the cell or organism, e.g., to create ectopic expression or levels. In contrast, the term "endogenous" refers to a substance that is native to the biological system or cell. As used herein, "ectopic" refers to a substance that is found in an unusual location and/or amount. An ectopic substance can be one that is normally found in a given cell, but at a much lower amount and/or at a different time. Ectopic also includes substance, such as a polypeptide or nucleic acid that is not naturally found or expressed in a given cell in its natural environment.

In some embodiments, a nucleic acid as described herein is comprised by a vector. In some of the aspects described herein, a nucleic acid sequence as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

In some embodiments of any of the aspects, the vector is recombinant, e.g., it comprises sequences originating from at least two different sources. In some embodiments of any of the aspects, the vector comprises sequences originating from at least two different species. In some embodiments of any of the aspects, the vector comprises sequences originating from at least two different genes, e.g., it comprises a fusion protein or a nucleic acid encoding an expression product which is operably linked to at least one non-native (e.g., heterologous) genetic control element (e.g., a promoter, suppressor, activator, enhancer, response element, or the like).

In some embodiments of any of the aspects, the vector or nucleic acid described herein is codon-optimized, e.g., the native or wild-type sequence of the nucleic acid sequence has been altered or engineered to include alternative codons such that altered or engineered nucleic acid encodes the same polypeptide expression product as the native/wild-type sequence, but will be transcribed and/or translated at an improved efficiency in a desired expression system. In some embodiments of any of the aspects, the expression system is an organism other than the source of the native/wild-type sequence (or a cell obtained from such organism). In some embodiments of any of the aspects, the vector and/or nucleic acid sequence described herein is codon-optimized for expression in a mammal or mammalian cell, e.g., a mouse, a murine cell, or a human cell. In some embodiments of any of the aspects, the vector and/or nucleic acid sequence described herein is codon-optimized for expression in a human cell. In some embodiments of any of the aspects, the vector and/or nucleic acid sequence described herein is codon-optimized for expression in a yeast or yeast cell. In some embodiments of any of the aspects, the vector and/or nucleic acid sequence described herein is codon-optimized for expression in a bacterial cell. In some embodiments of any of the aspects, the vector and/or nucleic acid sequence described herein is codon-optimized for expression in an *E. coli* cell.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification.

As used herein, the term "viral vector" refers to a nucleic acid vector construct that includes at least one element of viral origin and has the capacity to be packaged into a viral vector particle. The viral vector can contain the nucleic acid encoding a polypeptide as described herein in place of non-essential viral genes. The vector and/or particle may be utilized for the purpose of transferring any nucleic acids into cells either in vitro or in vivo. Numerous forms of viral vectors are known in the art.

Viral vector systems which can be utilized in the present invention include, but are not limited to, (a) adenovirus vectors; (b) retrovirus vectors, e.g., lentivirus vectors, murine moloney leukemia virus, etc.; (c) adeno-associated virus vectors; (d) herpes simplex virus vectors; (e) SV40 vectors; (f) polyoma virus vectors; (g) papilloma virus vectors; (h) picornavirus vectors; (i) pox virus vectors such as an orthopox, e.g., vaccinia virus vectors or avipox, e.g., canary pox or fowl pox; and (j) a helper-dependent or gutless adenovirus. Replication-defective viruses can also be advantageous. In some embodiments, the vector is an adeno-associated virus vector.

In some embodiments, a viral vector such as an adeno-associated virus (AAV) vector is used. AAVs, which normally infect mammals, including humans, but are non-pathogenic, have been developed and employed as gene therapy vectors in clinical trials in the United States and Europe (Daya and Berns, Clinical Microbiology Reviews 2008, 21, 583-593). AAV vectors may be prepared using any one of a number of methods available to those of ordinary skill in the art. Exemplary AAV vectors are disclosed in Walsh et al., Proc. Soc. Exp. Biol. Med. 204: 289-300 (1993); U.S. Pat. No. 5,436,146 which is incorporated herein by reference; Gao et al., Gene Therapy 2005, 5, 285-297; Vandenberghe et al., Gene Therapy 2009, 16, 311-319; Gao et al., PNAS 2002, 99, 11854-11859; Gao et al., PNAS 2003, 100, 6081-6086; Gao et al., J. of Virology 2004, 78, 6381-6388.

In some embodiments, the vector is an adeno-associated virus (AAV) vector. In some embodiments, the AAV vector is an AAV1, AAV2, AAV4, AAV5, AAV6, AAV7, AAV8, AAV9, AAV9.HR, AAVrh.10, AAVMYO, or AAV2.5. In some embodiments, the AAV is AAV9.

It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

As non-limiting examples, in some embodiments, a plasmid expression vector can be used. Plasmid expression vectors include, but are not limited to, pcDNA3.1, pET vectors (Novagen®), pGEX vectors (GE Life Sciences), and pMAL vectors (New England labs, Inc.) for protein expression in *E. coli* host cell such as BL21, BL21 (DE3) and AD494(DE3)pLysS, Rosetta (DE3), and Origami(DE3) (Novagen®); the strong CMV promoter-based pcDNA3.1 (Invitrogen™ Inc.) and pCIneo vectors (Promega) for expression in mammalian cell lines such as CHO, COS, HEK-293, Jurkat, and MCF-7; replication incompetent adenoviral vector vectors pAdeno X, pAd5F35, pLP-Adeno-X-CMV (Clontech®), pAd/CMV/V5-DEST, pAd-DEST vector (Invitrogen™ Inc.) for adenovirus-mediated gene transfer and expression in mammalian cells; pLNCX2, pLXSN, and pLAPSN retrovirus vectors for use with the Retro-X™ system from Clontech for retroviral-mediated gene transfer and expression in mammalian cells; pLenti4/V5-DEST™, pLenti6/V5-DEST™, and pLenti6.2/V5-GW/lacZ (INVITROGEN™ Inc.) for lentivirus-mediated gene transfer and expression in mammalian cells; adenovirus-associated virus expression vectors such as pAAV-MCS, pAAV-IRES-hrGFP, and pAAV-RC vector (Stratagene®) for adeno-associated virus-mediated gene transfer and expression in mammalian cells.

A retroviral vector can also be used (see Miller et al., Meth. Enzymol. 217: 581-599 (1993)). These retroviral vectors contain the components necessary for the correct packaging of the viral genome and integration into the host cell DNA. In another embodiment, the vector is a pox virus such as a vaccinia virus, for example an attenuated vaccinia such as Modified Virus Ankara (MVA) or NYVAC, an avipox such as fowl pox or canary pox. In another embodiment, lentiviral vectors are used, such as the HIV based vectors described in U.S. Pat. Nos. 6,143,520; 5,665,557; and 5,981,276, which are herein incorporated by reference. The vector may or may not be incorporated into the genome of a cell. The constructs may include viral sequences for transfection, if desired. Alternatively, the vector can be capable of episomal replication, e.g., EPV and EBV vectors.

As used herein, "viral particle" refers to a particle comprising at least one viral capsid polypeptide and a nucleic acid molecule, e.g., a viral genome and/or viral vector. Viral vectors are discussed elsewhere herein.

As used herein, "antiviral" refers to any chemical or biological agent with therapeutic usefulness in the inhibition of viral transmission, activity, or replication. Categories of antivirals can include, but are not limited to entry inhibitors, uncoating inhibitors, viral synthesis inhibitors, assembly inhibitors, and release inhibitors. Exemplary, non-limiting antivirals include enfuvirtide, amantadine, rimantadine, pleconaril, acyclovir, zidovudine, lamivudine, fomivirsen, rifampicin, zanamivir, oseltamivir, peramivir, abacavir, acyclovir, adefovir, amprenavir, baloxavir marboxil, boceprevir, cobicistat, combivir, daclatasvir, doravirine, etravirine, ganciclovir, ibalizumab, letermovir, rilpivirine, simeprevir, telbivudine, and valciclovir. One of skill in the art can readily identify an antiviral agent of use e.g. see Antiviral Drugs. Wieslaw M. Kazmierski (ed.) Wiley and Sons (2011); Antiviral Drugs, John S. Driscoll. Wiley and Sons (2005); each of which is incorporated by reference herein in its entirety.

As used herein, "antibiotic" refers to any chemical or biological agent with therapeutic usefulness in the inhibition of bacterial cell growth or in killing bacteria, e.g. those that are bactericidal or bacteriostatic. Categories of antibiotics can include, but are not limited to those that target the bacterial cell wall (e.g., penicillins, cephalosporins), those that target the bacterial cell membrane (e.g., polymyxins), those that target bacterial enzymes (e.g., rifamycins, lipiarmycins, quinolones, sulfonamides), protein synthesis inhibitors (e.g., macrolides, lincosamides, and tetracyclines), aminoglycosides, cyclic lipopeptides, glycyclines, oxazolidinones, beta-lactams, and lipiarmycins. Exemplary, non-limiting antibiotics include penicillin, methicilling, nafcillin, oxacillin, cloxacillin, dicloxacillin, flucloxacillin, ampicillin, amoxicillin, pivampicillin, hetacillin, bacampicillin, metampicillin, talamipicillin, epicillin, cabenicillin, ticaricillin, temocillin, mezlocillin, piperacillin, azolocillin, clavulanic acid, sulbactam, tazobactam, cafadroxil, cephalexin, cefalotin, cefapirin, cefazolin, cefradine, cefaclor, cefonicid, cefprozil, cefuroxime, loracarbef, cefmetazole, cefotetan, cefoxitin, cefotiam, cefdinir, cefixime, cefotaxime, cefovecin, cefpodoxime, ceftibuten, ceftiofur, ceftizoxime, ceftriaxone, cefoperazone, ceftazimdime, latamoxef, cefepime, cefiderocol, cefpriome, rifampicin, rifabutin, rifapentine, rifamixin, fidaxomicin, ciproflaxicin, moxifloxacin, levofloxacin, sulfafurzole, azithromycin, clarithromycin, erythromycin, fidaxomicin, spiramycin, telihtromycin, lincomycin, clindamycin, pirlimycin, tetracycline, cravacycline, sarecycline, omadacycline, doxycycline, kanamycin, tobramycin, gentamicin, neomycin, streptomycin, vancomycin, tigecycline, linezolid, posizolid, tedizolid, radezolid, cycloserine, contezolid, and daptomycin. One of skill in the art can readily identify an antibiotic agent of use e.g. see Antibiotics in Laboratory Medicine, Victor Lorian (ed.) Wolters Kluwer; and Antibiotics Manual, David Schlossberg and Rafik Samuel, John Wiley and Sons (2017); each of which is incorporated by reference herein in its entirety.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments of any of the aspects, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies. Fab and sFab fragments, F(ab')2. Fd fragments. Fv fragments, scFv, and domain antibodies (dAb) fragments as well as complete antibodies.

As used herein, the term "antibody" refers to immunoglobulin molecules and immunologically active portions of immunoglobulin molecules, i.e., molecules that contain an antigen binding site that immunospecifically binds an antigen. The term also refers to antibodies comprised of two immunoglobulin heavy chains and two immunoglobulin light chains as well as a variety of forms including full length antibodies and antigen-binding portions thereof; including, for example, an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody (dAb), a diabody, a multispecific antibody, a dual specific antibody, an anti-idiotypic antibody, a bispecific antibody, a functionally active epitope-binding portion thereof, and/or bifunctional hybrid antibodies. Each heavy chain is composed of a variable region of said heavy chain (abbreviated here as HCVR or VH) and a constant region of said heavy chain. The heavy chain constant region consists of three domains CH1, CH2 and CH3. Each light chain is composed of a variable region of said light chain (abbreviated here as LCVR or VL) and a constant region of said light chain. The light chain constant region consists of a CL domain. The VH and VL regions may be further divided into hypervariable regions referred to as complementarity-determining regions (CDRs) and interspersed with conserved regions referred to as framework regions (FR). Each VH and VL region thus consists of three CDRs and four FRs which are arranged from the N terminus to the C terminus in the following order: FR1, CDR1, FR2, CDR2, FR3, CDR3, FR4. This structure is well known to those skilled in the art.

Antibodies and/or antibody reagents can include an immunoglobulin molecule, a monoclonal antibody, a chimeric antibody, a CDR-grafted antibody, a humanized antibody, a fully human antibody, a Fab, a Fab', a F(ab')2, a Fv, a disulfide linked Fv, a scFv, a single domain antibody, a diabody, a multispecific antibody, a dual specific antibody, an anti-idiotypic antibody, a bispecific antibody, and a functionally active epitope-binding portion thereof.

As used herein, the term "nanobody" or single domain antibody (sdAb) refers to an antibody comprising the small single variable domain (VHH) of antibodies obtained from camelids and dromedaries. Antibody proteins obtained from members of the camel and dromedary (*Camelus baclrianus* and *Camelus dromedarius*) family including new world members such as llama species (*Lama paccos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. Sec PCT/EP93/02214 (WO 94/04678 published 3 Mar. 1994; which is incorporated by reference herein in its entirety).

A region of the camelid antibody which is the small single variable domain identified as VHH can be obtained by genetic engineering to yield a small protein having high affinity for a target, resulting in a low molecular weight antibody-derived protein known as a "camelid nanobody". Sec U.S. Pat. No. 5,759,808 issued Jun. 2, 1998; see also Stijlemans. B. et al., 2004 J Biol Chem 279: 1256-1261; Dumoulin, M. et al., 2003 Nature 424: 783-788; Pleschberger, M. et al. 2003 Bioconjugate Chem 14: 440-448; Cortez-Retamozo, V. et al. 2002 Int J Cancer 89: 456-62; and Lauwereys, M. et al. 1998 EMBO J. 17: 3512-3520; each of which is incorporated by reference herein in its entirety. Engineered libraries of camelid antibodies and antibody fragments are commercially available, for example, from Ablynx, Ghent, Belgium. As with other antibodies of non-human origin, an amino acid sequence of a camelid antibody can be altered recombinantly to obtain a sequence that more closely resembles a human sequence, i.e., the nanobody can be "humanized". Thus the natural low antigenicity of camelid antibodies to humans can be further reduced.

The camelid nanobody has a molecular weight approximately one-tenth that of a human IgG molecule and the protein has a physical diameter of only a few nanometers. One consequence of the small size is the ability of camelid nanobodies to bind to antigenic sites that are functionally invisible to larger antibody proteins, i.e., camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody. The low molecular weight and compact size further result in camelid nanobodies being extremely thermostable, stable to extreme pH and to proteolytic digestion, and poorly antigenic. See U.S. patent application No. 20040161738 published Aug. 19, 2004; which is incorporated by reference herein in its entirety. These features combined with the low antigenicity to humans indicate great therapeutic potential.

Immune checkpoint inhibitors inhibit one or more immune checkpoint proteins. The immune system has multiple inhibitory pathways that are critical for maintaining self-tolerance and modulating immune responses. For example, in T-cells, the amplitude and quality of response is initiated through antigen recognition by the T-cell receptor and is regulated by immune checkpoint proteins that balance co-stimulatory and inhibitory signals. In some embodiments of any of the aspects, a subject or patient is treated with at least one inhibitor of an immune checkpoint protein. As used herein, "immune checkpoint protein" refers to a protein which, when active, exhibits an inhibitory effect on immune activity, e.g., T cell activity. Exemplary immune checkpoint proteins can include PD-1 (e.g., NCBI Gene ID: 5133); PD-L1 (e.g., NCBI Gene ID: 29126); PD-L2 (e.g., NCBI Gene ID: 80380); TIM-3 (e.g., NCBI Gene ID: 84868); CTLA4 (e.g., NCBI Gene ID: 1493); TIGIT (e.g., NCBI Gene ID: 201633); KIR (e.g., NCBI Gene ID: 3811); LAG3 (e.g., NCBI Gene ID: 3902); DD1-α (e.g., NCBI Gene ID: 64115); A2AR (e.g., NCBI Gene ID: 135); B7-H3 (e.g., NCBI Gene ID: 80381); B7-H4 (e.g., NCBI Gene ID: 79679); BTLA (e.g., NCBI Gene ID: 151888); IDO (e.g., NCBI Gene ID: 3620); TDO (e.g., NCBI Gene ID: 6999); HVEM (e.g., NCBI Gene ID: 8764); GAL9 (e.g., NCBI Gene ID: 3965); 2B4 (belongs to the CD2 family of molecules and is expressed on all NK, γδ, and memory CD8+ (αβ) T cells) (e.g., NCBI Gene ID: 51744); CD160 (also referred to as BY55) (e.g., NCBI Gene ID: 11126); and various B-7 family ligands. B7 family ligands include, but are not limited to, B7-1, B7-2, B7-DC, B7-H1, B7-H2, B7-H3, B7-H4, B7-H5, B7-H6 and B7-H7.

Non-limiting examples of immune checkpoint inhibitors (with checkpoint targets and manufacturers noted in parentheses) can include: MGA271 (B7-H3: MacroGenics); ipilimumab (CTLA-4; Bristol Meyers Squibb); pembrolizumab (PD-1; Merck); nivolumab (PD-1; Bristol Meyers Squibb); atezolizumab (PD-L1; Genentech); galiximab (B7.1; Biogen); IMP321 (LAG3: Immuntep); BMS-986016 (LAG3; Bristol Meyers Squibb); SMB-663513 (CD137; Bristol-Meyers Squibb); PF-05082566 (CD137; Pfizer); IPH2101 (KIR; Innate Pharma); KW-0761 (CCR4; Kyowa Kirin); CDX-1127 (CD27; CellDex); MEDI-6769 (Ox40); MedImmune); CP-870,893 (CD40; Genentech); tremelimumab (CTLA-4; Medimmune); pidilizumab (PD-1; Medivation); MPDL3280A (PD-L1; Roche); MEDI4736 (PD-L1; AstraZeneca); MSB0010718C (PD-L1; EMD Serono); AUNP12 (PD-1; Aurigene); avelumab (PD-L1; Merck); durvalumab (PD-L1; Medimmune); IMP321, a soluble Ig fusion protein (Brignone et al., 2007, J. Immunol. 179: 4202-4211); the anti-B7-H3 antibody MGA271 (Loo et al., 2012, Clin. Cancer Res. July 15 (18) 3834); TIM3 (T-cell immunoglobulin domain and mucin domain 3) inhibitors (Fourcade et al., 2010, J. Exp. Med. 207:2175-86 and Sakuishi et al., 2010, J. Exp. Med. 207:2187-94); anti-CTLA-4 antibodies described in U.S. Pat. Nos. 5,811,097; 5,811,097; 5,855,887; 6,051,227; 6,207,157; 6,682,736; 6,984,720; and 7,605,238; tremelimumab, (ticilimumab, CP-675.206); ipilimumab (also known as 10D1, MDX-D010); PD-1 and PD-L1 blockers described in U.S. Pat. Nos. 7,488,802; 7,943,743; 8,008,449; 8,168,757; 8,217, 149, and PCT Published Patent Application Nos: WO03042402, WO2008156712, WO2010089411, WO2010036959, WO2011066342, WO2011159877, WO2011082400, and WO2011161699; nivolumab (MDX 1106, BMS 936558, ONO 4538); lambrolizumab (MK-3475 or SCH 900475); CT-011; AMP-224; and BMS-936559 (MDX-1105-01). The foregoing references are incorporated by reference herein in their entireties.

In some embodiments of any of the aspects, the biomolecule and/or active agent can be a therapeutic compound or drug, e.g., an agent or compound which is therapeutically effective for the treatment of at least one condition in a subject. Therapeutic compounds are known in the art for a variety of conditions, see, e.g., the database available on the world wide web at drugs.com or the catalog of FDA-approved compounds available on the world wide web at catalog.data.gov/dataset/drugsfda-database; each of which is incorporated by reference herein in its entirety.

As used herein the term "chemotherapeutic agent" refers to any chemical or biological agent with therapeutic usefulness in the treatment of diseases characterized by abnormal cell growth. Such diseases include tumors, neoplasms and cancer as well as diseases characterized by hyperplastic growth. These agents can function to inhibit a cellular activity upon which the cancer cell depends for continued proliferation. In some aspect of all the embodiments, chemotherapeutic agent is a cell cycle inhibitor or a cell division inhibitor. Categories of chemotherapeutic agents that are useful in the methods of the invention include alkylating/alkaloid agents, antimetabolites, hormones or hormone analogs, and miscellaneous antineoplastic drugs. Most of these agents are directly or indirectly toxic to cancer cells. In one embodiment, a chemotherapeutic agent is a radioactive molecule. One of skill in the art can readily identify a chemotherapeutic agent of use (e.g. see Physicians' Cancer Chemotherapy Drug Manual 2014. Edward Chu. Vincent T. De Vita Jr., Jones & Bartlett Learning; Principles of Cancer Therapy, Chapter 85 in Harrison's Principles of Internal Medicine, 18th edition; Therapeutic Targeting of Cancer Cells: Era of Molecularly Targeted Agents and Cancer Pharmacology, Chs. 28-29 in Abeloff's Clinical Oncology, 2013 Elsevier; and Fischer D S (ed): The Cancer Chemotherapy Handbook, 4th ed. St. Louis, Mosby-Year Book, 2003).

Exemplary chemotherapeutics include an anthracycline (e.g., doxorubicin (e.g., liposomal doxorubicin)), a vinca alkaloid (e.g., vinblastine, vincristine, vindesine, vinorelbine), an alkylating agent (e.g., cyclophosphamide, decarbazine, melphalan, ifosfamide, temozolomide), an antibody (e.g., alemtuzamab, bevacizumab (Avastin®), gemtuzumab, nivolumab (Opdivo®), pembrolizumab (Keytruda®), rituximab (Rituxan®), traztuzumab (Herceptin®) tositumomab), an antimetabolite (including, e.g., folic acid antagonists, pyrimidine analogs, purine analogs and adenosine deaminase inhibitors (e.g., fludarabine)), an mTOR inhibitor, a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide (Revlimid®)), a kinase inhibitor (e.g., palbociclib (Ibrance®), or a hormone therapy (e.g., abiraterone acetate (Zytiga®)). General chemotherapeutic agents include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®, Etopophos®, Toposar®), fludarabine phosphate (Fludara®), 5-fluorouracil (Adrucil®, Efudex®), flutamide (Eulexin®), tezacitibine, gemcitabine (difluorodeoxy citidine), hydroxyurea (Hydrea®), ibrutinib (Imbruvica®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90)/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®). Exemplary alkylating agents include, without limitation, nitrogen mustards, ethylenimine derivatives, alkyl sulfonates, nitrosoureas and triazenes); uracil mustard (Aminouracil Mustard®, Chlorethaminacil®, Demethyldopan®, Desmethyldopan®, Haemanthamine®, Nordopan®, Uracil Nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®. Procytox®, Revimmune™), ifosfamide (Mitoxana®), melphalan (Alkeran®). Chlorambucil (Leukeran®), pipobroman (Amedel®, Vercyte®), triethylenemelamine (Hemel®, Hexalen®, Hexastat®), triethylenethiophosphoramine. Temozolomide (Temodar®), thiotepa (Thioplex®, Tepadina®), busulfan (Busilvex®, Myleran®), improsulfan, piposulfan, carmustine (BiCNU®), lomustine (CeeNU®), streptozocin (Zanosar®), and Dacarbazine (DTIC-Dome®). Additional exemplary alkylating agents include, without limitation. Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex®; and Myleran®); carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®). Exemplary mTOR inhibitors include, e.g., temsirolimus; ridaforolimus (formally known as deforolimus, (1R,2R,45)-4-[(2R)-2 [(1R,95,125,15R,16E,18R,19R,21R,235,24E,26E,28Z,305, 325,35R)-1,18-dihydroxy-19,30-dimethoxy-15,17,21,23, 29,35-hexamethyl-2,3,10,14,20-pentaoxo-11,36-dioxa-4-azatricyclo[30.3.1.04'9]hexatriaconta-16,24,26,28-tetraen-12-yl]propyl]-2-methoxycyclohexyl dimethylphosphinate, also known as AP23573 and MK8669, and described in PCT Publication No. WO 03/064383); everolimus (Afinitor® or RAD001); rapamycin (AY22989, Sirolimus®); simapimod (CAS 164301-51-3); emsirolimus, (5-{2,4-Bis[(3S,)-3-methylmorpholin-4-yl]pyrido[2,3-(i]pyrimidin-7-yl}-2-methoxyphenyl)methanol (AZD8055); 2-Amino-8-[iraw5-4-(2-hydroxyethoxy)cyclohexyl]-6-(6-methoxy-3-pyridinyl)-4-methyl-pyrido[2,3-JJpyrimidin-7(8H)-one (PF04691502, CAS 1013101-36-4); and N2-[1,4-dioxo-4-[[4-(4-oxo-8-phenyl-4H-1-benzopyran-2-yl)morpholinium-4-yl]methoxy]butyl]-L-arginylglycyl-L-a-aspartyIL-serine-, inner salt (SF1126, CAS 936487-67-1), and XL765. Exemplary immunomodulators include, e.g., afutuzumab (available from Roche®); pegfilgrastim (Neulasta®); lenalidomide (CC-5013, Revlimid®); thalidomide (Thalomid®), actimid (CC4047); and IRX-2 (mixture of human cytokines including interleukin 1, interleukin 2, and interferon γ, CAS 951209-71-5, available from IRX Therapeutics). Exemplary anthracyclines include, e.g., doxorubicin (Adriamycin® and Rubex®); bleomycin (Lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin. Exemplary vinca alkaloids include, e.g., vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®). Exemplary proteosome inhibitors include bortezomib (Velcade®); carfilzomib (PX-171-007, (5)-4-Methyl-N-((5)-1-(((5)-4-methyl-1-((R)-2-methyloxiran-2-yl)-1-oxopentan-2-yl)amino)-1-oxo-3-phenylpropan-2-yl)-2-((5,)-2-(2-morpholinoacetamido)-4-phenylbutanamido)-pentanamide); marizomib (NPT0052); ixazomib citrate (MLN-9708); delanzomib (CEP-18770); and O-Methyl-N-[(2-methyl-5-thiazolyl)carbonyl]-L-seryl-O-methyl-N-[(11S')-2-[(2R)-2-methyl-2-oxiranyl]-2-oxo-1-(phenylmethyl)ethyl]-L-serinamide (ONX-0912). Additional exemplary anti-cancer agents also include AMG479, vorinostat, ABT-737, PI-103; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1l (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE®, vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, ameliora- tion or palliation of the disease state, remission (whether partial or total), and/or decreased mortality, whether detect- able or undetectable. The term "treatment" of a disease also includes providing relief from the symptoms or side-effects of the disease (including palliative treatment).

In some embodiments of any of the aspects, described herein is a prophylactic method of treatment. As used herein "prophylactic" refers to the timing and intent of a treatment relative to a disease or symptom, that is, the treatment is administered prior to clinical detection or diagnosis of that particular disease or symptom in order to protect the patient from the disease or symptom. Prophylactic treatment can encompass a reduction in the severity or speed of onset of the disease or symptom, or contribute to faster recovery from the disease or symptom. In some embodiments of any of the aspects, prophylactic treatment is not prevention of all symptoms or signs of a disease.

As used herein, the term "pharmaceutical composition" refers to the active agent in combination with a pharmaceu- tically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a rea- sonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or oint- ment. In some embodiments of any of the aspects, a phar- maceutically acceptable carrier can be an artificial or engi- neered carrier, e.g., a carrier that the active ingredient would not be found to occur in in nature.

As used herein, the term "administering," refers to the placement of a compound as disclosed herein into a subject by a method or route which results in at least partial delivery of the agent at a desired site. Pharmaceutical compositions comprising the compounds disclosed herein can be admin- istered by any appropriate route which results in an effective treatment in the subject. In some embodiments, administra- tion comprises physical human activity, e.g., an injection, act of ingestion, an act of application, and/or manipulation of a delivery device or machine. Such activity can be performed, e.g., by a medical professional and/or the subject being treated.

As used herein, "contacting" refers to any suitable means for delivering, or exposing, an agent to at least one cell. Exemplary delivery methods include, but are not limited to, direct delivery to cell culture medium, perfusion, injection, or other delivery method well known to one skilled in the art. In some embodiments, contacting comprises physical human activity, e.g., an injection; an act of dispensing, mixing, and/or decanting; and/or manipulation of a delivery device or machine.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional charac- teristic(s) of that embodiment of the invention.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the con- ditions of the assay being utilized.

The singular terms "a," "an," and "the" include plural referents unless context clearly indicates otherwise. Simi- larly, the word "or" is intended to include "and" unless the context clearly indicates otherwise. Although methods and materials similar or equivalent to those described herein can be used in the practice or testing of this disclosure, suitable methods and materials are described below. The abbrevia- tion, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limi- tations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfill- ing the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodi- ments only, and is not intended to limit the scope of the present invention, which is defined solely by the claims. Definitions of common terms in immunology and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology. Elsevier Science Publishing, Inc., New York, USA (2012) (ISBN 044460149X); Laboratory Methods in Enzymology: DNA, Jon Lorsch (cd.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan. ADA M Kruisbeck. David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Other terms are defined herein within the description of the various aspects of the invention.

All patents and other publications; including literature references, issued patents, published patent applications, and co-pending patent applications: cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

In some embodiments, the present technology may be defined in any of the following numbered paragraphs:

1. A functionalizing nanocomplex comprising:
   a. one or more polyphenol molecules; and
   b. one or more biomolecules.
2. The nanocomplex of any of the preceding paragraphs, wherein the one or more polyphenols collectively comprise at least one galloyl moiety and/or at least one catechol moiety.
3. The nanocomplex of any of the preceding paragraphs, wherein the one or more polyphenols collectively comprise at least one galloyl moiety and at least one catechol moiety.
4. The nanocomplex of any of the preceding paragraphs, wherein the one or more polyphenols each comprise at least one galloyl moiety and at least one catechol moiety.
5. The nanocomplex of any of the preceding paragraphs, wherein the polyphenol is tannic acid.
6. The nanocomplex of any of the preceding paragraphs, wherein the stoichiometric ratio of polyphenol molecules to biomolecules is 570 or less relative polyphenol.
7. The nanocomplex of any of the preceding paragraphs, wherein the stoichiometric ratio of tannic acid molecules to biomolecules is 190 to 570.
8. The nanocomplex of any of the preceding paragraphs, wherein the stoichiometric ratio of tannic acid molecules to biomolecules is 190.
9. The nanocomplex of any of the preceding paragraphs, wherein the biomolecule and/or active agent is a nucleic acid, protein, viral particle, alkaloid, polysaccharide, anthocyanin, lipid, antiviral drug, antibiotic, chemotherapeutic, or combination thereof.
10. The nanocomplex of paragraph 9, wherein the biomolecule and/or active agent comprises or is a protein.
11. The nanocomplex of paragraph 10, wherein the biomolecule and/or active agent is ovalbumin, serum albumin, interleukin-4, an antibody or antibody reagent, cholera toxin subunit B, biotin, cytokine, or lectin.
12. The nanocomplex of paragraph 11, wherein the antibody or antibody reagent is specific for an immune checkpoint protein.
13. A functionalized mammalian cell comprising at least one functionalizing nanocomplex of any of paragraphs 1-12, wherein the at least one functionalizing nanocomplex is adhered to the surface of the cell.
14. The cell of paragraph 13, wherein the cell is a hematopoietic cell.
15. The cell of paragraph 13, wherein the cell is an erythrocyte, T cell, monocyte, macrophage, neutrophil or natural killer cell.
16. The cell of any of paragraphs 13-14, wherein the biomolecule and/or active agent is an antibody or antibody reagent specific for an immune checkpoint protein and the cell is a macrophage.
17. The cell of any of paragraphs 13-14, wherein the biomolecule and/or active agent is an antibody or antibody reagent, cytokine, antiviral drug, antibiotic, or siRNA and the cell is a erythrocyte.

18. The cell of any of paragraphs 13-14, wherein the biomolecule and/or active agent is an antibody or antibody reagent, siRNA, or chemotherapeutic and the cell is a natural killer cell.

19. The cell of any of paragraphs 13-14, wherein the biomolecule and/or active agent is cytokine and the cell is a T cell.

20. The cell of any of paragraphs 13-14, wherein the biomolecule and/or active agent is an anti-inflammatory drug and the cell is a neutrophil.

21. The cell of any of paragraphs 13-20, wherein functionalizing nanocomplexes collectively comprising 10 to 1 trillion biomolecules are adhered to the surface of the cell.

22. A method of functionalizing a mammalian cell, the method comprising:
   a. combining one or more polyphenol molecules and one or more biomolecules; and
   b. contacting a mammalian cell with the combination resulting from step a;
   whereby a functionalizing nanocomplex forms and adheres to the surface of the cell.

23. The method of any of the preceding paragraphs, wherein the one or more polyphenols collectively comprise at least one galloyl moiety and/or at least one catechol moiety.

24. The method of any of the preceding paragraphs, wherein the one or more polyphenols collectively comprise at least one galloyl moiety and at least one catechol moiety.

25. The method of any of the preceding paragraphs, wherein the one or more polyphenols each comprise at least one galloyl moiety and at least one catechol moiety.

26. The method of any of the preceding paragraphs, wherein the polyphenol is tannic acid.

27. The method of any of the preceding paragraphs, wherein the stoichiometric ratio of polyphenol molecules to biomolecules is 570 or less relative polyphenol.

28. The method of any of the preceding paragraphs, wherein the stoichiometric ratio of polyphenol molecules to biomolecules is 190 to 570.

29. The method of any of the preceding paragraphs, wherein the stoichiometric ratio of polyphenol molecules to biomolecules is 190.

30. The method of any of the preceding paragraphs, wherein the biomolecule and/or active agent is a nucleic acid, protein, viral particle, alkaloid, polysaccharide, anthocyanin, lipid, antiviral drug, antibiotic, chemotherapeutic, or combination thereof.

31. The method of paragraph 30, wherein the biomolecule and/or active agent comprises or is a protein.

32. The method of paragraph 31, wherein the biomolecule and/or active agent is ovalbumin, serum albumin, interleukin-4, an antibody or antibody reagent, cholera toxin subunit B, biotin, cytokine, or lectin.

33. The method of paragraph 32, wherein the antibody or antibody reagent is specific for an immune checkpoint protein.

34. A method of administering a biomolecule and/or active agent to a patient in need of treatment with the biomolecule, the method comprising administering a cell of any of paragraphs 13-16 to the patient.

35. The method of paragraph 34, wherein the cell is autologous to the patient.

36. The method of any of paragraphs 34-35, wherein the cell is a erythrocyte and a plurality of the biomolecule and/or active agent administered to the patient is delivered to the lungs.

37. The method of any of paragraphs 34-35, wherein the cell is a macrophage and a plurality of the biomolecule and/or active agent administered to the patient is delivered to the brain, a tumor, or a site of inflammation or autoimmune inflammation.

38. The method of any of paragraphs 34-35, wherein the cell is a natural killer cell and a plurality of the biomolecule and/or active agent administered to the patient is delivered to a tumor.

39. The method of any of paragraphs 34-35, wherein the cell is a T cell and a plurality of the biomolecule and/or active agent administered to the patient is delivered to a tumor.

40. The method of any of paragraphs 34-35, wherein the cell is a neutrophil and a plurality of the biomolecule and/or active agent administered to the patient is delivered to the lungs or a site of inflammation.

41. A functionalized cell of any of paragraphs 13-16, for use in a method of administering a biomolecule and/or active agent to a patient in need of treatment with the biomolecule, the method comprising administering the functionalized cell to the patient.

42. The cell of paragraph 41, wherein the cell is autologous to the patient.

43. The cell of any of paragraphs 41-42, wherein the cell is a erythrocyte and a plurality of the biomolecule and/or active agent administered to the patient is delivered to the lungs.

44. The cell of any of paragraphs 41-42, wherein the cell is a macrophage and a plurality of the biomolecule and/or active agent administered to the patient is delivered to the brain, a tumor, or a site of inflammation or autoimmune inflammation.

45. The cell of any of paragraphs 41-42, wherein the cell is a natural killer cell and a plurality of the biomolecule and/or active agent administered to the patient is delivered to a tumor.

46. The cell of any of paragraphs 41-42, wherein the cell is a T cell and a plurality of the biomolecule and/or active agent administered to the patient is delivered to a tumor.

47. The cell of any of paragraphs 41-42, wherein the cell is a neutrophil and a plurality of the biomolecule and/or active agent administered to the patient is delivered to the lungs or a site of inflammation.

In some embodiments, the present technology may be defined in any of the following numbered paragraphs:

1. A functionalizing nanocomplex comprising:
   a) one or more polyphenol molecules; and
   b) one or more biomolecules.

2. The nanocomplex of any of the preceding paragraphs, wherein the one or more polyphenols collectively comprise at least one galloyl moiety and/or at least one catechol moiety.

3. The nanocomplex of any of the preceding paragraphs, wherein the one or more polyphenols collectively comprise at least one galloyl moiety and at least one catechol moiety.

4. The nanocomplex of any of the preceding paragraphs, wherein the one or more polyphenols each comprise at least one galloyl moiety and at least one catechol moiety.

5. The nanocomplex of any of the preceding paragraphs, wherein the polyphenol is tannic acid.

6. The nanocomplex of any of the preceding paragraphs, wherein the stoichiometric ratio of polyphenol molecules to biomolecules is 570 or less relative polyphenol.

7. The nanocomplex of any of the preceding paragraphs, wherein the stoichiometric ratio of tannic acid molecules to biomolecules is 190 to 570.

8. The nanocomplex of any of the preceding paragraphs, wherein the stoichiometric ratio of tannic acid molecules to biomolecules is 190.

9. The nanocomplex of any of the preceding paragraphs, wherein the biomolecule and/or active agent is a nucleic acid, protein, a viral particle, a viral vector, alkaloid, polysaccharide, anthocyanin, lipid, antiviral drug, antibiotic, chemotherapeutic, or combination thereof.

10. The nanocomplex of paragraph 9, wherein the biomolecule and/or active agent comprises or is a protein.

11. The nanocomplex of paragraph 10, wherein the biomolecule and/or active agent is ovalbumin, serum albumin, interleukin-4, an antibody or antibody reagent, cholera toxin subunit B, biotin, cytokine, or lectin.

12. The nanocomplex of paragraph 11, wherein the antibody or antibody reagent is specific for an immune checkpoint protein.

13. The nanocomplex of paragraph 9, wherein the biomolecule and/or active agent is a viral particle to viral vector.

14. The nanocomplex of paragraph 13, wherein the viral particle or viral vector is an adeno-associated virus vector.

15. The nanocomplex of paragraph 14, wherein the adeno-associated virus vector is AAV9.

16. A functionalized mammalian cell comprising at least one functionalizing nanocomplex of any of paragraphs 1-15, wherein the at least one functionalizing nanocomplex is adhered to the surface of the cell.

17. The cell of paragraph 16, wherein the cell is a hematopoietic cell.

18. The cell of paragraph 16, wherein the cell is an erythrocyte, T cell, monocyte, macrophage, neutrophil or natural killer cell.

19. The cell of any of paragraphs 16-18, wherein the biomolecule and/or active agent is an antibody or antibody reagent specific for an immune checkpoint protein and the cell is a macrophage.

20. The cell of any of paragraphs 16-18, wherein the biomolecule and/or active agent is an antibody or antibody reagent, cytokine, antiviral drug, antibiotic, viral particle, viral vector, or siRNA and the cell is a erythrocyte.

21. The cell of any of paragraphs 16-18, wherein the biomolecule and/or active agent is an antibody or antibody reagent, siRNA, or chemotherapeutic and the cell is a natural killer cell.

22. The cell of any of paragraphs 16-18, wherein the biomolecule and/or active agent is cytokine and the cell is a T cell.

23. The cell of any of paragraphs 16-18, wherein the biomolecule and/or active agent is an anti-inflammatory drug and the cell is a neutrophil.

24. The cell of any of paragraphs 16-23, wherein functionalizing nanocomplexes collectively comprising 10 to 1 trillion biomolecules are adhered to the surface of the cell.

25. A method of functionalizing a mammalian cell, the method comprising:
   a) combining one or more polyphenol molecules and one or more biomolecules; and
   b) contacting a mammalian cell with the combination resulting from step a;
   whereby a functionalizing nanocomplex forms and adheres to the surface of the cell.

26. The method of any of the preceding paragraphs, wherein the one or more polyphenols collectively comprise at least one galloyl moiety and/or at least one catechol moiety.

27. The method of any of the preceding paragraphs, wherein the one or more polyphenols collectively comprise at least one galloyl moiety and at least one catechol moiety.

28. The method of any of the preceding paragraphs, wherein the one or more polyphenols each comprise at least one galloyl moiety and at least one catechol moiety.

29. The method of any of the preceding paragraphs, wherein the polyphenol is tannic acid.

30. The method of any of the preceding paragraphs, wherein the stoichiometric ratio of polyphenol molecules to biomolecules is 570 or less relative polyphenol.

31. The method of any of the preceding paragraphs, wherein the stoichiometric ratio of polyphenol molecules to biomolecules is 190 to 570.

32. The method of any of the preceding paragraphs, wherein the stoichiometric ratio of polyphenol molecules to biomolecules is 190.

33. The method of any of the preceding paragraphs, wherein the biomolecule and/or active agent is a nucleic acid, protein, viral particle, viral vector, alkaloid, polysaccharide, anthocyanin, lipid, antiviral drug, antibiotic, chemotherapeutic, or combination thereof.

34. The method of paragraph 33, wherein the biomolecule and/or active agent comprises or is a protein.

35. The method of paragraph 34, wherein the biomolecule and/or active agent is ovalbumin, serum albumin, interleukin-4, an antibody or antibody reagent, cholera toxin subunit B, biotin, cytokine, or lectin.

36. The method of paragraph 35, wherein the antibody or antibody reagent is specific for an immune checkpoint protein.

37. The method of paragraph 33, wherein the biomolecule and/or active agent is a viral particle or viral vector.

38. The method of paragraph 37, wherein the viral particle or viral vector is an adeno-associated virus vector.

39. The method of paragraph 38, wherein the adeno-associated virus vector is AAV9.

40. A method of administering a biomolecule and/or active agent to a patient in need of treatment with the biomolecule, the method comprising administering a cell of any of paragraphs 16-24 to the patient.

41. The method of paragraph 40, wherein the cell is autologous to the patient.

42. The method of any of paragraphs 40-41, wherein the cell is an erythrocyte and a plurality of the biomolecule and/or active agent administered to the patient is delivered to the lungs.

43. The method of any of paragraphs 40-41, wherein the cell is a macrophage and a plurality of the biomolecule and/or active agent administered to the patient is delivered to the brain, a tumor, or a site of inflammation or autoimmune inflammation.

44. The method of any of paragraphs 40-41, wherein the cell is a natural killer cell and a plurality of the biomolecule and/or active agent administered to the patient is delivered to a tumor.

45. The method of any of paragraphs 40-41, wherein the cell is a T cell and a plurality of the biomolecule and/or active agent administered to the patient is delivered to a tumor.

46. The method of any of paragraphs 40-41, wherein the cell is a neutrophil and a plurality of the biomolecule and/or active agent administered to the patient is delivered to the lungs or a site of inflammation.

47. A functionalized cell of any of paragraphs 16-24, for use in a method of administering a biomolecule and/or active agent to a patient in need of treatment with the biomolecule, the method comprising administering the functionalized cell to the patient.

48. The cell of paragraph 47, wherein the cell is autologous to the patient.

49. The cell of any of paragraphs 47-48, wherein the cell is an erythrocyte and a plurality of the biomolecule and/or active agent administered to the patient is delivered to the lungs.

50. The cell of any of paragraphs 47-48, wherein the cell is a macrophage and a plurality of the biomolecule and/or active agent administered to the patient is delivered to the brain, a tumor, or a site of inflammation or autoimmune inflammation.

51. The cell of any of paragraphs 47-48, wherein the cell is a natural killer cell and a plurality of the biomolecule and/or active agent administered to the patient is delivered to a tumor.

52. The cell of any of paragraphs 47-48 wherein the cell is a T cell and a plurality of the biomolecule and/or active agent administered to the patient is delivered to a tumor.

53. The cell of any of paragraphs 47-48, wherein the cell is a neutrophil and a plurality of the biomolecule and/or active agent administered to the patient is delivered to the lungs or a site of inflammation.

54. A method of administering a viral vector and/or reducing the immune clearance of viral vectors, the method comprising administering a viral particle or viral vector adhered to a cell.

55. The method of paragraph 54, wherein the viral particle or viral vector is adhered to the cell via by one or more nanocomplexes.

56. The method of any of paragraphs 54-55, wherein cell is a functionalized cell of any of paragraphs 16-24, and wherein the biomolecule and/or active agent comprises a viral particle or viral vector 57. The method of any of paragraphs 54-56, wherein the cell is a red blood cell.

58. The method of any of paragraphs 54-57, wherein the viral particle or viral vector is an adeno-associated virus vector.

59. The method of paragraph 58, wherein the adeno-associated virus vector is AAV9.

60. A method of gene therapy comprising administering a functionalized cell of any of paragraphs 16-24, wherein the biomolecule and/or active agent comprises a nucleic acid sequence, e.g., a nucleic acid sequence suitable for or configured for gene therapy.

61. The method of paragraph 60, wherein the gene therapy target is primarily in the lungs 62. The method of paragraph 60, wherein the gene therapy target is primarily in the brain.

63. The method of any of paragraphs 60-62, wherein the biomolecule and/or active agent is a viral particle or viral vector.

64. The method of paragraph 63, wherein the viral particle or viral vector is an adeno-associated virus vector.

65. The method of paragraph 64, wherein the adeno-associated virus vector is AAV9.

The technology described herein is further illustrated by the following examples which in no way should be construed as being further limiting.

EXAMPLES

Example 1—Cellwrap: Living Cells Engineered with Polyphenol-Functionalized Biologically Active Nanocomplexes Approaches to safely and effectively augment cellular functions without transfection and expansion, especially through the integration of biologically labile domains, remain of great interest. Here, we establish a versatile strategy to assemble biologically active nanocomplexes, including proteins, DNA, mRNA, and even viral carriers, on cellular surfaces to generate a cell-based hybrid system referred as Cellwrap. This strategy can be used to engineer a wide range of cell types used in adoptive cell transfers, including erythrocytes, macrophages, NK, and T cells. Erythrocyte$_{plex}$ can enhance the delivery of a cargo protein to the lungs in vivo by 11-fold as compared to the free cargo counterpart. Biomimetic microfluidic experiments and modeling provided detailed insights into the targeting mechanism. Demonstrated Macrophage$_{plex}$ is capable of penetrating tumor spheroids to deliver anti-PD-L1 checkpoint inhibitors as a therapeutic strategy. This simple and adaptable approach offers a platform for the rapid generation of complex cellular therapeutic systems.

Cell-based therapies, comprising administration of living cells to patients for direct therapeutic activities, have experienced remarkable success in the clinic (1-4). Chimeric antigen receptor (CAR) T cell therapies in particular have led to improved remission rates in patients with multiple myeloma, leukemia, lymphomas, melanoma, cervical cancer, bile duct cancer, and neuroblastoma compared to traditional chemotherapeutic regimens (5-8). New treatment strategies implementing erythrocytes, macrophages, monocytes, natural killing (NK) cells, and pluripotent stem cells are in various stages of development for the treatment of cancer, chronic infections, and autoimmune disorders (9). However, many of these strategies rely on the genetic alteration and expansion of cells, which requires several weeks of preparation (10). For example, CAR T cell therapies require a preparation time of at least three weeks, which can be prohibitively long for patients with advanced or metastatic cancers (11, 12). Thus, there is a broad interest in engineering functional cells ex vivo in a manner that is rapid, scalable, and agnostic to the therapeutic cell of interest (10, 13).

One approach to address this challenge is the concurrent delivery of biomolecules through the integration of carried nanoparticles (e.g., 'hitchhiking' or 'backpack' systems) on the surface of living cells to improve therapeutic potency (14-18). While this strategy has shown promising results in preclinical studies (19-22), the design and synthesis of highly complex nanoparticles can be a challenge to adopt clinically. Additionally, the stable attachment of nanoparticles to cell surfaces often relies on interactions that only work for certain cell types in specific particle-cell combinations (e.g., electrostatic, hydrophobic, hyaluronan-CD44, and antibody-antigen interactions) (10, 23). Currently, no platform exists to functionalize a wide range of mammalian cells of therapeutic interest with a wide range of therapeutics in a simple, scalable manner. Therefore, there is an urgent need to develop a strategy to integrating biologically active molecules on cell surfaces that can be applied to a broad range of cell types and biomolecular payloads, while reducing timescales necessary for preparing therapeutic biohybrid cellular systems.

Described herein is the exploration of a building blocks approach to biological molecules and assembly on the surface of mammalian cells for advanced cell-based therapies. Described herein is the use of a polyphenol-based molecular engineering strategy as a rapid and efficient approach to functionalize cell surfaces with a range of payloads to aid in adoptive cell transfers that we refer to as Cellwrap. The polyphenol moieties functionalized on the molecules (FIG. 1A) can facilitate the assembly of biologically active nanocomplexes on cell surfaces directed by interfacial molecular interactions (FIGS. 1B and 1C) (24, 26). This simple and modular approach enabled a modular functionalization of erythrocytes with at least 10 biomolecules, including functional proteins. DNA, mRNA, and viral carriers to generate biohybrid cellular systems. Several other cell types including T cells, monocytes, and NK cells were also engineered to their corresponding Cellwrap variants.

Figures 1D, 1E:
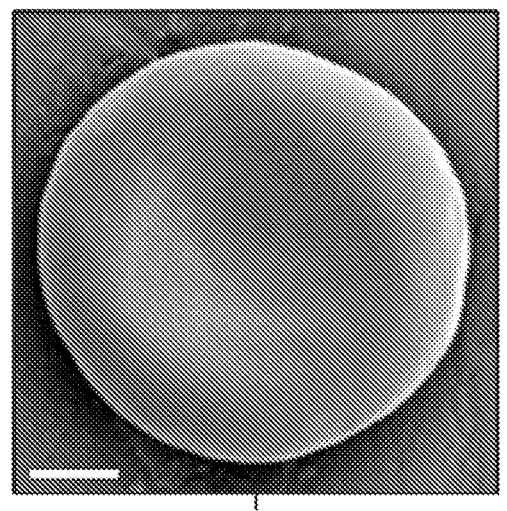
Figure 1F:
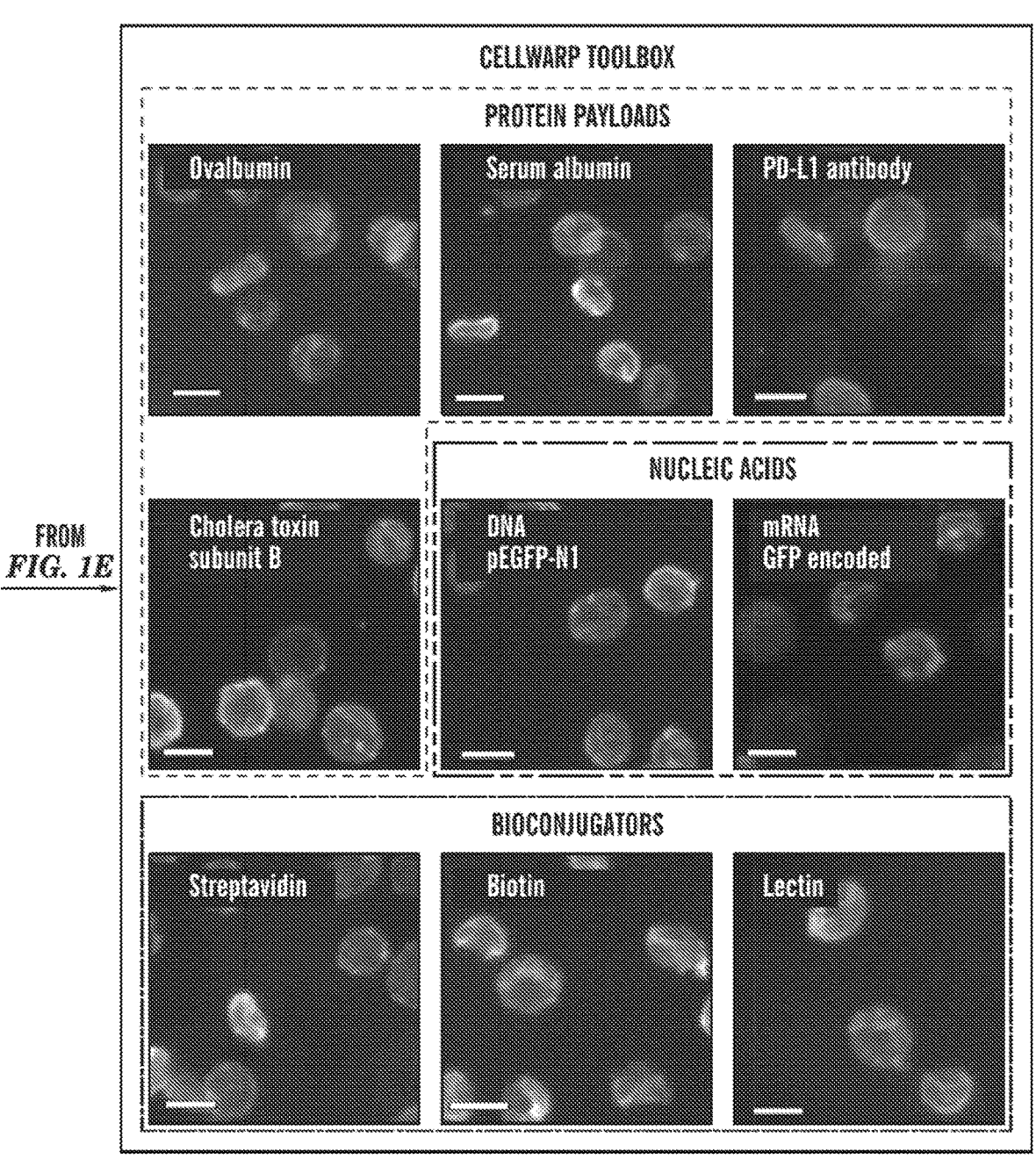

Simple and Rapid Assembly of Biomolecule and/or Active Agent Nanocomplexes on Cell Surface Erythrocytes were selected as the initial example of Cellwrap design. Erythrocyte-based therapies are an emerging platform for vascular drug delivery due to their biocompatibility and clinical safety of transfusion (27-32) (FIG. 1D-1F). It was found that the stability of protein nanocomplex largely depended on the stoichiometric ratios of tannic acid to functionalized proteins. The protein nanocomplex stability depended on the stoichiometric ratios of tannic acid and functionalized proteins (FIG. 5). A critical stoichiometric ratio of 570 was found, below which the size of nanocomplexes was less than 10 nm. The hydrodynamic size of the nanocomplexes increased dramatically for ratios above the critical stoichiometric ratio and eventually increased to ~900 nm for a ratio of 1900. Therefore, a minimal concentration of tannic acid was chosen to form the nanoscale complexes (33). FIGS. 6A-6B show no aggregation for a stoichiometric ratio of 190 when the tannic acid concentration is 0.2 mg mL$^{-1}$. The ultra-small nanocomplexes (6.8±2.5 nm. FIG. 7) are of a favorable size range for the formation of uniform nanoscale networks on the cell surfaces without blocking cellular receptors and molecular exchangeability as shown later in biocompatibility as well as cellular sensing performance tests.

Figure 9A:
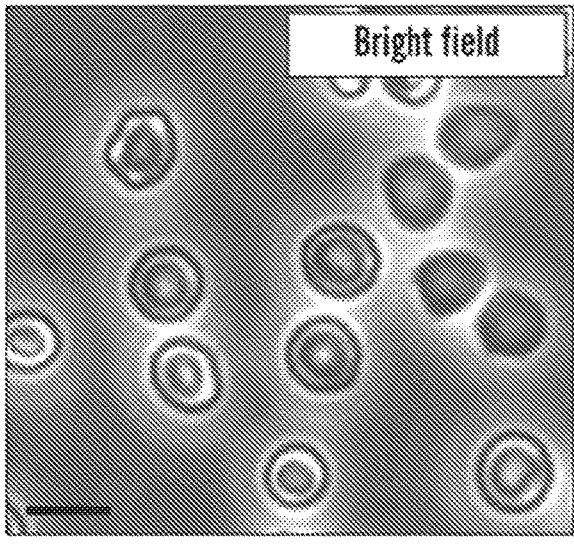
FIGS. 9A-9B depict bright field and florescence microscopy images of erythrocytes incubated with Alexa 488 probe-conjugated BSA. After the incubation of BSA, the erythrocytes were washed by PBS three times to remove the free BSA. The negligible fluorescence signal confumed that the natural adsorption of protein on cell surface is not strong enough to form uniform nanoscale assemblies on erythrocytes. This also supported the crucial roles of polyphenol-based functionalization on the proteins and following assembly on cell surface. Scale bars are 5 μm.
Figure 9B:
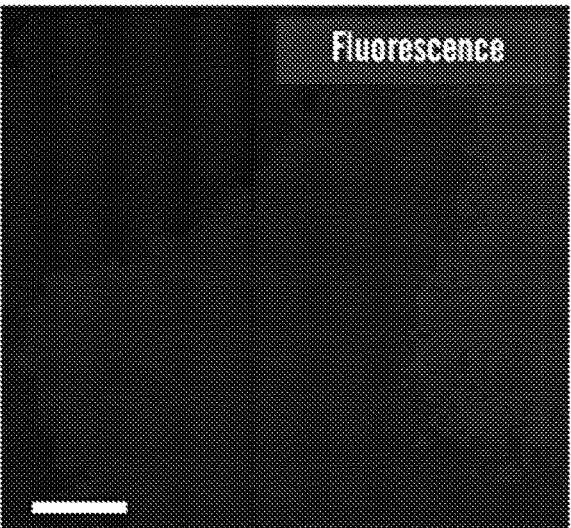

The simple mixing of polyphenol-functionalized nanocomplexes with erythrocytes (FIG. 1D) results in the assembly of these nanocomplexes on their surfaces (FIG. 1E). The interactions between the modularized protein nanocomplexes and cell surfaces facilitate the driving force of rapid interfacial assembly (34). The entire preparation process can be achieved within 5-10 min, demonstrating an exceptionally simple and platform process for the use of Cellwrap therapies in the clinic. Specifically, the biologically functional nanocomplexes can be prepared and stored in a ready-to-use status, followed by the rapid engineering of biohybrid functional cells when the donor cells are ready. FIG. 1F shows the greater versatility in the toolbox of biomolecules used for the cellular integration, due to varying molecular interactions between polyphenols and biomolecules (e.g., protein. DNA, alkaloid, polysaccharide, anthocyanin, lipid) (35). The simplicity and modularity of Cellwrap enabled the assembly of 10) representative biomolecules and viral carriers (FIGS. 8A-8B), with different molecular sizes, charges, levels of hydrophobicity, and functionalities. In the absence of polyphenol-functionalized nanocomplexes, the negligible fluorescence signal on the surfaces of cells revealed that the non-specific adsorption of biomolecules on cell surfaces could not achieve the formation of uniform and high loading of carried biomolecules (FIGS. 9A-9B). The cargos are categorized to four groups: proteins (including ovalbumin, serum albumin, antibody, cholera toxin subunit B), nucleic acids (including coded DNA, mRNA) (36), bioconjugators (including streptavidin, biotin, and lectin), and viral carriers. The robustness of the Cellwrap technique indicates that the polyphenol-based functionalization strategy generates a versatile interfacial attractive force with the surfaces of many cell types, which is a major challenge in current particle-based 'hitchhiking' or 'backpack' systems.

Figure 2B:
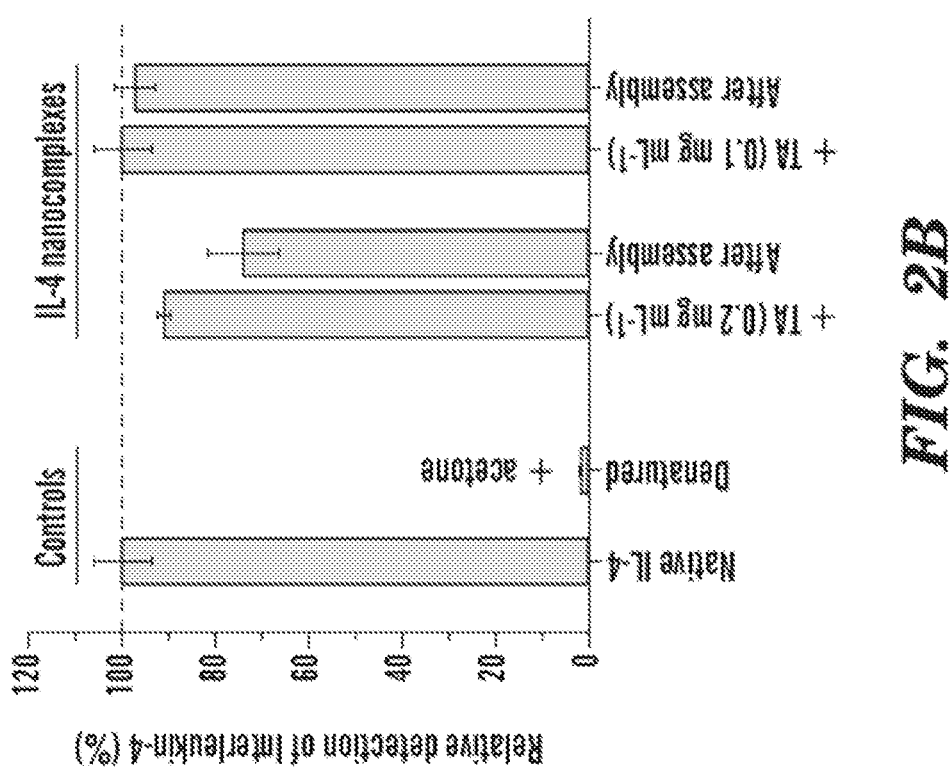
FIGS. 2A-2F depict the engineering of Erythrocyte$_{plex}$ through the assembly of polyphenol-functionalized protein nanocomplexes on erythrocytes.
Figure 2A:
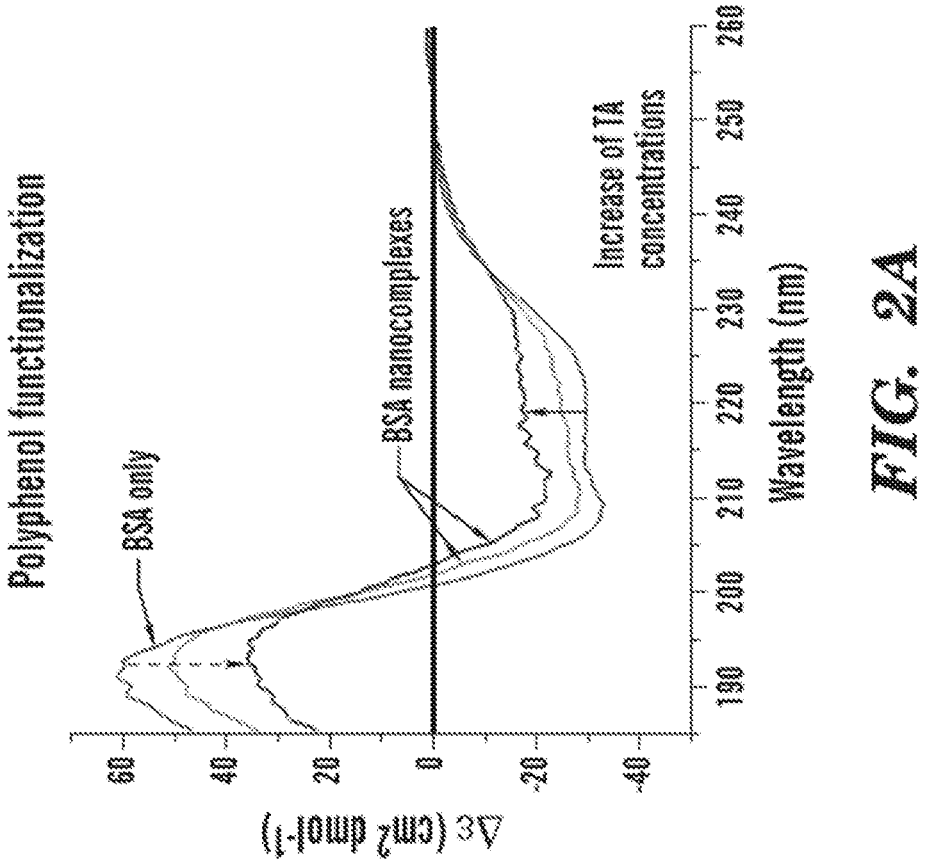
Figure 2C:
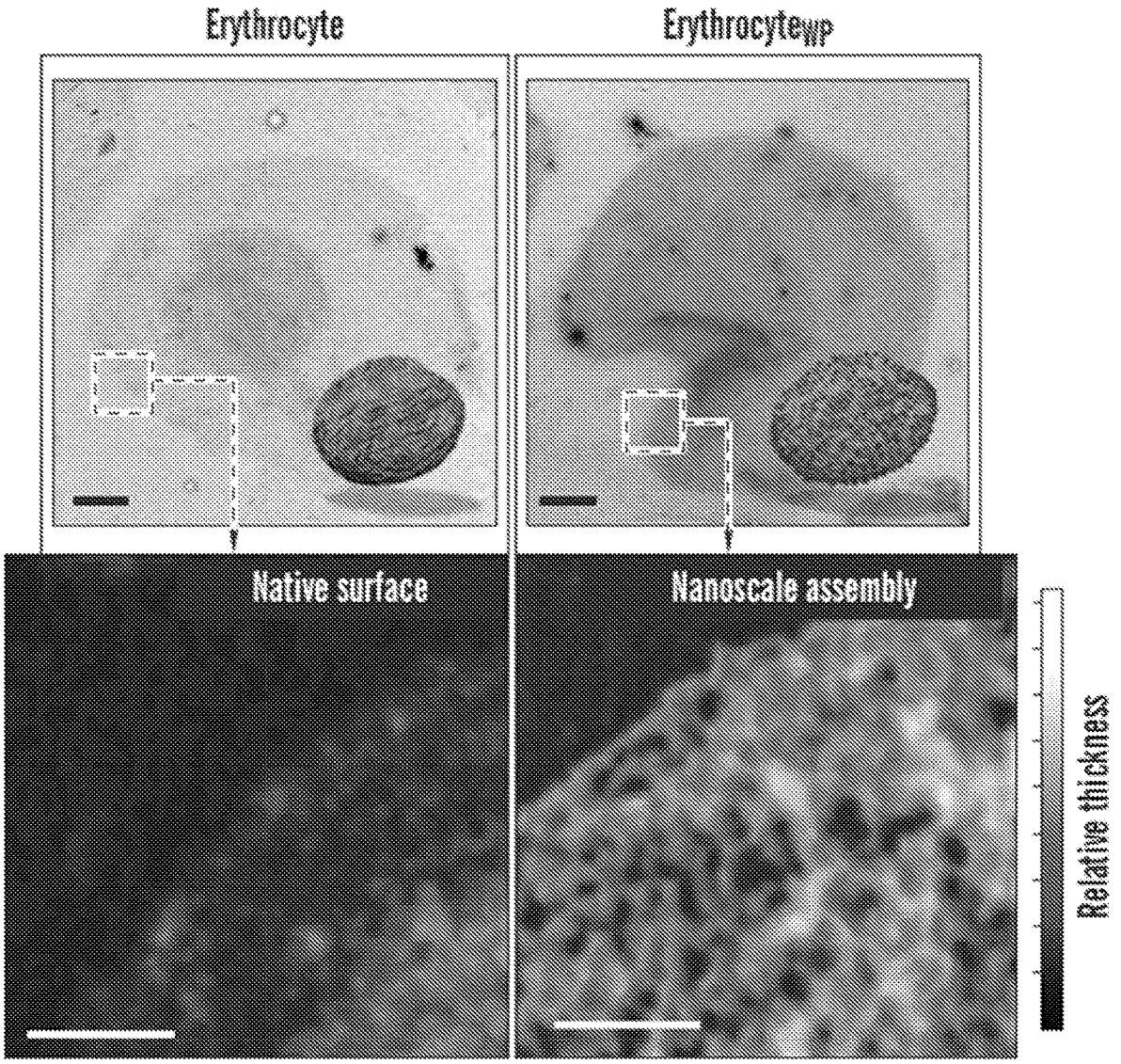
Figure 2D:
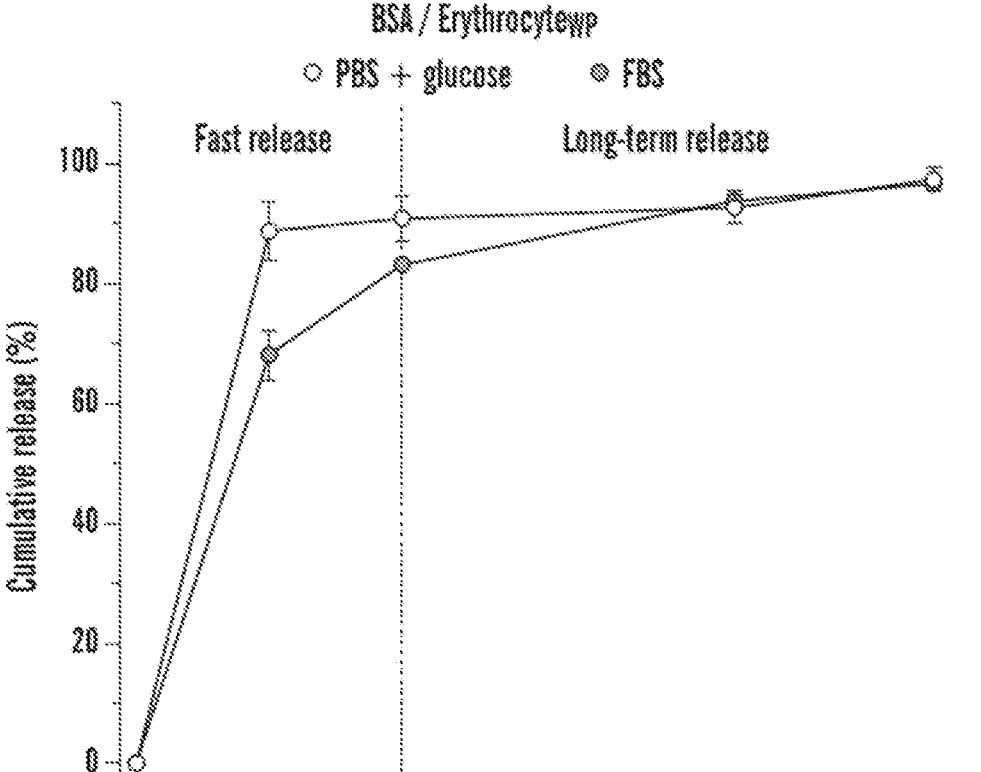
Figure 10:
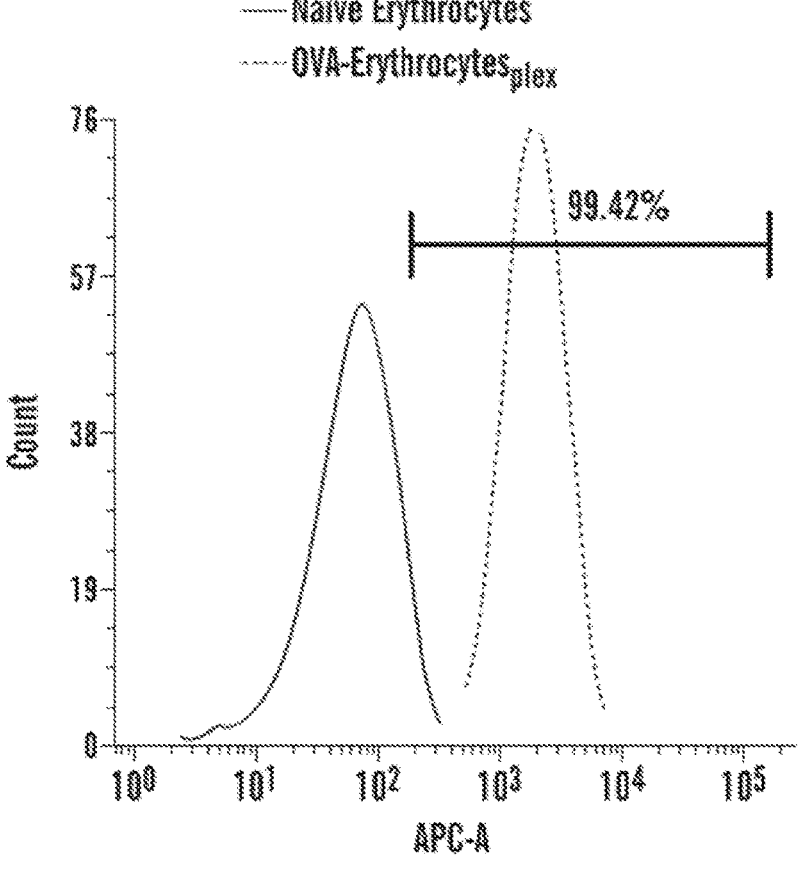
FIG. 10 depicts a flow cytometry histogram of naive erythrocytes and Erythroctye$_{plex}$ integrated with Alexa 647-conjugated OVA. Representative histogram of Erythroctye$_{plex}$ shows dramatic shift of florescence intensity; 99.42% of erythrocytes have OVA on their surface compared with native erythrocytes, suggesting a highly efficient loading of cargo biomolecules on erythrocytes. Variation is represented by SEM (+2.4%) from erythrocytes from six different mice.

Biocompatibility of the Assembly Strategy for Carried Molecules and Cellular Systems FIG. 2A showed the maintenance of α-helix structure of a model protein (bovine serum albumin. BSA) after the polyphenol functionalization (33). Enzyme-linked immunosorbent assay (ELISA) further demonstrated the preservation of biological activity of interleukin-4 (IL-4, a representative protein that is highly sensitive to denaturation) after polyphenol-based functionalization (FIG. 2B). Transmission electron microscopy (TEM) images show the nanostructural change of the erythrocyte surface. The formation of discrete network on the cell surface can be ascribed to the assembly of subunits of protein nanocomplexes (FIG. 2C). In addition, attachment of protein nanocomplexes to Erythrocyte$_{plex}$ was also confirmed by flow cytometry. 96.7%±2.4% of the erythrocytes carried cargo proteins (FIG. 10). An initial fast release of carried protein was observed during the first 4 h, as nearly 65% and 90% of them was released in two physiological conditions including PBS (with 5 mM glucose) and fetal bovine serum (FBS). At longer time periods, the remaining protein released more slowly and reached a plateau after 24 hours (FIG. 2D).

Figure 2E:
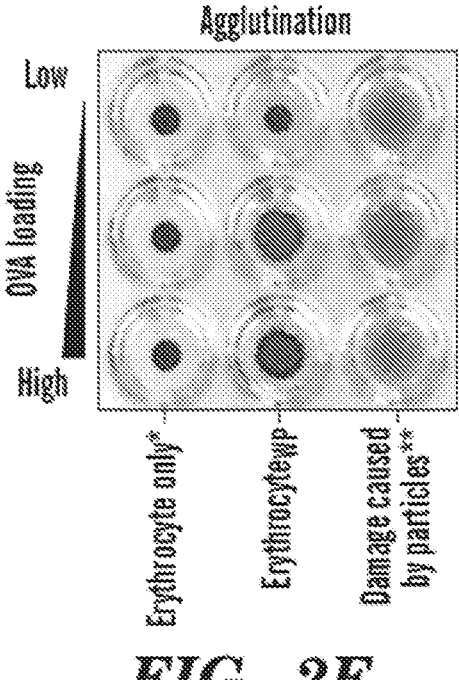
Figure 2F:
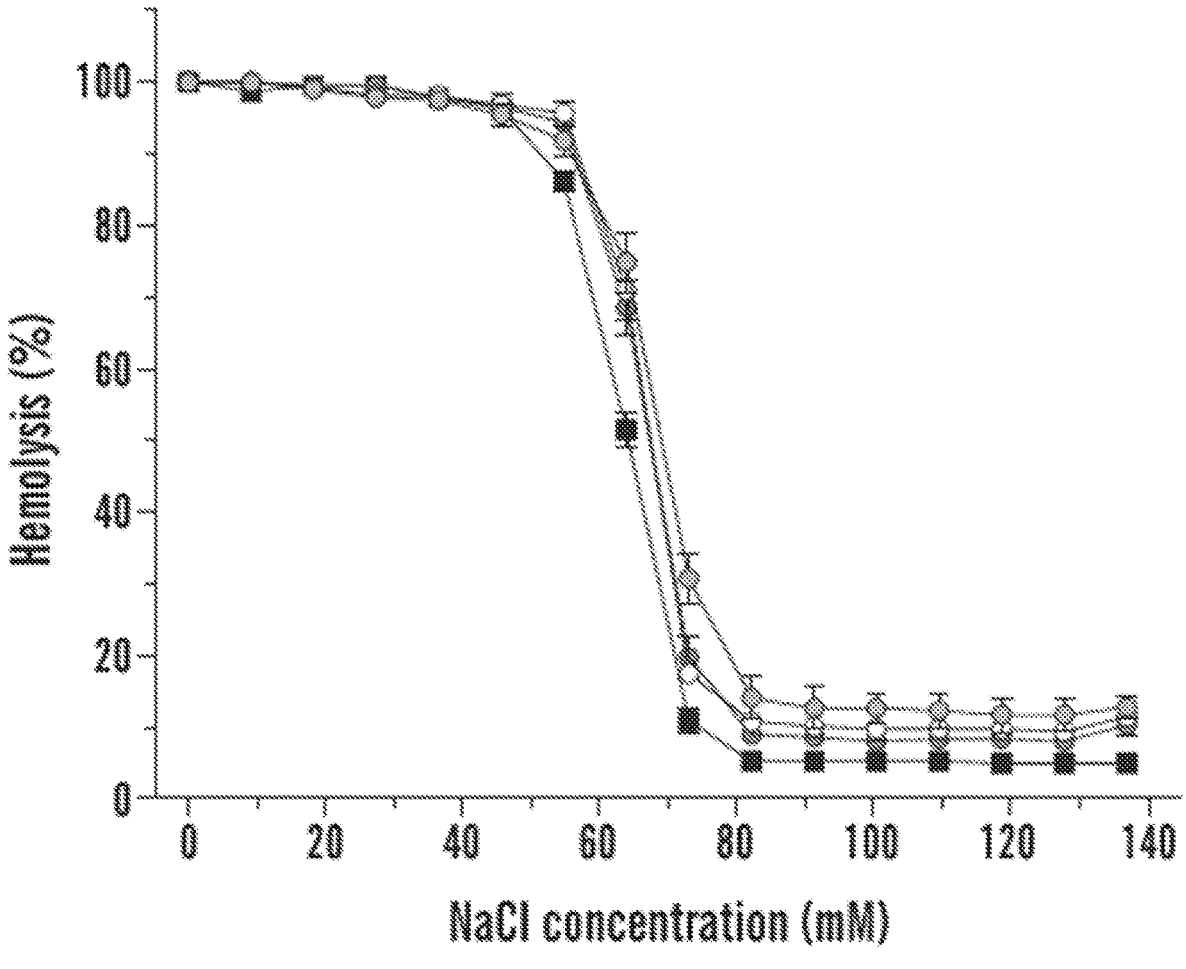
Figure 3A:
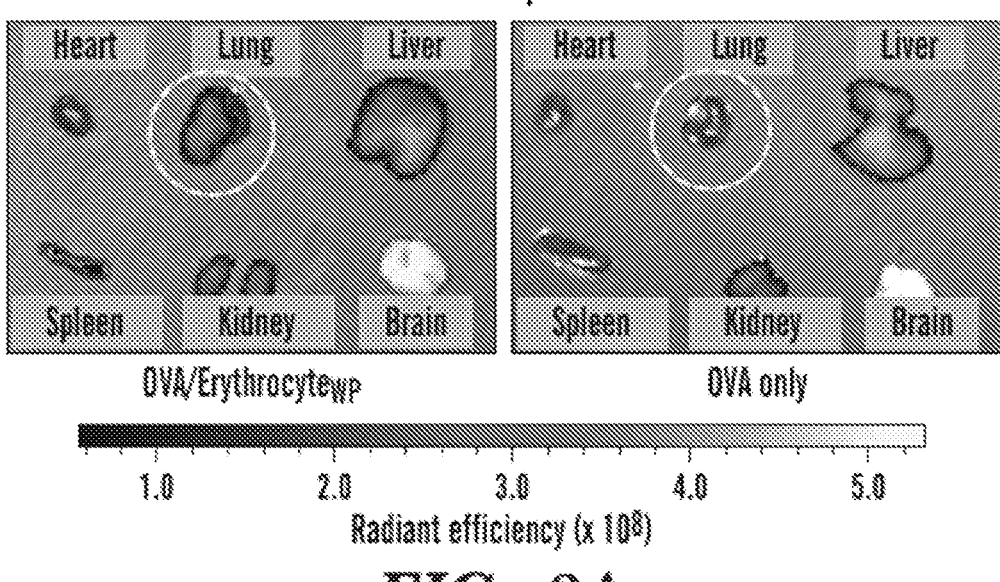
Figure 3B:
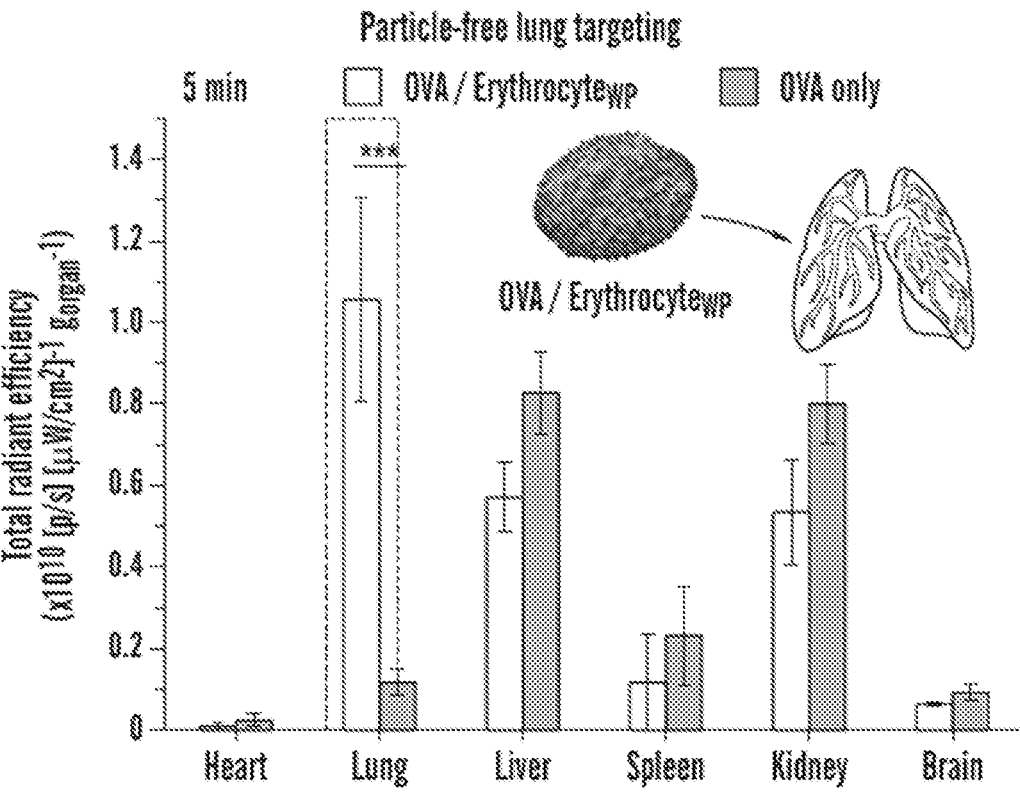
Figure 3C:
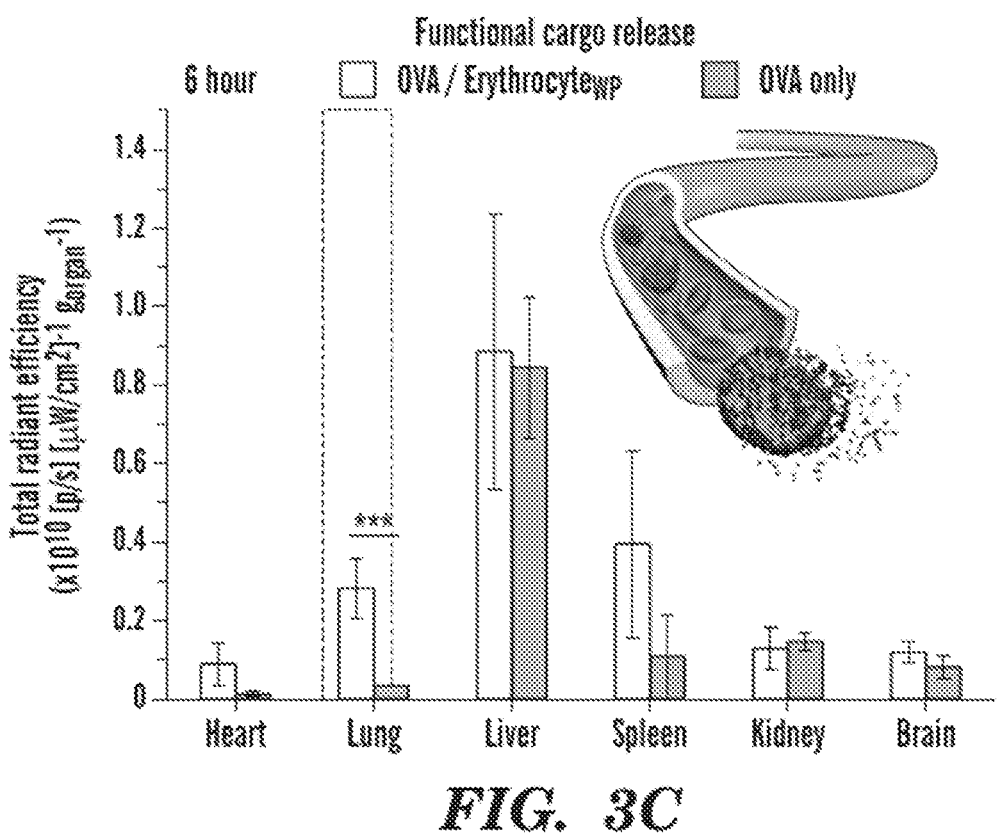
Figure 3D:
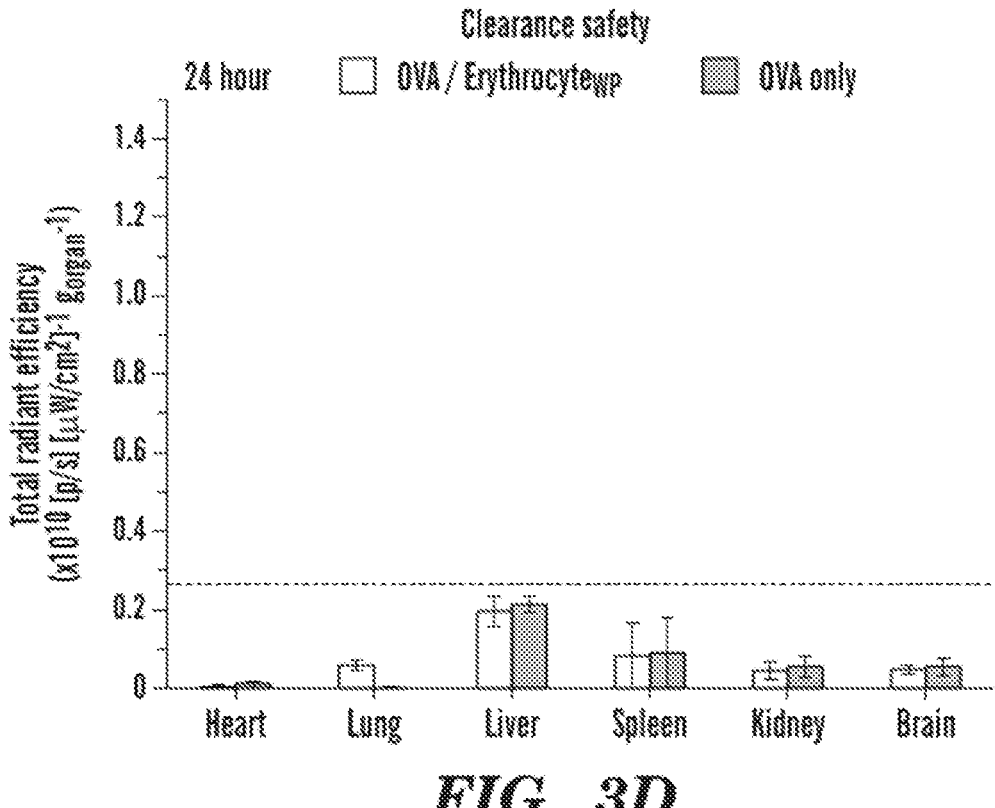
Figure 3E:
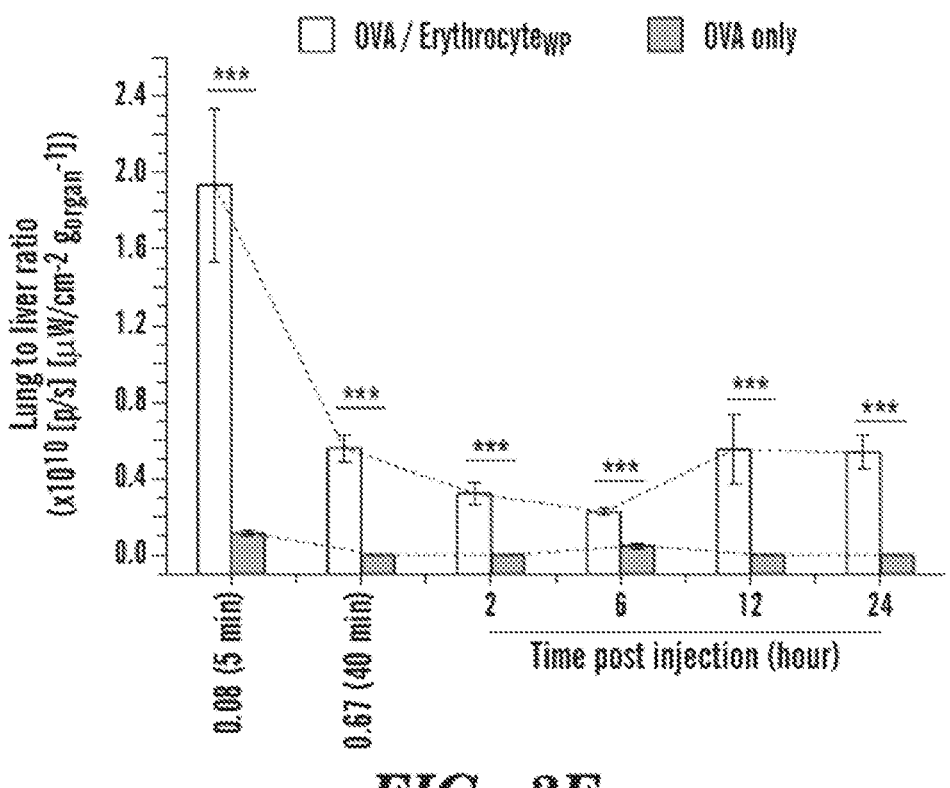
Figure 3F:
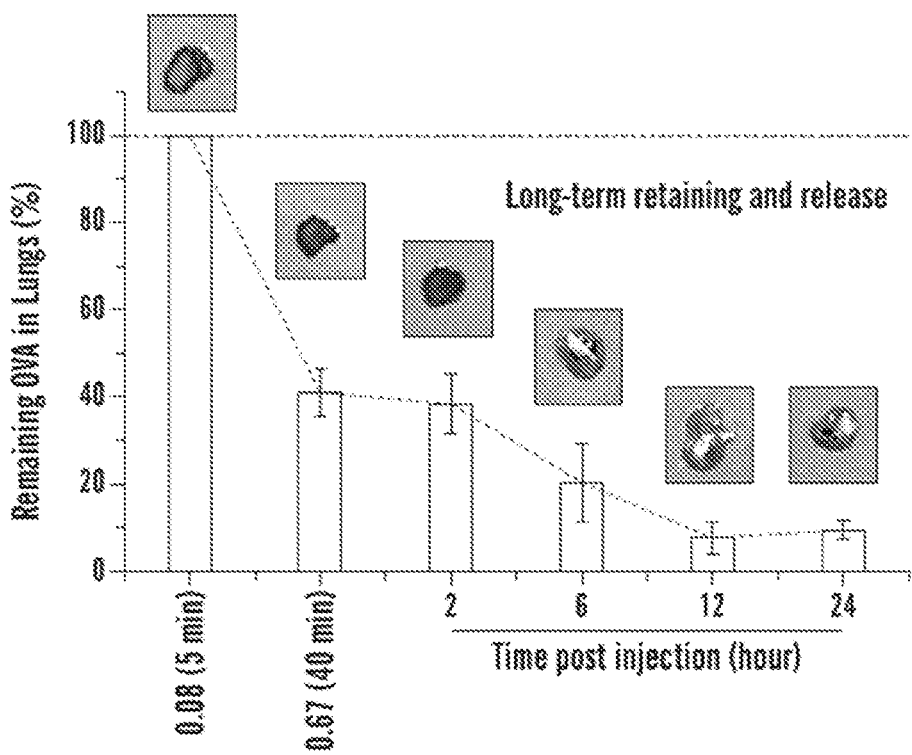
Figure 3G:
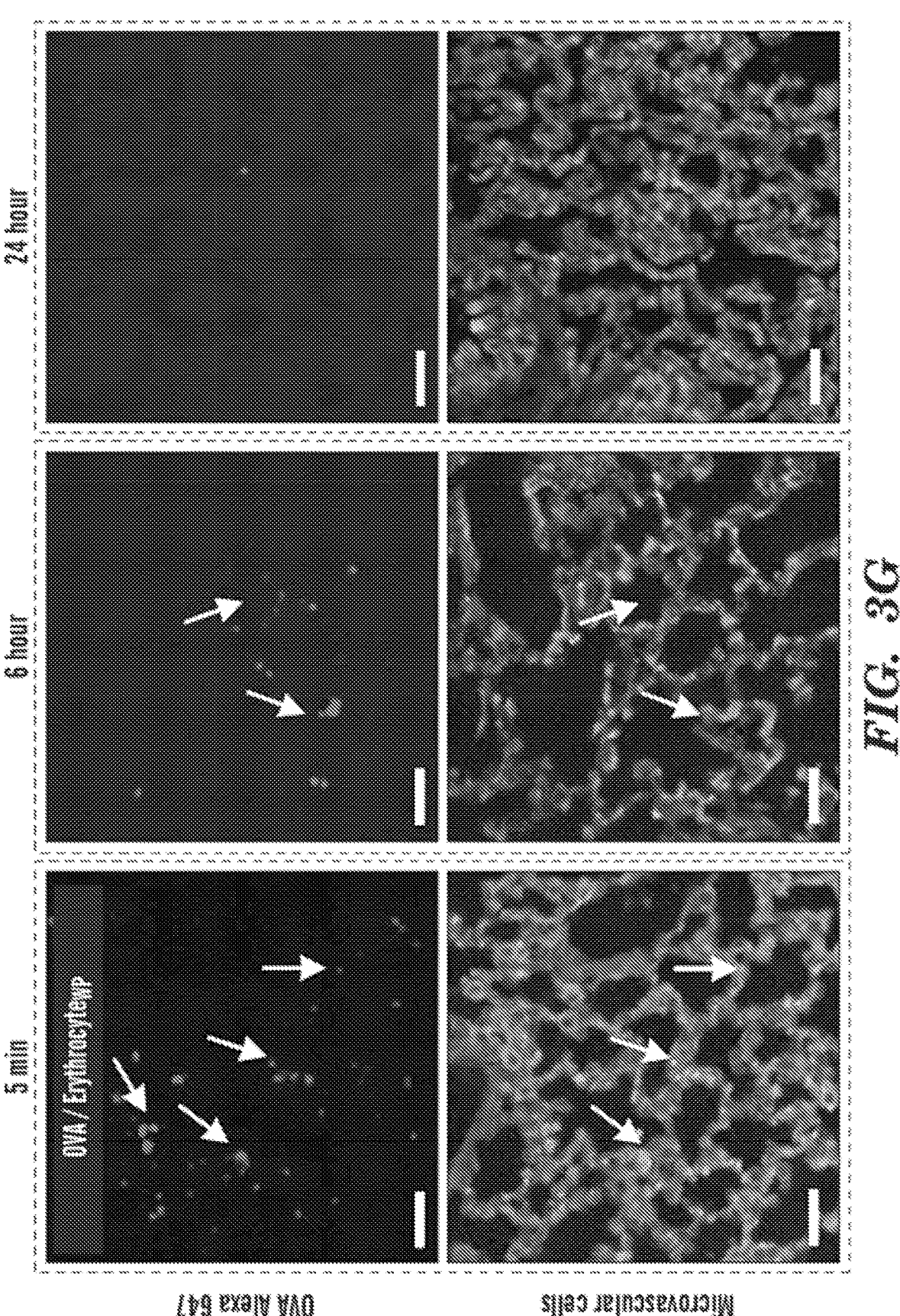
Figure 31:
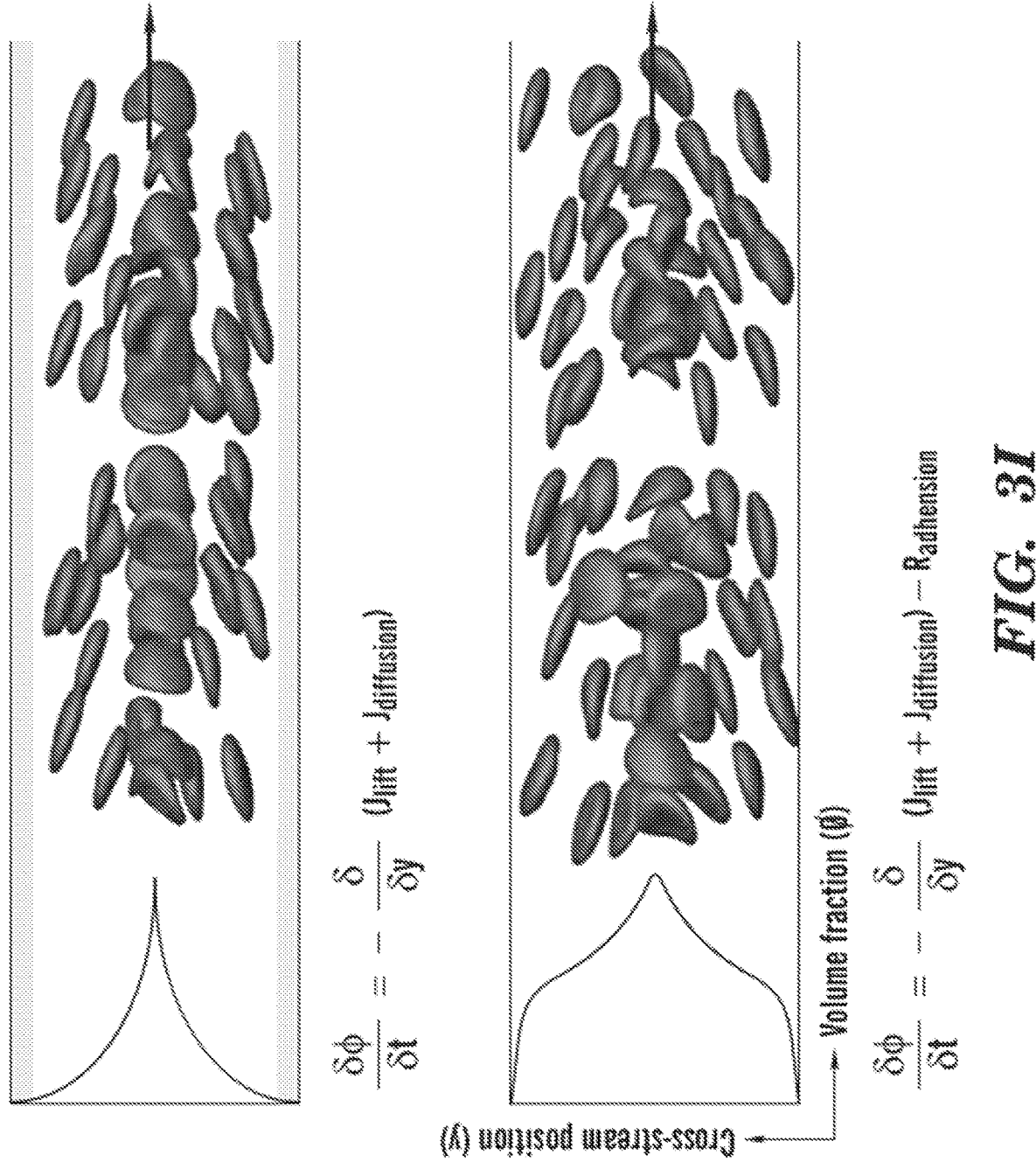
Figure 11:
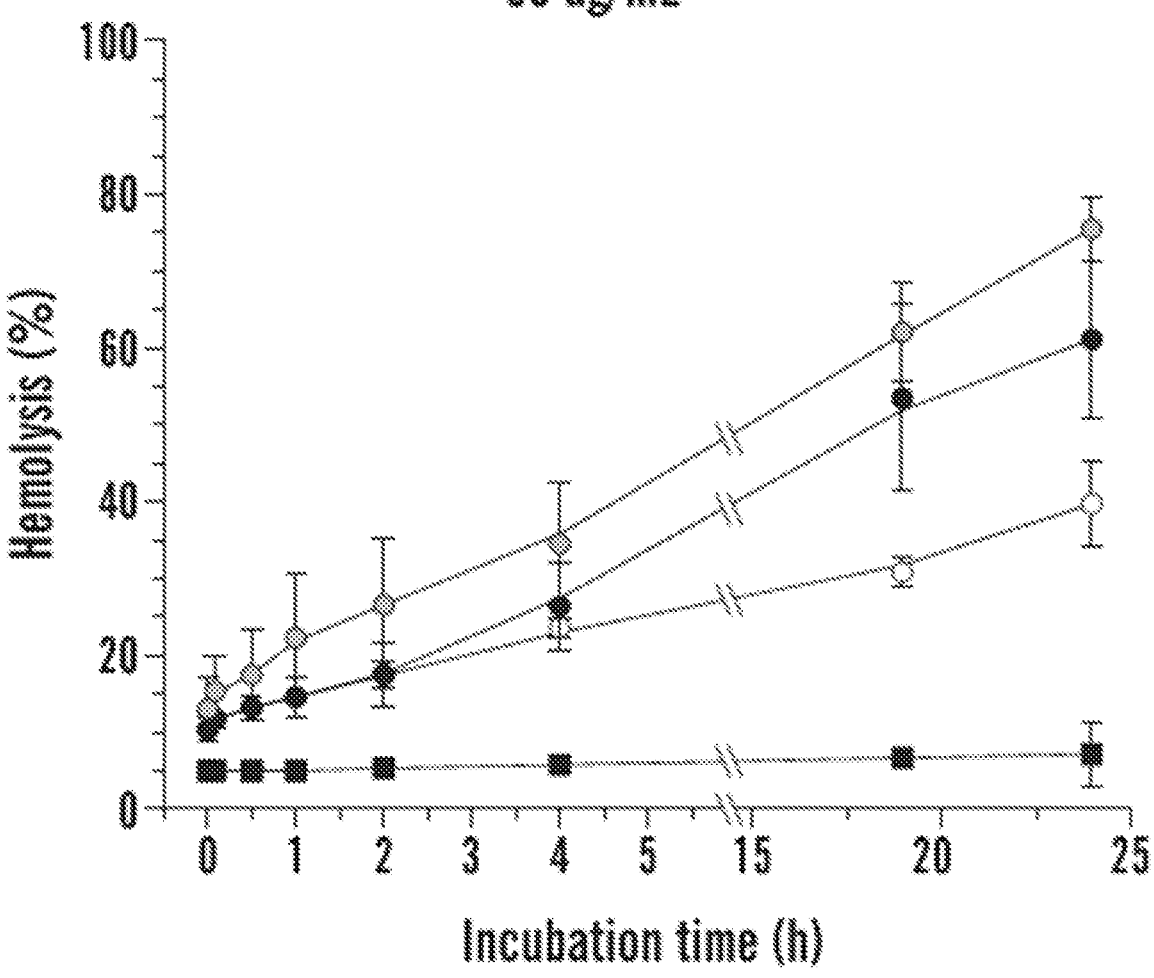
FIG. 11 depicts the osmotic fragility of Erythrocytes, loaded with different amounts of functionalized OVA nanocomplexes under low continuous stress at 37° C. for 24 hours. Variation is represented by SE (error bars) from three independent replicates for all data points.

To investigate the biocompatibility of polyphenol-functionalized protein nanocomplexes on erythrocytes, different amounts of functionalized protein nanocomplexes were assembled onto erythrocytes and were analyzed for erythrocyte agglutination by U-shaped microplates. No aggregates were observed in naïve erythrocytes as well as erythrocytes with low amounts of protein (24 µg L$^{-1}$) nanocomplexes absorbed onto their surfaces. However, the amount of aggregates appears to increase with increasing concentrations of protein nanocomplexes, but these aggregations still show much lower toxicities as compared with those induced by carboxylated polystyrene nanoparticles (FIG. 2E). Potential detrimental effects of protein nanocomplexes assembled onto erythrocyte were also investigated by the sensitivity of erythrocytes towards osmotic stress. Assembled protein nanocomplexes led to the formation of slightly sensitized erythrocytes at 1% hematocrit concentration when immediately exposed to various hypotonic solutions, indicating a slight decrease in erythrocyte sensitivity compared to naïve erythrocytes (FIG. 2F). Mechanical fragility of Erythrocyte$_{plex}$ under prolonged levels of low shear stress was examined. FIG. 11 shows that at 1% hematocrit, erythrocytes displayed low levels of hemolysis (~5% at 24 hours) when rotated at 37° C. Within this period of 1 hour, the assemblies of low and medium amounts of protein nanocomplexes slightly aggravated hemolysis (~15%) compared to erythrocytes (~5%). Furthermore, high amounts of protein nanocomplexes further induced hemolysis (25%) during this period, suggesting that the optimized concentration of nanocomplexes (24 µg L$^{-1}$) has negligible effect on the cell integrity though the rate of hemolysis is dependent of the amount of the protein nanocomplexes assembled onto the surface of erythrocytes.

In Vivo Lung Targeting Ability and Payload Release of Erythrocyte$_{plex}$

Figure 12:
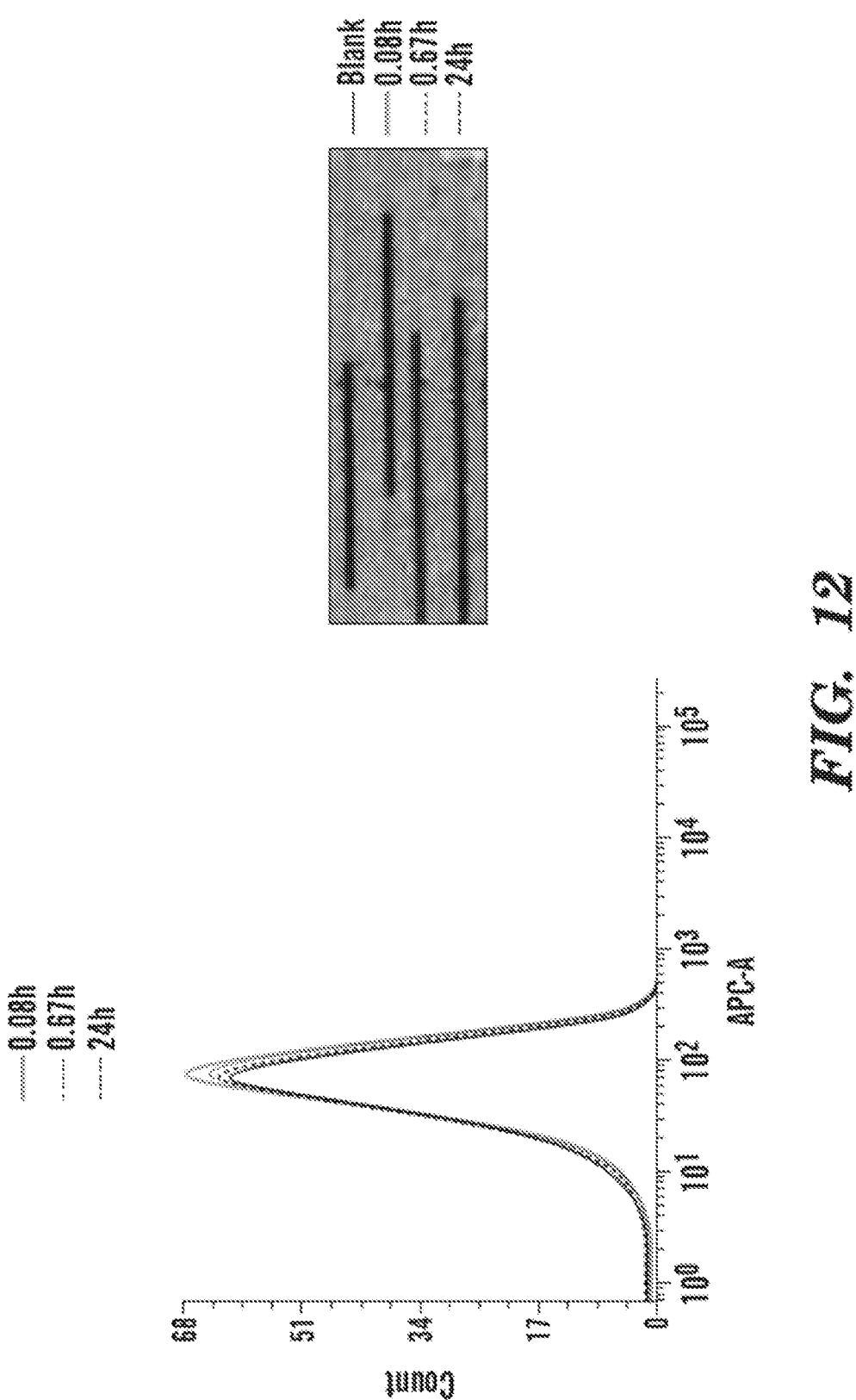
FIG. 12 depicts a flow cytometry histogram of blood from mice injected intravenously with Erythyrocyteplex integrated with Alexa 647-conjugated OVA. Representative flow cytometry histogram of Erythroctye$_{plex}$, present in blood collected from IVC (in heparin tubes) after 0.08 h, 0.67 h, and 24 h post injection (Inset: IVIS fluorescence images). There is no shift of florescence intensity at any time point; suggesting Erythroctye$_{plex}$ are not circulating in the blood even after 0.08 h post injection. Blood was obtained from 3-6 different mice at each time point.

The efficacy of Erythrocyte$_{plex}$-mediated delivery to the lungs in vivo after intravenous administrations was examined (FIG. 3). Biodistribution analysis revealed strong signal intensities in the liver 5 min (0.08 hour) after the administration of free OVA protein alone. However, a significant signal increase was observed in the lungs of mice injected with OVA/Erythrocyte$_{plex}$, 11-fold higher than OVA alone. Minimal signals were detected in the heart and brain (FIGS. 3A and 3B). As time progressed, relatively high signal of OVA/Erythrocyte$_{plex}$ was still observed in the lungs 6-hour post injection (FIG. 3C). 24 hours post injection, the signal of OVA carried by Erythrocyte$_{plex}$ decreased and approached the background, suggesting their safe clearance in vivo (FIG. 3D). Interestingly, Erythrocyte$_{plex}$ do not require any affinity moieties (e.g., endothelial-binding antibody) to achieve high lung uptake; the fold-increase of lung uptake ranged from ~11-fold (from 0.08 hours to 6 hours) to ~140-fold (at 24 hours) compared to the free OVA counterpart controls. After 0.08 hours. OVA/Erythrocyte$_{plex}$ generated a high lung-to-liver ratio of ~2, which is nearly 18-fold higher than that observed with free OVA. Moreover, after 24 hours, the lung-to-liver ratio was 335-fold higher compared to the free OVA counterparts (FIG. 3E). These results suggest that Erythrocyte$_{plex}$ enabled highly selective delivery of protein cargo in the lungs, sustained long release times, and eventually permitted excretion (FIG. 3F). There was little to no signal observed in the whole blood at any time points (FIG. 12), suggesting a stable attachment of protein on Erythrocyte$_{plex}$ and targeted release in the lung capillaries. Lung sections were analyzed to investigate the distribution of OVA/Erythrocyte$_{plex}$ within the microstructures of lung. As shown in FIG. 3G, the engineered OVA/Erythrocyte$_{plex}$ system was able to deliver a substantial amount of cargo and was highly distributed in these "hard-to-reach" capillary vascular microstructures. Confocal fluorescence microscopy images show the absence of macrophages in the lung tissue 24 hours post injection, indicating that the cargo was delivered to the endothelium rather than was phagocytosed by tissue resident phagocytes (FIGS. 13A-13B).

Figure 15:
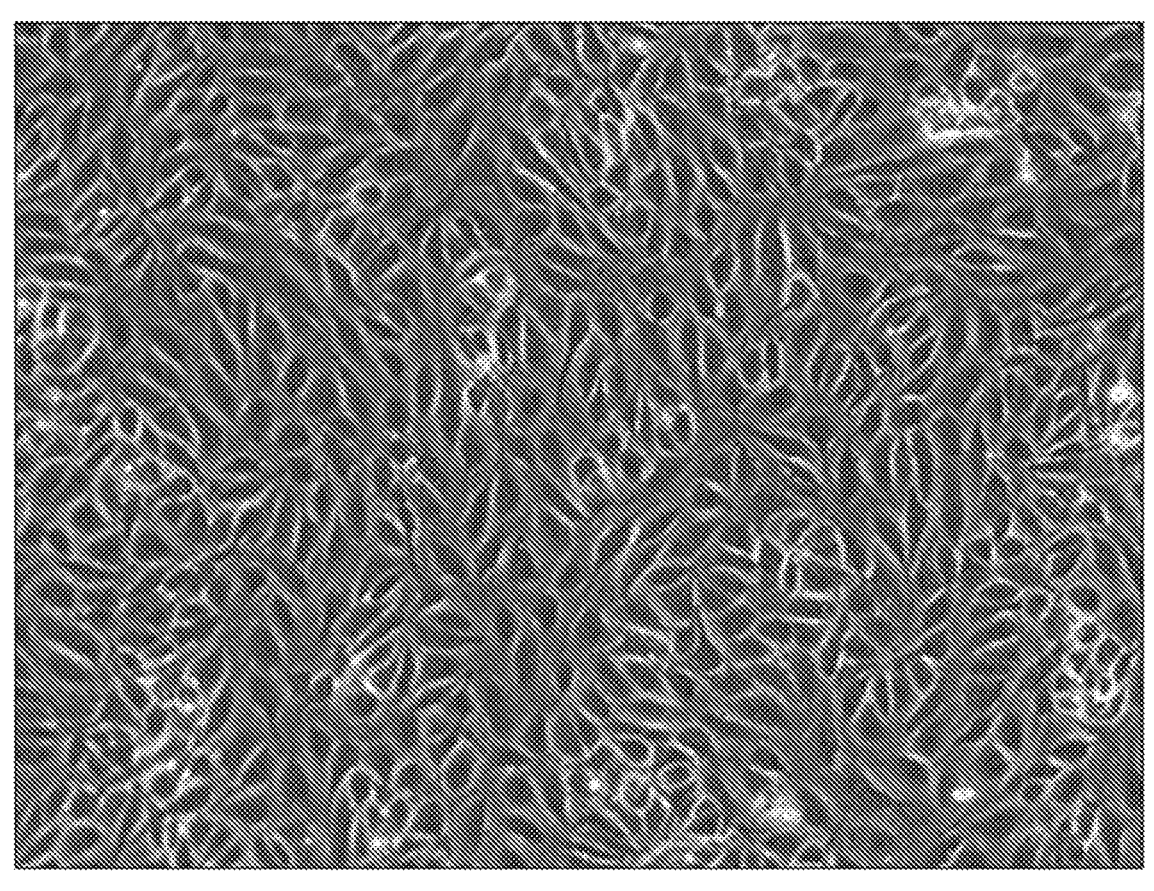
FIG. 15 depicts the morphology of confluent EAhy 926 cells in a tissue culture flask
Figure 16:
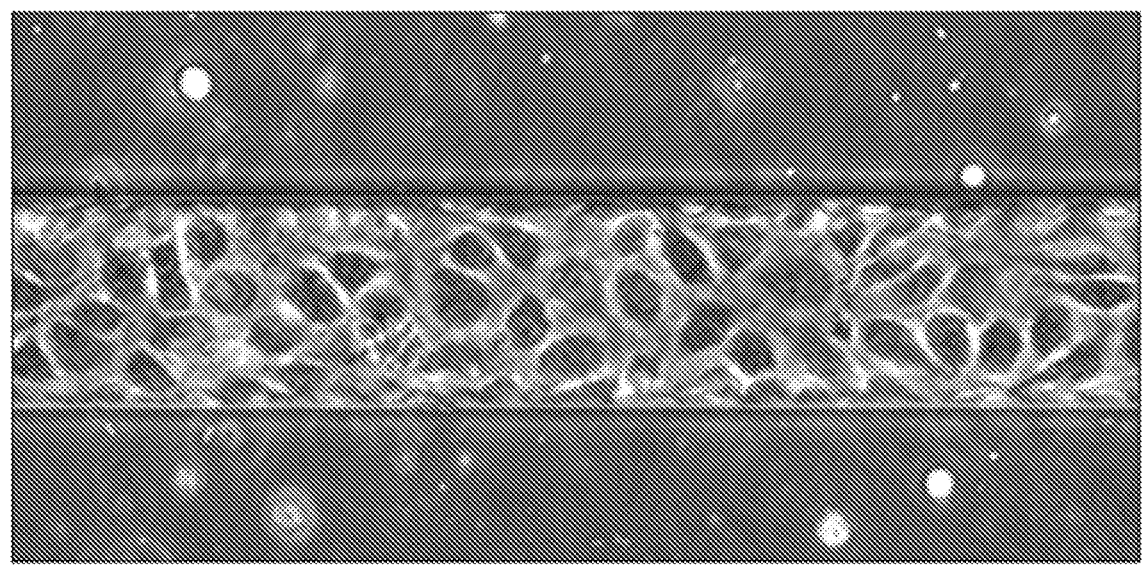
FIG. 16 depicts the morphology of confluent EAhy 926 cells in chip.
Figures 17, 18A, 18B, 18C, 18D:
FIG. 17 depicts a confocal image of actin-stained EA.hy 926 cells (left) showing a monolayer of coating covering inner channel walls (right).
FIGS. 18A-18D depict simulations of the difference of native erythrocytes and OVA/Erythrocyte$_{plex}$ flowing in the vascular channels.
Figure 19:
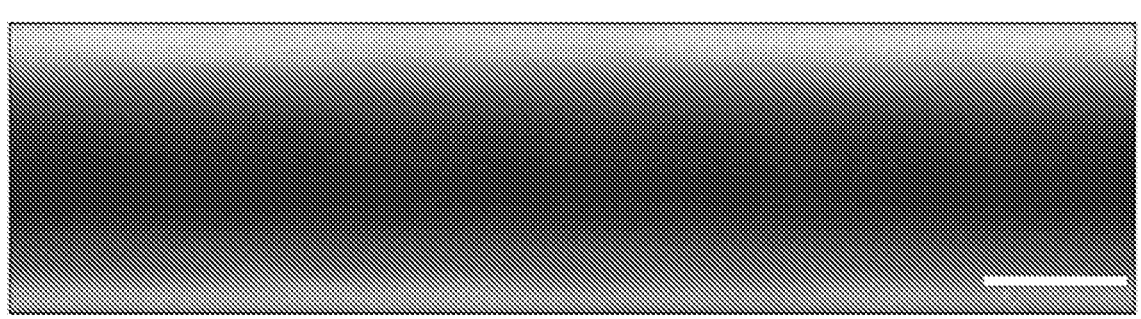
FIG. 19 depicts formation of RBC-free layer in the absence of endothelial cell coating. Biomimetic perfusion chamber experiments to characterize the formation of cell-free layers during the flow of native erythrocytes without the presence of endothelial cells.

The unique 'particle-free' targeting performance of the Erythrocyte$_{plex}$ was further investigated in the biomimetic perfusion chamber experiments (FIG. 3H and FIG. 14). In the microfluidic experiments, erythrocytes and OVA/Erythrocyte$_{plex}$ were flown at 10% hematocrit through 100 µm by 100 µm microfluidic channels coated with a confluent monolayer of endothelial cells mimicking the blood vessel wall (FIGS. 15-17). To verify the integrity of adhered Erythrocyte$_{plex}$-we compared the near-wall concentration distribution of cells in brightfield images. A significant reduction of the cell-free layer thickness was observed in the case of Erythrocyte$_{plex}$ (FIG. 3H, top and middle). Moreover, florescence microscopy images confirmed the adhesion of Erythrocyte$_{plex}$ to the channel wall under physiological flow conditions (FIG. 3H, bottom).

Figure 20:
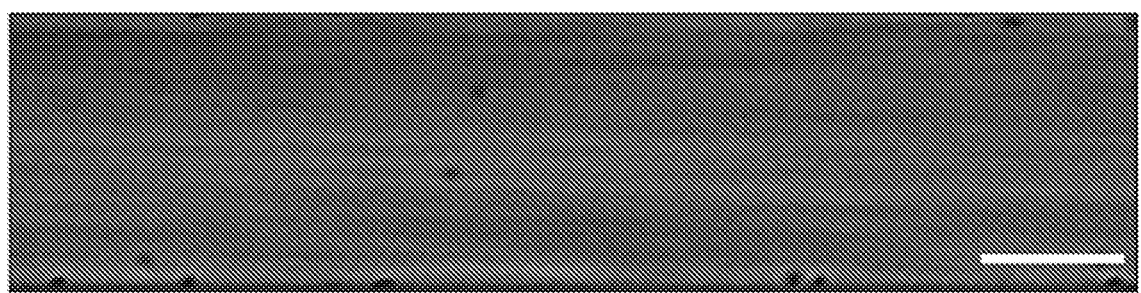
FIG. 20 depicts reduction of cell-free layer showing the endothelial adhesive property of OVA/Erythrocyte$_{plex}$. Biomimetic perfusion chamber experiments to characterize the adhesive property of Erythrocyte$_{plex}$ in vascular channel. Cell-free layer is also absent, providing the contact of Erythrocyte$_{plex}$ to the endothelium.

This formation of a micron-sized cell-free layer near blood vessel walls under flow, commonly known as the Fahreaus-Lindqvist effect, can be explained by the balance between a lift force acting away from the wall due to erythrocyte deformability and shear-induced diffusion due to the hydrodynamic interactions among erythrocytes (FIG. 3I and FIGS. 18A-18D, FIG. 19). Using an existing theory[37,38], the cross-flow concentration distribution of erythrocytes and the resulting cell-free layer thickness was estimated. The near-wall flowing Erythrocyte$_{plex}$ are also subject to adsorption onto vessel walls. We thus theoretically predicted that Erythrocyte$_{plex}$ distribute closer to vessel walls with a diminished cell-free layer at matching flow conditions and cell mechanical properties, consistent with our experimental observations. The adhesive property of Erythrocyte$_{plex}$ onto vessel walls is not specific to the endothelial cells (FIG. 20). Despite it being a reversible and transient process, this adhesion significantly slows down Erythrocyte$_{plex}$ from the fast-flowing blood environment and can contribute to the overall prolonged retention time and lung targeting for drug delivery.

Versatile Toolbox of Cellular Systems of Cellwrap and Macrophage$_{plex}$

Figures 4A, 4B:
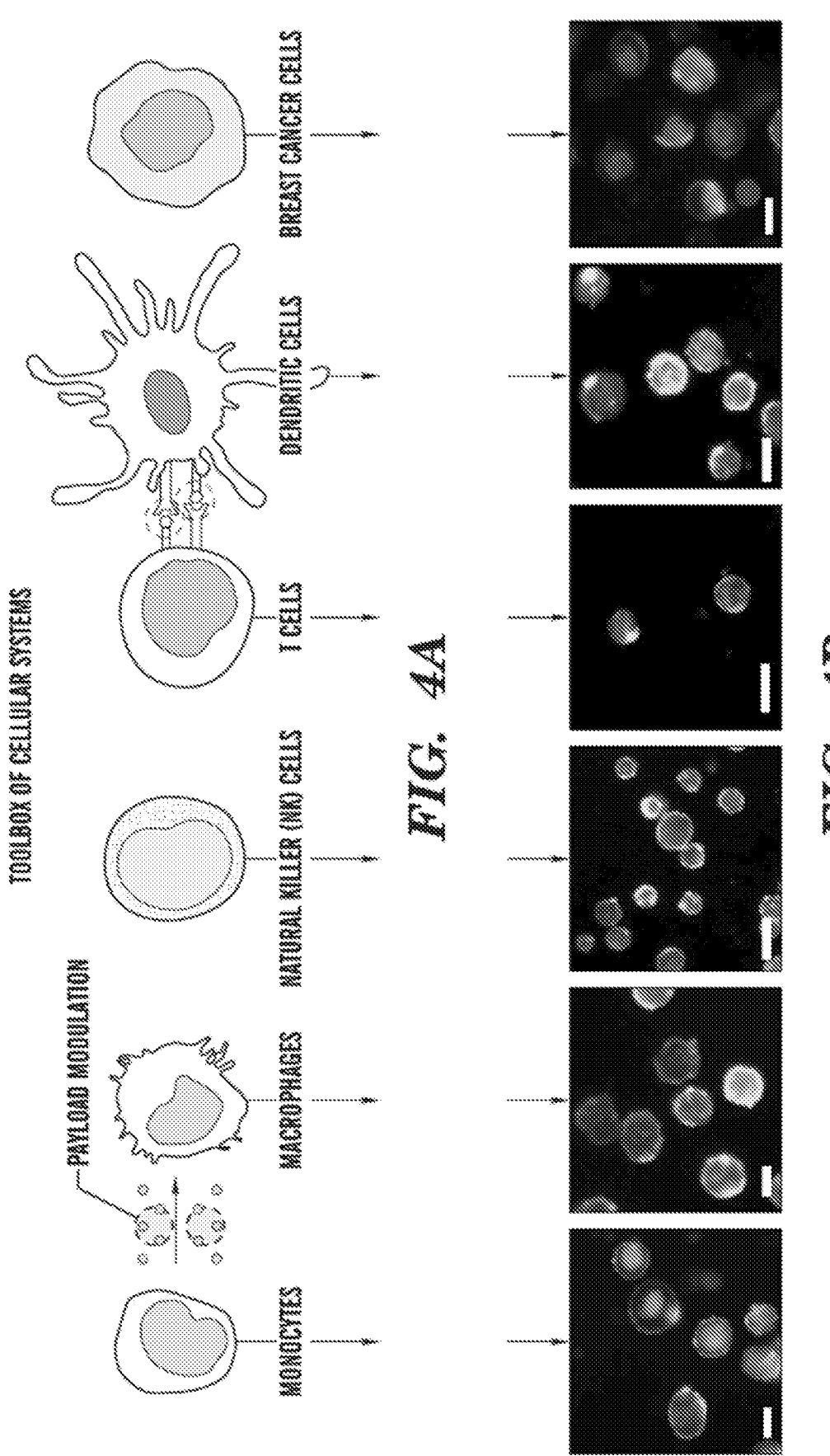
Figure 4G:
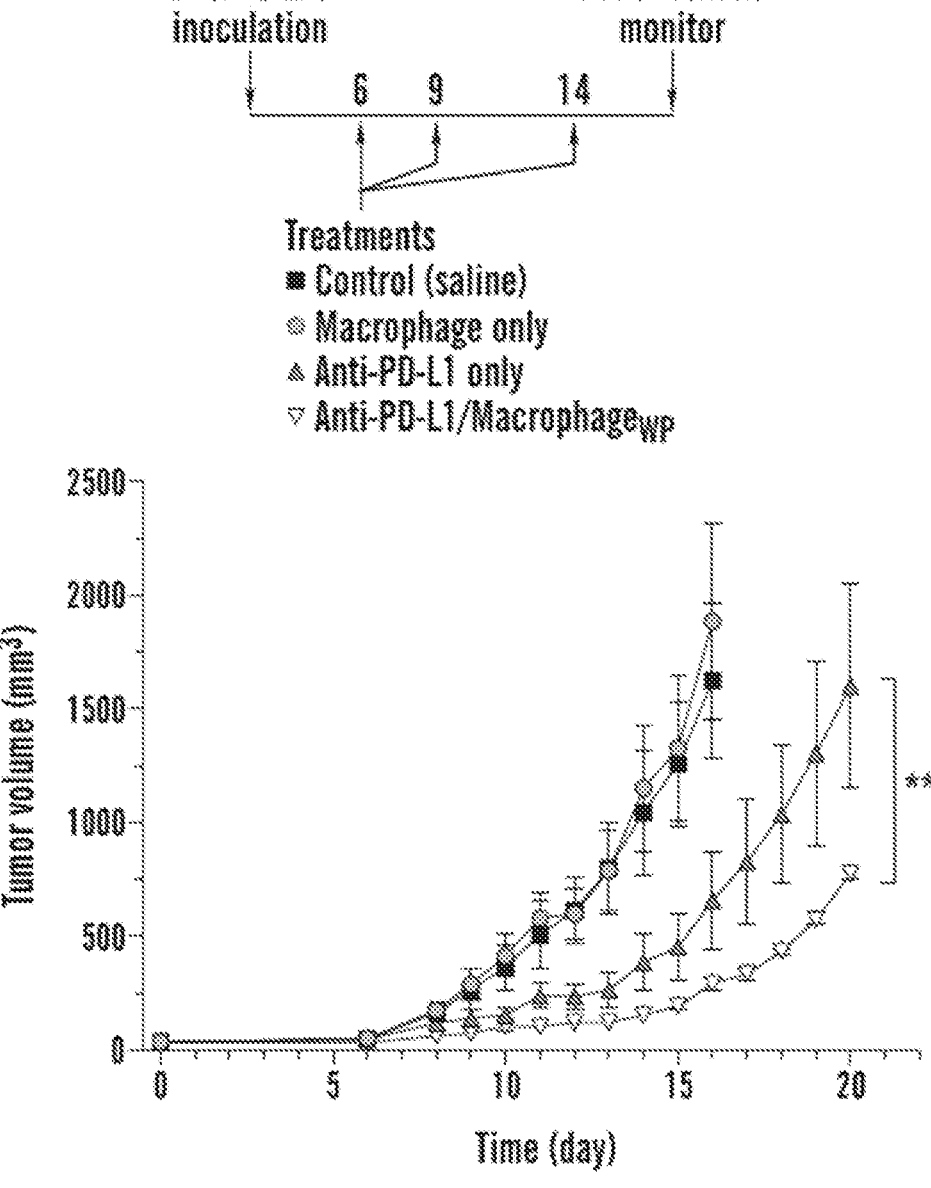
Figure 4H:
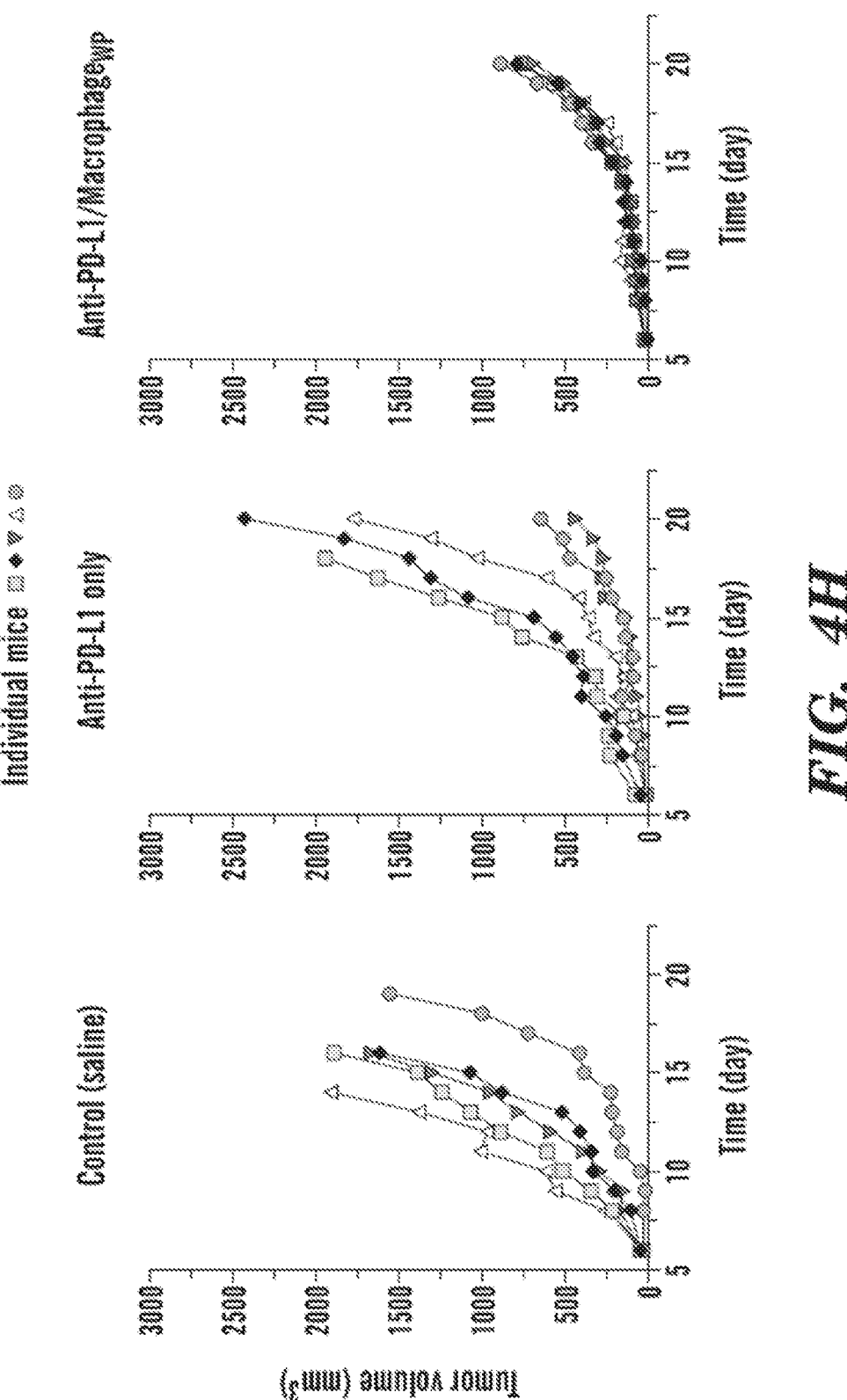

Cell-based therapies (e.g., adoptive cell transfer and stem cell treatments) have been regarded as a promising approach to treat cancer and, more increasingly, autoimmune diseases. Tunable engineering of cells intended for transplantation is vital to maximize the efficacy of the administered cell therapies (39). Common approaches for modulating immunosuppressive microenvironments, particularly within tumor sites, include targeting checkpoint pathways, modulating metabolic pathways, and generating cytokine-producing T cells (40, 41). These cellular modulation goals may be addressed by the present study of Cellwrap. In the case of using cells as delivery vehicles (e.g., monocytes, macrophages), one approach to accelerate the time needed for cell preparation is to efficiently load biomolecule and/or active agent payloads onto cells without affecting their intrinsic ability to home to specific tissues (42). For example, targeting monocyte differentiation pathways for specific macrophage phenotypes without adversely affecting their trafficking is necessary to achieve successful delivery. In the case of using transplanted cells (e.g., NK cells, T cells, and stem cells) as therapeutic entities, fine control over their activation and behavior allows for a personalized immunotherapeutic approach (43). Prominent strategies include adoptive cell transfer with tumor-infiltrating lymphocytes. CAR T cells, and T cell receptor gene therapy, all of which modify the immune system to recognize tumor cells and carry out an anti-tumor effector function. Transplanted T and NK cell therapies usually require engineering with an adjuvant biomolecule and/or active agent (e.g., IL-12, IL-15) to keep the cells active. FIG. 4A shows that the generalized Cellwrap toolbox can be applied to a variety of mammalian cells. We used Alexa 488-conjugated BSA as a model biomolecule and/or active agent for integration with a range of cell types, including dendritic cells, macrophages, NK cells, monocytes, and T cells. FIG. 4B illustrates the uniform and thin fluorescent layer on the surfaces of all types of cells, indicating the successful assembly of biomolecules on these cells and creation of at least five different types of biohybrid cellular systems with potentials of different biological functions.

Figure 21:
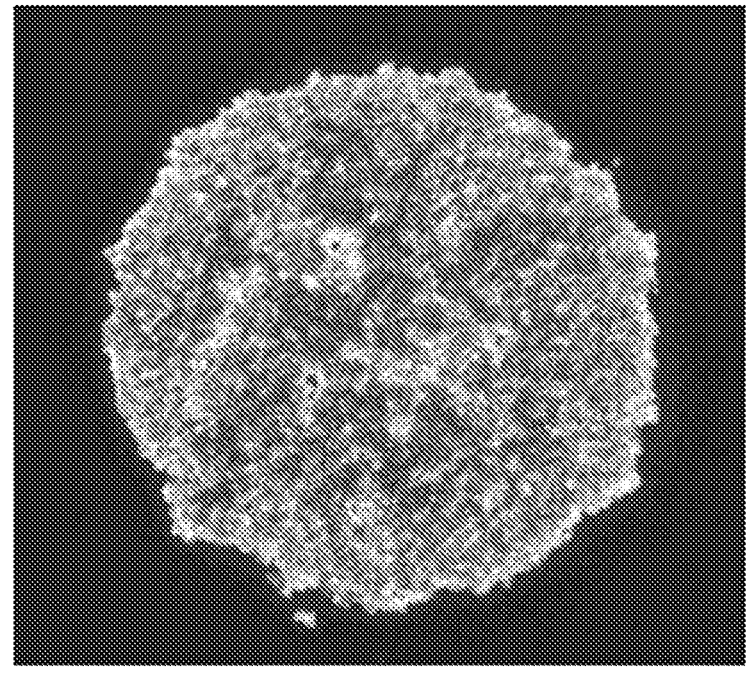
FIG. 21 depicts a bright-field microscopy image of 4T1 tumor spheroid. A compact cellular structure can be observed.
Figure 24:
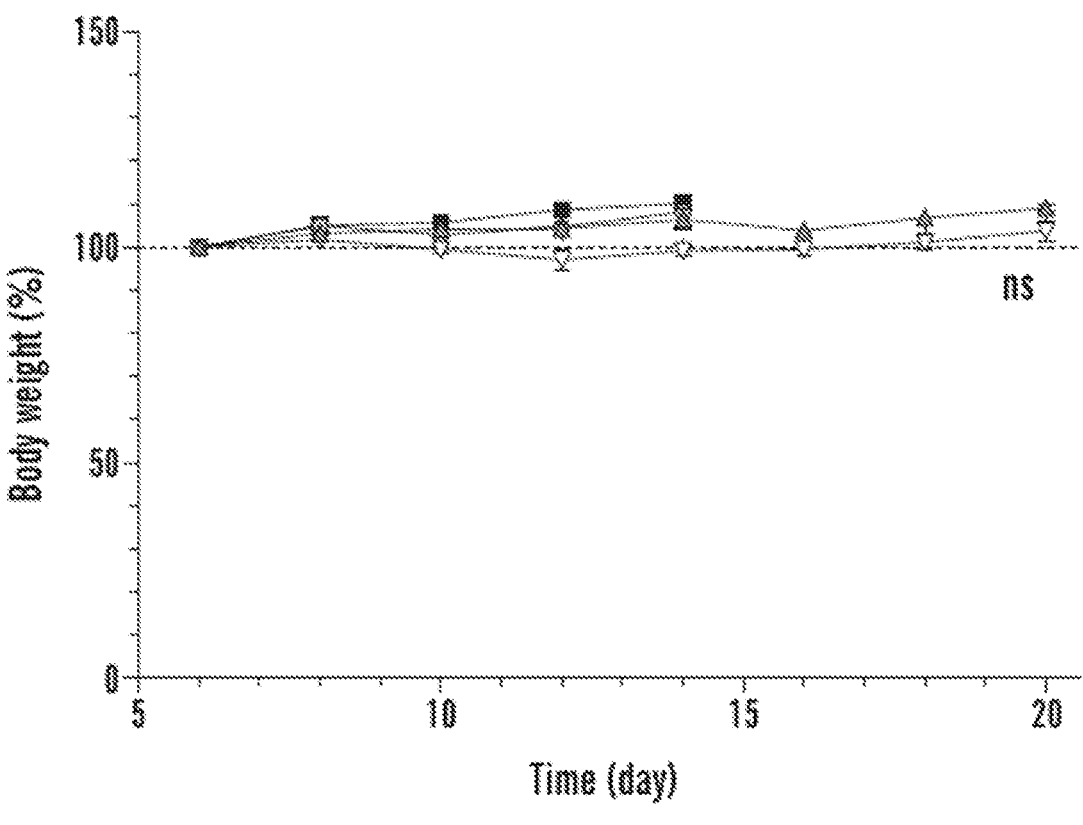
FIG. 24 depicts body weight per experimental group at the indicated time points.
Figure 25A:
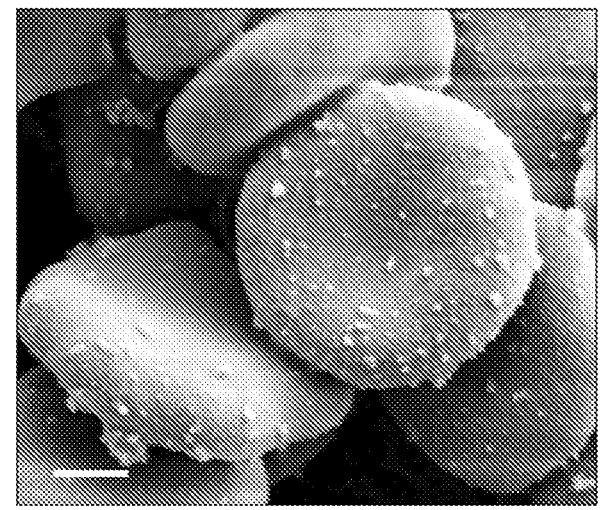
FIGS. 25A-25D demonstrate that AAV9 efficiently binds to RBC via a polyphenol-mediated approach.
Figure 25B:
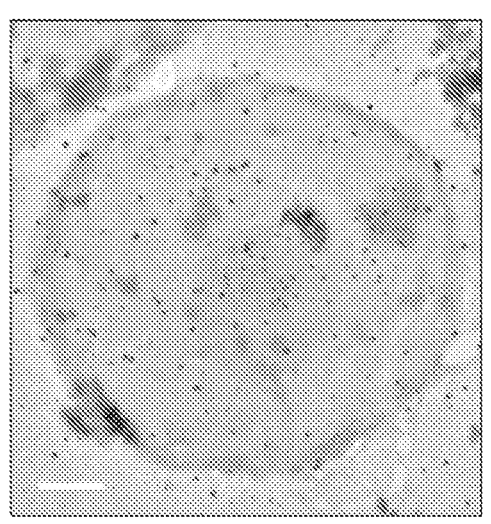
Figure 25C:
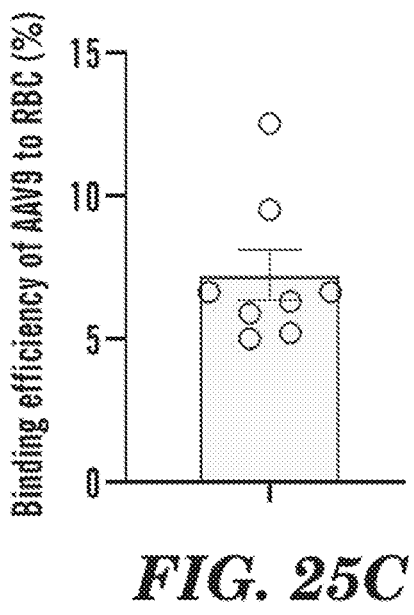
Figure 25D:
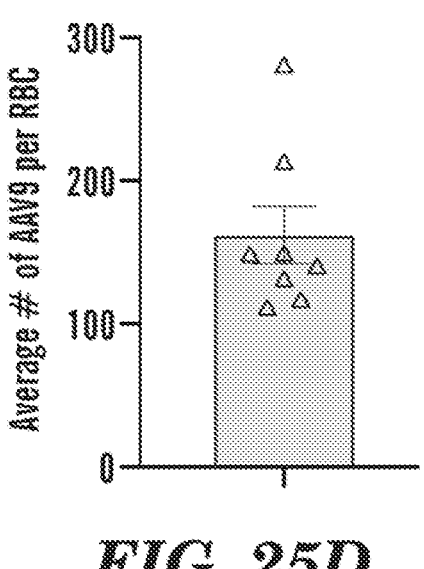
Figure 26E:
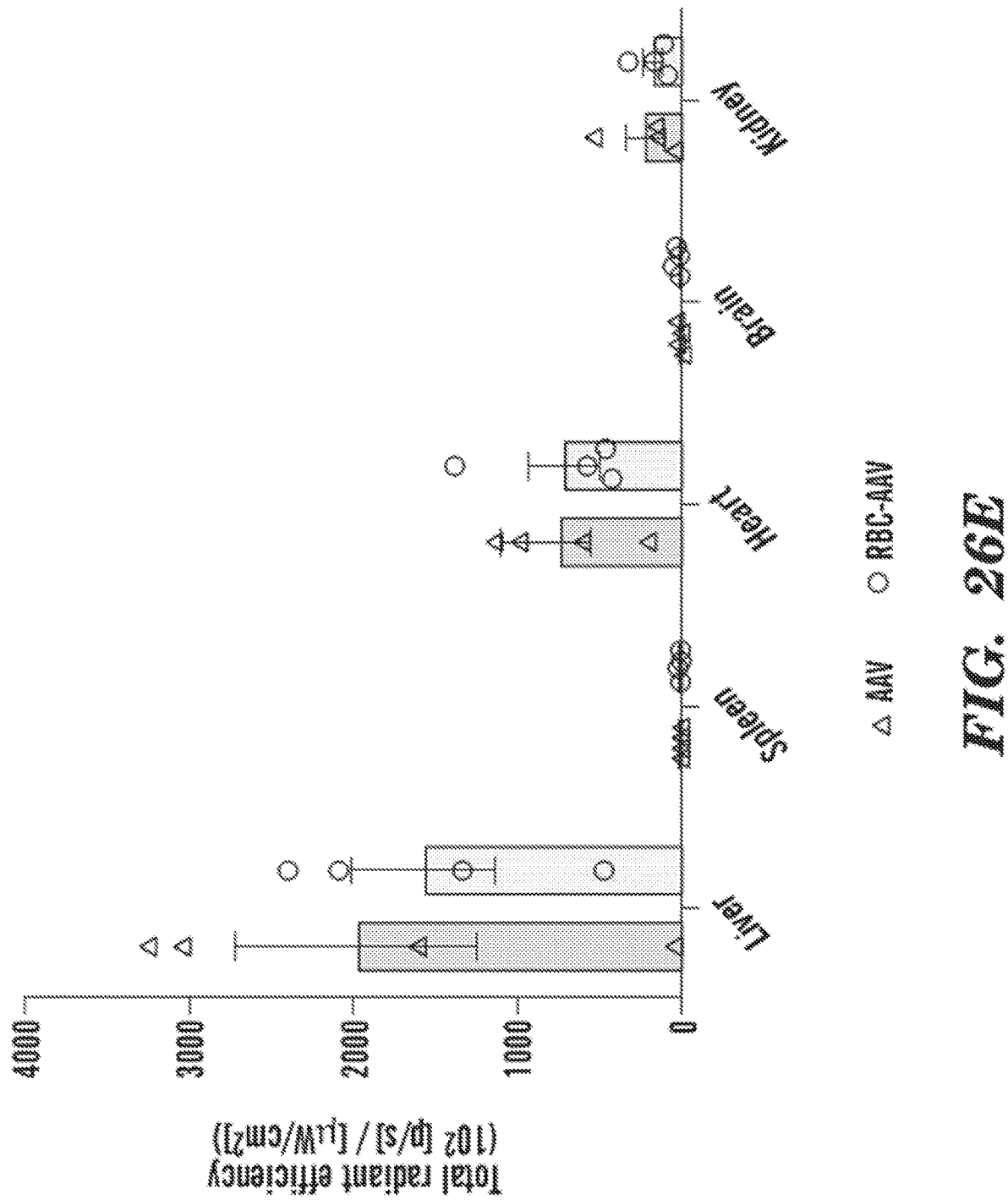
Figure 27A:
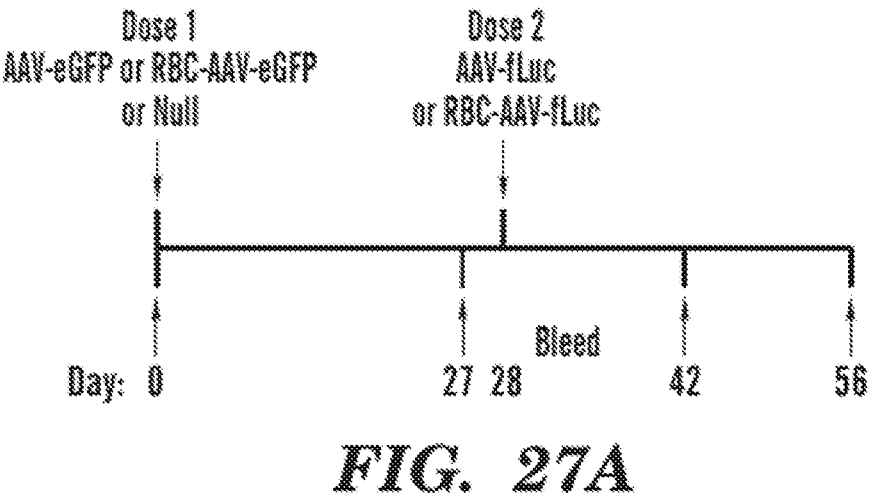
FIGS. 27A-27E demonstrate that RBC-AAV enabled AAV re-dosing and targeted gene expression in the lung in the presence of existing immune responses.
Figure 27B:
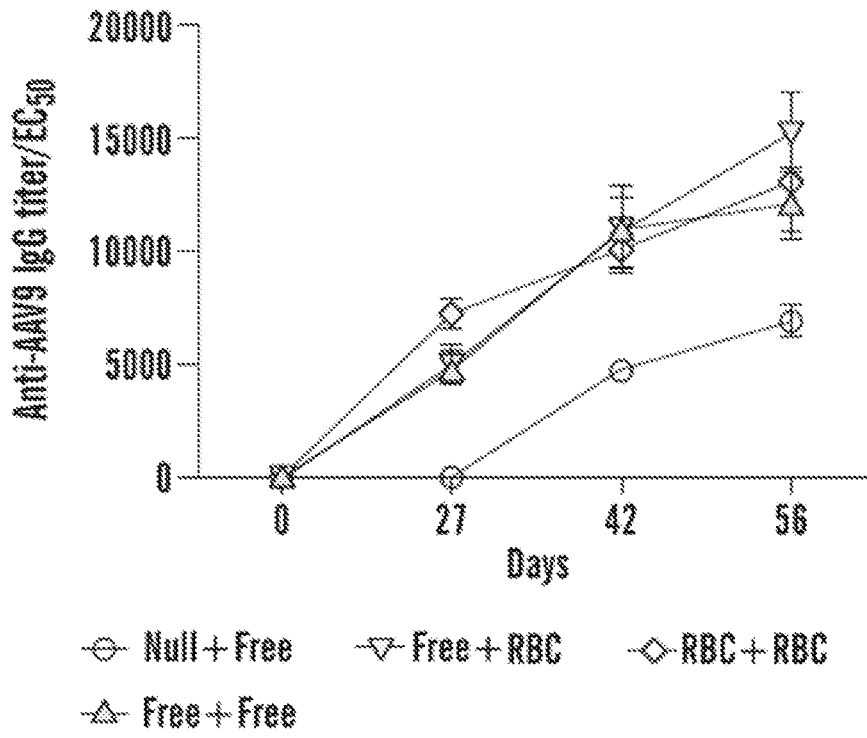
Figure 27C:
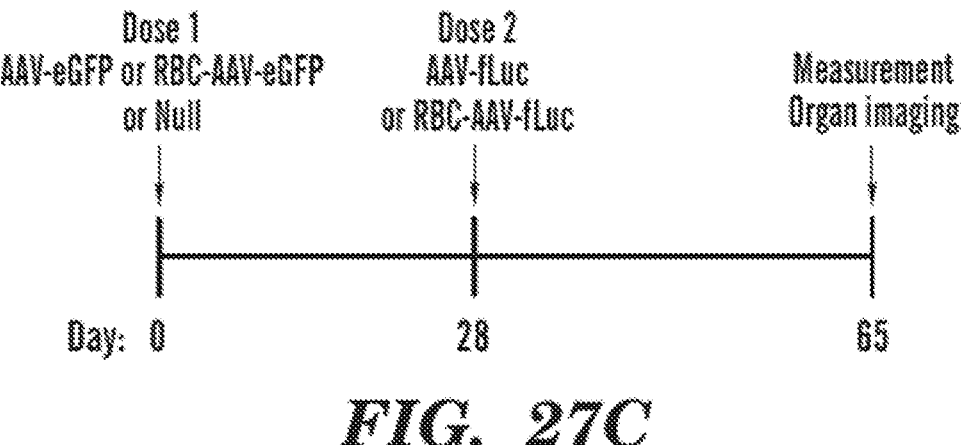
Figure 27D:
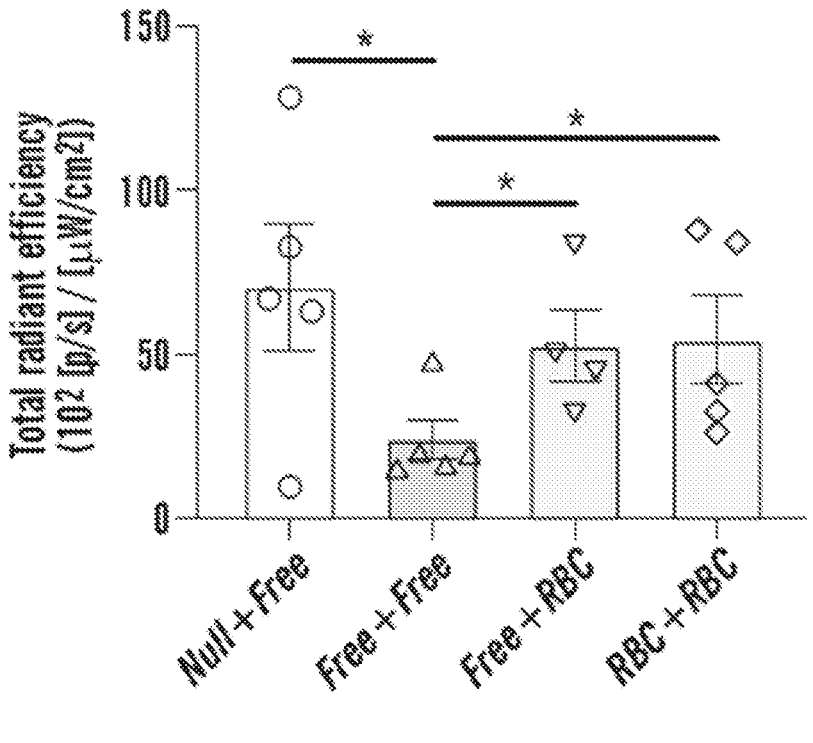
Figure 27E:
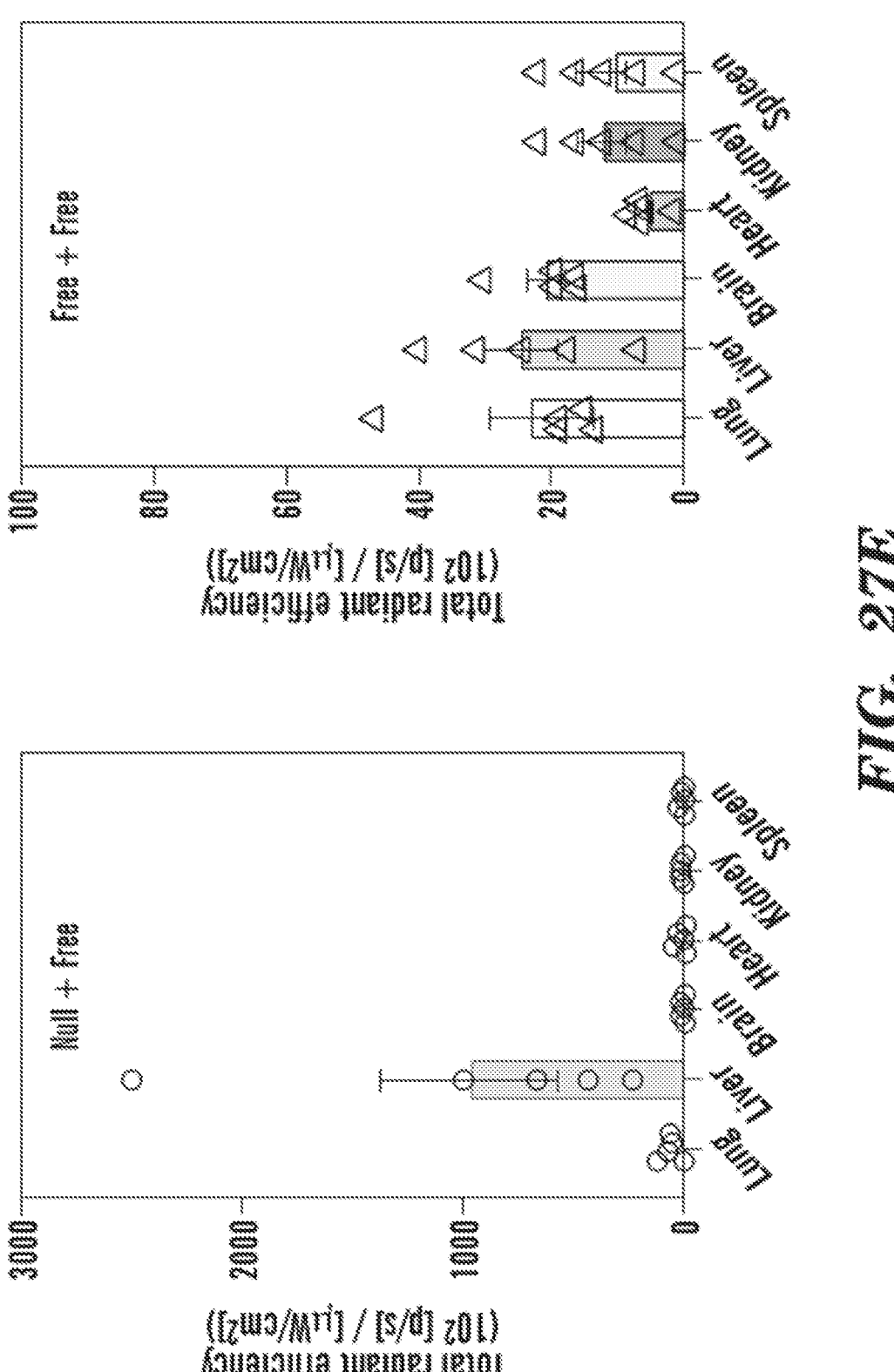
Figure 27E:
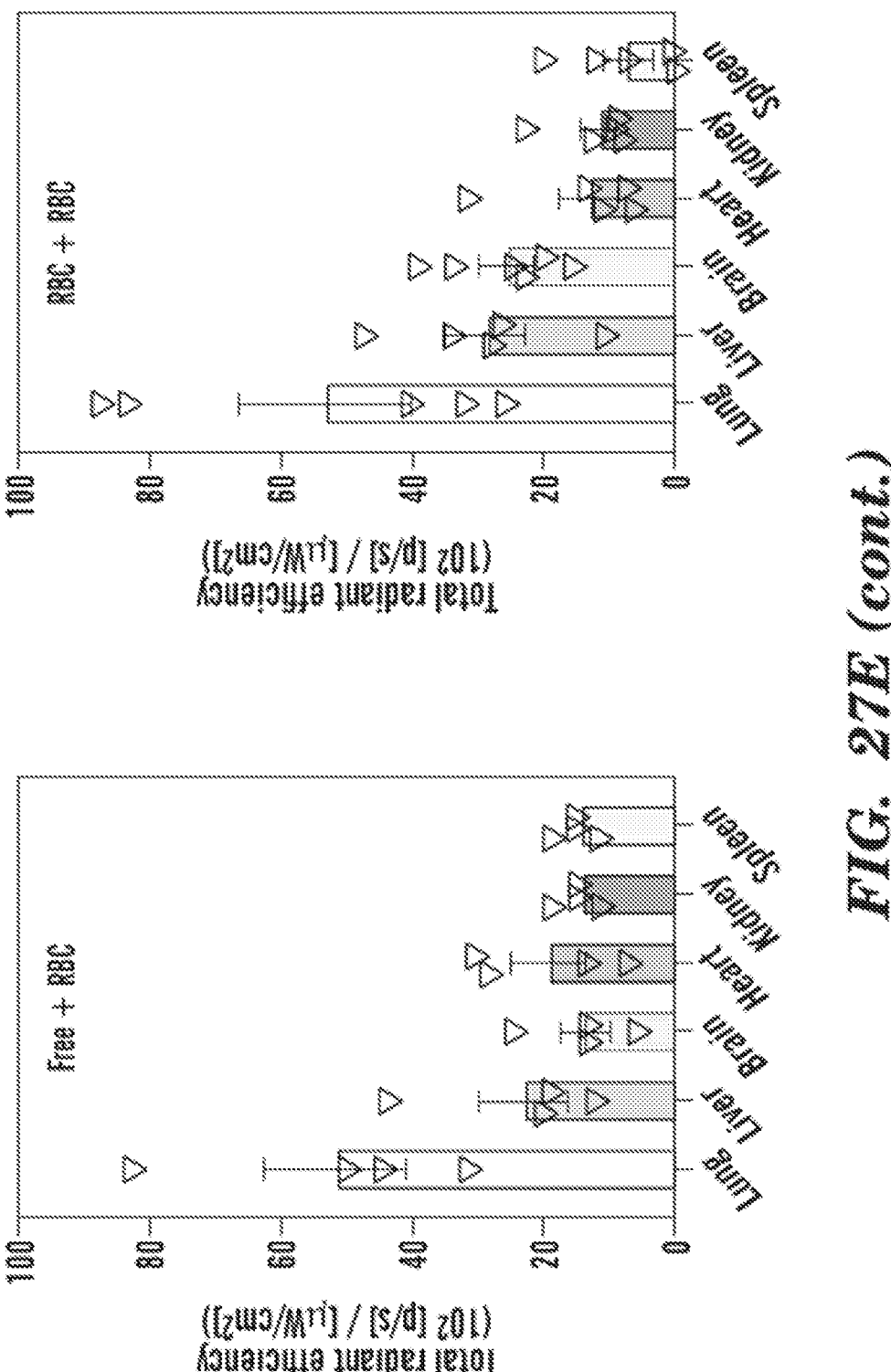

To confirm that the polyphenol-functionalized nanocomplexes do not prohibit cellular sensing mechanism, we prepared Macrophage$_{plex}$ and assessed their chemotaxis toward solid tumor spheroids. Here, we used the Macrophage$_{plex}$ to deliver an immune checkpoint inhibitor antibody (i.e., anti-PD-L1) into the tumor spheroid (FIG. 4C). FIG. 4D and FIG. 21 show the compact cellular structure of the 4T1 tumor spheroid, which generally leads to the challenge of drug delivery into the central area and formation of drug resistance. Interestingly, anti-PD-L1/Macrophage$_{plex}$ was able to deliver the anti-PD-L1 antibody to the tumor spheroid, even deeply into its center (FIGS. 4E and 4F). There was minimal penetration of fluorescence signal when free anti-PD-L1 antibodies were added into the tumor spheroid culture media (FIGS. 22A-22D). This demonstration indicates that the Macrophage$_{plex}$ has potential for achieving targeted delivery of therapeutic molecules for modulating the tumor microenvironments. The Cellwrap platform enables a customizable cell-engineering platform with flexible toolboxes of carried biomolecules and cells.

CONCLUSIONS

In summary, the modular engineering of Cellwrap offers a simple and adaptable method that can be rapidly prepared (less than 10 minutes) in which the biomolecules are simply mixed with polyphenols in an optimized stoichiometric ratio to form a nanoscale complexation, followed by subsequent assembly on the surfaces of various living cells. Engineered Erythrocyte$_{plex}$ exhibited the ability to selectively target capillary vascular structures, which could be useful for the effective delivery of therapeutic drugs to lung cancer or chronic respiratory infections. The engineered Erythrocyte$_{plex}$ only requires the direct assembly of polyphenol-functionalized nanocomplexes on erythrocytes, unlike previous nanoparticle-based systems. As another example, Macrophage$_{plex}$ integrated with anti-PD-L1 antibodies were able to penetrate into 4T1 breast cancer tumor spheroids through chemotaxis. This simple and generalizable approach presents a promising platform for a wide range of cell-based therapies and biohybrid cell engineering.

REFERENCES

1 Barker R. A., Drouin-Ouellet, J. & Parmar, M. Cell-based therapies for Parkinson disease-past insights and future potential. *Nature Rev. Neuro.* 11, 492 (2015).
2 Heathman, T. R. et al. The translation of cell-based therapies: clinical landscape and manufacturing challenges. *Regen. Med.* 10, 49-64 (2015).
3 Li, T., Dong, H., Zhang, C. & Mo, R. Cell-based drug delivery systems for biomedical applications. *Nano Res.* 11, 5240-5257 (2018).
4 Gong, X. et al. Emerging Approaches of Cell-Based Nanosystems to Target Cancer Metastasis. *Adv. Funct. Mater.*, 1903441 (2019).
5. Shi, Y. & Lammers, T. Combining Nanomedicine and Immunotherapy. *Acc. Chem. Res.* (2019).
6 Rosenberg, S. A. & Restifo, N. P. Adoptive cell transfer as personalized immunotherapy for human cancer. *Science* 348, 62-68 (2015).
7 Gill, S. & June, C. H. Going viral: chimeric antigen receptor T-cell therapy for hematological malignancies. *Immunol. Rev.* 263, 68-89 (2015).

8 Johnson, L. A. et al. Rational development and characterization of humanized anti-EGFR variant III chimeric antigen receptor T cells for glioblastoma. *Sci. Trans. Med.* 7, 275ra222-275ra222 (2015).
9 Chen, Z., Wang, Z. & Gu, Z. Bioinspired and Biomimetic Nanomedicines. *Acc. Chem. Res.* 52, 1255-1264 (2019).
10. Shields IV, C. W., Wang, L. L.-W., Evans, M. A. & Mitragotri, S. Materials for Immunotherapy. *Adv. Mater.*, 1901633 (2019).
11 Schultz, L. & Mackall, C. Driving CAR T cell translation forward. *Science translational medicine* 11, eaaw2127 (2019).
12 Zhang, L. et al. Tumor-infiltrating lymphocytes genetically engineered with an inducible gene encoding interleukin-12 for the immunotherapy of metastatic melanoma. *Clinic. Cancer. Res.* 21, 2278-2288 (2015).
13 Goldberg, M. S. Improving cancer immunotherapy through nanotechnology. *Nature Rev. Cancer,* 1-16 (2019).
14 Yoo, J.-W., Irvine, D. J., Discher, D. E. & Mitragotri, S. Bio-inspired, bioengineered and biomimetic drug delivery carriers. *Nature Rev. Drug Discover.* 10, 521 (2011).
15 Anselmo, A. C. et al. Delivering nanoparticles to lungs while avoiding liver and spleen through adsorption on red blood cells. *ACS Nano* 7, 11129-11137 (2013).
16 Tang, L. et al. Enhancing T cell therapy through TCR-signaling-responsive nanoparticle drug delivery. *Nature Biotech.* 36, 707 (2018).
17 Polak, R. et al. Liposome-Loaded Cell Backpacks. *Adv. Healthc. Mater.* 4, 2832-2841 (2015).
18 Stephan, M. T., Moon. J. J., Um, S. H., Bershteyn, A. & Irvine, D. J. Therapeutic cell engineering with surface-conjugated synthetic nanoparticles. *Nature Med.* 16, 1035 (2010).
19 Klyachko, N. L. et al. Macrophages with cellular backpacks for targeted drug delivery to the brain. *Biomaterials* 140, 79-87 (2017).
20 Zhang, Y., Li, N., Suh, H. & Irvine, D. J. Nanoparticle anchoring targets immune agonists to tumors enabling anti-cancer immunity without systemic toxicity. *Nature Comm.* 9, 6 (2018).
21 Brenner. J. S. et al. Red blood cell-hitchhiking boosts delivery of nanocarriers to chosen organs by orders of magnitude. *Nature Comm.* 9, 2684 (2018).
22 Zelepukin, I. et al. Nanoparticle-based drug delivery via RBC-hitchhiking for the inhibition of lung metastases growth. *Nanoscale* 11, 1636-1646 (2019).
23 Zhu, W. et al. Modular Metal-Organic Polyhedra Super-assembly: From Molecular-Level Design to Targeted Drug Delivery. *Adv. Mater.* 31, 1806774 (2019).
24 Guo, J. et al. Modular assembly of superstructures from polyphenol-functionalized building blocks. *Nature Nanotech.* 11, 1105 (2016).
25 Guo, J. et al. Light-driven fine chemical production in yeast biohybrids. *Science* 362, 813-816 (2018).
26 Lee, H. A., Ma. Y., Zhou, F., Hong, S. & Lee, H. Material-Independent Surface Chemistry beyond Polydopamine Coating. *Acc. Chem. Res.* 52, 704-713 (2019).
27 Villa, C. H., Anselmo, A. C., Mitragotri, S. & Muzykantov, V. Red blood cells: Supercarriers for drugs, biologicals, and nanoparticles and inspiration for advanced delivery systems. *Adv. Drug. Deliver. Rev.* 106, 88-103 (2016).
28 Qiu. Y., Myers, D. R. & Lam, W. A. The biophysics and mechanics of blood from a materials perspective. *Nature Rev. Mater.,* 1 (2019).

29 Shi, J. et al. Engineered red blood cells as carriers for systemic delivery of a wide array of functional probes. *Proc. Natl. Acad. Sci. USA* 111, 10131-10136 (2014).

30 Mitragotri, S., Burke, P. A. & Langer, R. Overcoming the challenges in administering biopharmaceuticals: formulation and delivery strategies. *Nature Rev. Drug Discover.* 13, 655 (2014).

31 Pishesha, N. et al. Engineered erythrocytes covalently linked to antigenic peptides can protect against autoimmune disease. *Proc. Natl. Acad. Sci. USA* 114, 3157-3162 (2017).

32 Alapan. Y. et al. Soft erythrocyte-based bacterial microswimmers for cargo delivery. *Sci. Robot.* 3, eaar4423 (2018).

33 Shin. M. et al. Targeting protein and peptide therapeutics to the heart via tannic acid modification. *Nature Biomed. Eng.* 2, 304 (2018).

34 Chen, W. et al. Unidirectional presentation of membrane proteins in nanoparticle-supported liposomes. *Angew. Chem. Int. Ed.* 58, 9866-9870 (2019).

35 Guo, J., Suma. T., Richardson. J. J. & Ejima, H. Modular Assembly of Biomaterials Using Polyphenols as Building Blocks. *ACS Biomater. Sci. Eng.* (2019).

36 Usman. W. M. et al. Efficient RNA drug delivery using red blood cell extracellular vesicles. *Nature Comm.* 9, 2359 (2018).

37 Qi, Q. M. et al. In Vitro Measurement and Modeling of Platelet Adhesion on VWF-Coated Surfaces in Channel Flow. *Biophys. J.* 116, 1136-1151 (2019).

38 Rivera, R. G. H., Zhang, X. & Graham, M. D. Mechanistic theory of margination and flow-induced segregation in confined multicomponent suspensions: simple shear and Poiseuille flows. *Phys. Rev. Fluids* 1, 060501 (2016).

39 Dellacherie. M. O., Seo. B. R. & Mooney, D. J. Macroscale biomaterials strategies for local immunomodulation. *Nature Rev. Mater.,* 1 (2019).

40 Mardiana. S., Solomon. B. J., Darcy. P. K. & Beavis, P. A. Supercharging adoptive T cell therapy to overcome solid tumor-induced immunosuppression. *Sci. Trans. Med.* 11, eaaw2293 (2019).

41 Sun, Q. et al. Nanomedicine and macroscale materials in immuno-oncology. *Chem. Soc. Rev.* 48, 351-381 (2019).

42 Anselmo, A. C. et al. Monocyte-mediated delivery of polymeric backpacks to inflamed tissues: a generalized strategy to deliver drugs to treat inflammation. *J. Control. Release* 199, 29-36 (2015).

43 Zhu, W. et al. SupraCells: Living Mammalian Cells Protected within Functional Modular Nanoparticle-Based Exoskeletons. *Adv. Mater.,* 1900545 (2019).

Example 2

General Materials

Tannic acid (TA), iron (III) chloride hexahydrate ($FeCl_3 \cdot 6H_2O$), 96% ethanol laboratory reagent, AlexaFluor 488 bovine serum albumin (BSA), AlexaFluor 488 ovalbumin (OVA), AlexaFluor 647 ovalbumin (OVA), biotin-4-fluorescein, FITC (Fluorescein)-conjugated lectin, and phosphate-buffered saline (PBS) were purchased from Sigma-Aldrich (U.S.A.). FITC anti-human CD274 (B7-H1, PD-L1) antibody was purchased from BioLegend (U.S.A.). Cholera toxin subunit b (recombinant) Alexa Fluor 488 conjugate, Alexa Fluor 488 streptavidin conjugate, Dulbecco's phosphate buffered saline (DPBS), pH 7.4 were purchased from Thermo Fisher Scientific (U.S.A.). 200 nm carboxylated polystyrene beads was purchased from Polysciences (U.S.A.). NaCl was purchased from Fisher scientific (USA), 10% Formalin was purchased from VWR (U.S.A.). Anti-mouse CD31, anti-mouse CD68, anti-rabbit AlexaFluor 488 were purchased from Abcam (U.S.A.). DNA-pEGFP-N1 (4733 basepairs; entire sequence can be found on the world wide web at addgene.org/vector-database/2491/). The plasmid DNA was labeled with a fluorophore (MFP488) with Mirus Bio kit. The plasmid can be used to express EGFP protein when successfully transfected. However, labeling step will no longer enable pDNA to be expressed, mRNA encoding EGFP protein (OZ Biosciences. U.S.A.) was labeled with a fluorophore (Cy5) with Mirus Bio kit. mRNA labeling may likely have denatured mRNA because mRNA is very vulnerable to RNase-mediated degradation. The DNA and mRNA were used as model nucleic acids for the engineering of Cellwrap. All of these materials were used as received. High-purity Milli-Q (MQ) water with a resistivity of 18.2 MC/cm was obtained from an inline Millipore RiOs/Origin water purification system. All solutions were freshly prepared for immediate use in each experiment.

Preparation of Erythrocytes for Cellwrap Preparation

CJ7BL/6 female mice were purchased from the Charles River Laboratory (Wilmington, MA). Whole blood was collected from healthy CJ7BL/6J mice (50-56 days old). Mice were sacrificed by $CO_2$ overdose and blood (400 uL-600 μL) was collected from inferior vena cava (IVC) using a 25G needle and placed in an ImL heparin coated tubes (BD Microtainer). Blood was centrifuged at 1000 g for 10 min at 4° C. to remove plasma as well as platelets and white blood cells. Isolated erythrocytes (RBCs), transferred into 15 mL conical tube, and washed by adding 12 mL of ice cold 1× Dulbecco's-Phosphate-Buffered-Saline (DPBS), pH 7.4. RBC suspension was then mixed by gently pipetting up and down extensively; centrifuged at 650 g, 15 min, at 4° C. and supernatant was discarded. This wash step was repeated three times.

Preparation of Mammalian Cells for Cellwrap Preparation

All experiments were performed according to the approved protocols by the Institutional Animal Care and Use Committee (IACUC) of the Faculty of Arts and Sciences (FAS), Harvard University, Cambridge.

Monocytes; $5 \times 10^5$ primary human monocytes (BioVT) were thawed and resuspended in RPMI-1640 media supplemented with 12% FBS, and 1% penicillin and streptomycin (Pen-Strep) through two rounds of centrifugation at 500×g for 15 minutes. The monocytes were separated into 5×104 cells/group, centrifuged at 300×g for 7.5 minutes, and resuspended in 500 uL of PBS.

Breast cancer cells; $4 \times 10^6$ murine triple negative breast carcinoma cells (4T1, ATCC) were thawed and resuspended in 50 mL DMEM supplemented 10% FBS and 1% Pen Strep. Cells were cultured in a humidified incubator maintained at 37° C. and 5% CO2. Cells were passaged twice (48 hours between passages) and released via trypsin, centrifuged, and resuspended in PBS before the assembly of cellwrap.

Macrophages (RAW 264.7), dendritic cells (JAWSII), and natural killer cells (NK-92) were obtained from ATCC. They were cultured in a humidified incubator maintained at 37° C. and 5% $CO_2$. RAW 264.7 macrophages were cultured in DMEM media supplemented with 10% FBS and 1% Pen-Strep. JAWSII dendritic cells were cultured in Alpha-MEM media supplemented with 20% FBS, 1% Pen-Strep, and 5 ng/mL murine GM-CSF. NK-92 natural killer cells were cultured in Alpha-MEM media supplemented with 0.2 mM inositol, 0.1 mM 2-mercaptoethanol, 0.02 mM folic acid, 100 U/mL IL-2, 1% Pen-Strep, 12.5% horse serum and 12.5% fetal bovine serum. Mouse CD8 T cells were isolated from Balb/c mouse spleen using a MojoSori™ Mouse CD8 T Cell Isolation Kit obtained from BioLegend according to a protocol provided by the manufacturer.

General Characterization Instruments and Software 3D-reconstructed florescence microscopy imaging was performed using a Upright Zeiss LSM 710 NLO ready confocal microscope, with a set of standard filters for DAPI/CFP/FITC/AF488/AF568/Cy5/AF647. Image processing and 3D models were analyzed and generated with Imaris (Bitplane) software using the maximum intensity projection. Scanning electron microscopy (SEM) images were obtained on a ZEISS FESEM Ultra-55 field-emission scanning electron microscope (Carl Zeiss, Germany), operating at an accelerating voltage of 5-10 kV. UV-Visible absorption and fluorescence measurements were conducted on an Infinite M200 PRO microplate reader (Tecan Group, Switzerland). Transmission electron microscopy (TEM) were performed on a JEOL JEM-1400 TEM instrument, operating at a voltage of 100 kV (JEOL USA, Inc.). Circular dichroism spectroscopy (Jasco Inc., J-815) was used to characterize the biomolecule and/or active agent structure. Particle zeta potential was measured by dynamic light scattering (DLS) on Malvern Zetasizer (Malvern, U.S.A.). In vivo animal florescence imaging was conducted by Small Animal Imaging (IVIS Spectrum).

SEM and TEM Sample Preparation

Erythrocytes and Cellwrap suspensions (2.0 μL) were allowed to air-dry on Piranha-cleaned silicon wafers and Formvar carbon-coated gold grids (Piranha solution; $H_2SO_4$ (30%)/$H_2O_2$, 7:3 v/v; Piranha solution is highly oxidizing and corrosive! Extreme care should be taken during preparation and use). For the preparation of 3D-structured shape-maintained erythrocyte samples, formalin treatment of erythrocyte samples was applied.

Preparation of Cellwrap

Formation of Polyphenol-Functionalized Biomolecular Nanocomplexes

All solutions were freshly prepared and filtered through 0.2 μm pores for immediate use. The standard preparation process is described as follows. 3.0 gL of biomolecule and/or active agent solutions (e.g., proteins. DNA, and mRNA) (0.1-4.0) mg/mL) and 10 uL of tannic acid (10 mg/mL) solutions were added to a 400 gL PBS solution. The mix solution was incubated for 60 s to facilitate the interaction between polyphenols and biomolecules to form polyphenol-functionalized biomolecular nanocomplexes. The galloyl and catechol moieties clustered with biomolecules can from multiple interactions with cell surface, providing driving forces for the biomolecular assembly on cells. The biological activity of biomolecules can be maintained after the polyphenol-based functionalization. Circular dichroism spectroscopy and ELISA were used to determine the intact structure of biomolecules through the functionalization process.

Assembly of Nanocomplexes on the Surfaces of Cells

The assembly of biomolecules on cell surface can occur after mixing the abovementioned 400 gL PBS solution of polyphenol-functionalized biomolecular nanocomplexes with 100 gL of cell suspensions (e.g., erythrocytes, macrophages. NK. T cells, and cancer cells). The ratio of biomolecules and cell numbers was varied based on different biomolecules and cell types, and can be optimized to avoid or minimize particle aggregation if desired. Then, the assembly of biomolecules on cells was achieved by adding 3.0 pL $FeCl_3$ solution and an equal volume (i.e., 500 gL) of PBS buffer solution (pH 7.4, 10 mM). Cellwrap can be obtained after washing with PBS water for 2-3 times to remove the excess biomolecular nanocomplexes and polyphenols. The centrifugation speeds used for Cellwrap were varied based on cell types and an optimized centrifugation speed of 100 g, 5 min was used in this study.

Release of Carried Biomolecules from Cellwrap

Erythrocyte$_{plex}$ integrated with AlexaFluor 488-conjugated BSA were resuspended in 1 mL PBS (+10% glucose) and FBS media, then and incubated at 37° C. on a tube revolver. At regular time points, the Erythrocyte$_{plex}$ were centrifuged at 100 g for 5 mins and the supernatant was collected for analysis. The Erythrocyte$_{plex}$ were further resuspended in 1 mL of fresh release media and incubated at 37° C. until the next time point. Samples were taken at 0, 4, 8, 18, and 24 h after starting the incubation. The cumulative release in each release media was quantified by florescence intensity.

Animal Studies

All animal studies were carried out in strict accordance with Guide for the Care and Use of Laboratory Animals as adopted by National Institute of Health, approved by Harvard University IACUC. Mice were housed in cages with free access to water and food, located in a well-ventilated temperature-controlled room between 18-23° C. with relative humidity ranging from 40-60% under a 12-hour light/dark period).

Biocompatible Test of Cell$_{/Flex}$ on Erythrocytes

Agglutination of OVA/Erythrocyte$_{plex}$

Murine erythrocyte and OVA-erythrocyte$_{plex}$ suspensions (150 μL) at 1% Hematocrit were dispensed onto a 96 U-shaped plate and visually accessed after 24 h at room temperature after RBC suspension had fully sedimented. 200 nm carboxylated polystyrene beads (Polysciences), adsorbed onto erythrocytes at a (1:50; RBC:NP) was used to induce clumping of RBCs, resulting in aggregates. These aggregates are associated with hematological diseases.

Osmotic Fragility of OVA/Erythrocyte$_{plex}$

Isolated naive erythrocytes and OVA-Erythrocyte$_{plex}$ suspensions (50 μl, of 10% Hematocrit) were placed in various salt concentrations, ranging from 0 mM to 150 mM at 37° C., at a final concentration of 1% Hematocrit. Suspensions were mixed gently with a 1 mL micropipet and immediately centrifuged at 13,400 g for 4 min and absorbance of supernatant (100 μL) was read at 540 mm by SpectraMax 13 plate reader (Molecular Devices) plate reader. RBC suspension was used as 100% lysis.

Osmotic Fragility Under Low Shear Stress of OVA/Erythrocyte$_{plex}$

Low shear stress fragility assay was performed as previously reported. Briefly, 400 μL of naive erythrocytes and OVA-Erythrocyte$_{plex}$ suspensions, at 1.0% hematocrit in DPBS, were rotated at 37° C. for 0.08 h, 0.5 h, 1 h, 2 h, 4 h, and 24 h. In addition, both Naïve RBC and RBC$_{plex}$ suspensions were rotated for less than a second (deemed at—0 h). Suspensions were centrifuged immediately at 13,400 g for 4 min and the absorbance of supernatant (100 μL) was read at 540 nm by SpectraMax 13 plate reader (Molecular Devices). Each sample in water was used at 100% lysis.

In Vivo Biodistribution of OVA/Erythrocyte$_{plex}$

Female 50-56 days old C57BL/6 mice (n=3-6 per group) were administered intravenously using a with OVA-Erythrocyte$_{plex}$ coated with 30 ug/mL OVA. Mice were sacrificed by $CO_2$ overdose at different time points: 0.08 h, 0.5 h, 1 h, 2 h, 6 h, 12 h, and 24 h after intravenously injection and blood samples (200 uL) were collected from the inferior vena cava (IVC) in heparin coated tubes (BD Microtainer). Blood, as well as heart, lung, liver, spleen, kidneys, and brain were harvested. Each organ was placed in a 6 well tissue culture plate (Falcon); blood (50 µL) was placed in a heparinized microcapillary tube (Drummond Scientific) and far red fluorescence signal for each organ was imaged using Perkin Elmer IVIS small animal imaging system. Far red signals were quantified using LivingImage software.

Histology and Confocal Microscopy of OVA/Erythrocyte$_{plex}$

Lungs from mice that were sacrificed 0.08 h, 6 h, and 24 h after intravenous injection were fixed in 10% formalin (VWR) and given to the Harvard Histology Core in the Department of Stem Cell and Regenerative Biology for processing. Briefly lung tissues were embedded in paraffin and slice tissues (5 microns) were stained with anti-mouse CD31 (Abcam) as well as anti-mouse CD68 (Abcam) overnight, both at dilution of 1:50. Anti-rabbit AlexaFluor 488 (Abcam) was then used at a dilution of 1:500 to probe both anti-mouse CD3 1 and anti-mouse CD68 All sections were then imaged using LSM 700 confocal (Zeiss) at Harvard Center for Biological Imaging.

Flow Cytometry of OVA/Erythrocyte$_{plex}$

Murine Erythrocyte and OVA-Erythrocyte$_{piex}$ suspensions (5 tit) at 10% Hematocrit were added to 995 µL of PBS, gently vortexed, and ran on BD LSRFortessa (Biosciences) cell analyzer, gated at 10.000 events. Data was analyzed using FCS Express Version 6 DeNovo Software.

Biomimetic Microfluidic Experiments Microfluidic Devices Design

Microfluidic chip devices were obtained from Syn Vivo, Inc. (Huntsville, AL). The device consisted of three independent and identical square channels which are 100 µm in both width and depth (FIG. 14). Each channel was subject to physiological fluid flow conditions controlled by a Harvard Apparatus Pump 11 Pico Plus Elite.

Culture of Human Umbilical Vein Cells

The human umbilical vein cell line. EA.hy926 was obtained from ATCC (CRL-2922) and maintained with Dulbecco's Modified Eagle's Medium supplemented with 10% fetal bovine serum (FBS) and 1% Penicillin—Streptomycin. Cells were cultured on tissue culture flasks and incubated at 37 C, 95% humidity and 5% CO2 until confluent (FIG. 15). Cells were used between passage 8 and 12.

Culture of Endothelial Cells in Microfluidic Devices

To facilitate endothelial cell attachment, fibronectin (200 µg/mL) was injected into each channel and allowed to incubate for 1 hr at 37 C and 5% CO2 (doi: 10.1002/btm2.10126). The entire device was then perfused with cell culture media and primed using inert N2 gas at 6 PSI for 1 hr. 90% Confluent endothelial cells were trypsinized and resuspended in cell culture media at $10^7$ cells/ml. Cell suspension was injected into each channel at 2 µL/min and placed inside the incubator upside down to facilitate attachment to the upper PDMS regions of the channel. After 3 hours, the entire device was perfused with cell culture media at 2 µL/min and the cellular seeding process was repeated using an identical cell culture flask. The device was placed in the upright position in the incubator for 1 hr followed by media perfusion. The perfusion of cell culture media was repeated daily using an increased serum concentration of 20% FBS. Each device was maintained for three days before performing perfusion chamber experiments (FIG. 16).

Perfusion Chamber Experiments

Suspensions of red blood cells were flown into microfluidic channels at a constant injection rate of 100 µL/min (average wall shear rate=8.89*$10^3$/s, average wall shear stress=10.7 N/m²). The microfluidic device was visualized under a Zeiss Axio ZI Observer inverted microscope with a 10× objective. Brightfield (FIGS. 9A-=9, 10) and green fluorescence images (Colibri LED, 470 nm) were taken using a Hamamatsu Orca-Flash 4.0 sCMOS camera. Each perfusion experiment was performed for 30 seconds to ensure that steady state distribution of red blood cells was reached.

Visualization of Endothelial Cells with Actin Stain

4% PFA was injected into all device channels at 2 µL/min and incubated at room temperature for 15 min. After perfusion with DPBS, the entire device was perfused with 0.2% Triton X100 in DPBS and incubated at room temperature for 10 min. The device was again washed with DPBS and stained with Thermofisher ActinRed™ 555 Ready Probes™ (2 drops per ml of DPBS) at room temperature for 30 min. The device was perfused with DPBS and imaged using a Zeiss TIRF/LSM 710 confocal microscope with a 32× water immersion objective and a 488 nm laser (FIG. 17).

Computational Simulations and Modeling of Erythrocytepiex

Based on previous theoretical models[1,2], we consider the mixture of red blood cells as a dilute suspension of deformable particles (radius a, shear modulus G) with total volume fraction (hematocrit)

$$\bar{\phi}=10\%.$$

Their motion in a microchannel or in the microvasculature can be approximated as flowing in a slit bounded by two walls at y=0 and y=2H and unbounded in x and z. We consider pressure-driven flow in the channel and thus the local shear rate can be described as:

$$\gamma(y) = \gamma_{wall}\left(1 - \frac{y}{H}\right)$$

Under physiological flow conditions, the Reynolds number is very small and thus inertia can be neglectee[2]. The flow viscous effect relative to the deformability of red blood cells can be described by the Capillary number Ca:

$$Ca = \frac{\mu\gamma_{wall}a}{G}$$

The number density of red blood cells n is assumed to be only a function of y. We neglect Brownian diffusion due to the size of red blood cells. In the dilute limit, we only consider binary hydrodynamic interactions which result in shear-induced diffusion $J_{diffusion}$[3,4]. Due to the deformability of red blood cells, they migrate away from the wall under stokes flow with a velocity $v_{lift}(y)$, generating a lift flux $J_{lift}$[5]. In addition to $J_{lift}$ and $J_{diffusion}$, MPN-coated red blood cells also adhere to channel walls at a rate $r_{aasorption}$ which results in a surface number density of red blood cells $n_s$ at y=0 and y=2H. The evolution of the red blood cell distribution inside the channel can thus be described by the following equation:

$$\frac{\partial n}{\partial t} = -\frac{\partial}{\partial y}(J_{lift} + j_{diffusion}) - r_{adsorption}$$

We made the equation above dimensionless using the red blood cell radius a and the wall shear rate $\gamma_{wall}$ to arrive at the following equation as shown in FIG. 3I:

$$\frac{\partial \phi(y)}{\partial t} = -\frac{\partial}{\partial y}(J_{lift} + J_{diffusion}) - R_{adsorption}$$

63

According to previous work[2], the lift flux can be written as:

$$J_{lift} = \frac{Ca\left(1 - \frac{y}{C}\right)}{\kappa_1 + Ca\left(1 - \frac{y}{C}\right)}\left[\kappa_w\left(1 - \frac{y}{C}\right)\left(\frac{1}{y^2} - \frac{1}{(2C-y)^2}\right) + \kappa_g\right]\phi(y)$$

This expression is a function of the Capillary number Ca and the wall confinement $$C = \frac{H}{a}$$

It accounts for migration due to both flow curvature ($k_g$) and walls ($k_w$). The unknown coefficient depends on the complex interplay between material properties of red blood cells and the local flow conditions and requires computer simulations to determine. It is therefore beyond the scope of this study.

The shear-induced diffusional flux $J_{diffusion}$ is proportional to the product of the number densities of two particles multiplied by the y velocity difference between them and is an integral over all possible spatial configurations[4]. According to previous work[2], this flux can be simplified to the following expression:

$$J_{diffusion} = -\kappa_o\left\{\frac{\partial}{\partial y}\left[\phi(y)\left(1 - \frac{y}{C}\right)\right] + \frac{1}{2C}\phi(y)\right\}\phi(y) -$$

$$\kappa_d\frac{\partial}{\partial y}\left[\phi(y)\phi(y)\left(1 - \frac{y}{C}\right)\right] - \frac{\kappa_c'}{2C}\phi(y)\frac{\partial\phi(y)}{\partial y} - \frac{\kappa_d'}{2C}\frac{\partial}{\partial y}[\phi(y)\phi(y)]$$

Again all unknown coefficients in this expression can only be determined from computer simulations and are beyond the scope of this study. We assume the adsorption of Erythrocyte$_{plex}$ to channel walls is a reversible process occurring within a distance/from the walls:

$$R_{adsorption} = K_1\phi(y) - K_{-1}\phi_s$$

for y<1 or y>2C−1

0 otherwise

The surface concentration of red blood cells is therefore:

$$\phi_s(t) = \int_0^l R_{adsorption}dy$$

for both y=0 and y=2C under the assumption of symmetry about y=C. $K_1$ and $K_{-1}$ are unknown coefficients based on the properties of Erythrocyte$_{plex}$.

Using a finite volume scheme, we solved for the steady state concentration distribution of red blood cells φ(y) under various scenarios. To match the experimental conditions, we set Ca=3, C=22.3 and 1=0.5 for all cases. We set $K_1$ and $K_{-1}$ to zero for control cases of native erythrocytes. In FIG. 3i, we set $K_1$=0.16, $K_w$=0.068, $K_g$=0.0046, $K_e$=$K_c'$=0.088, $K_d$=$K_d'$=0.31. For the control case, we observed the formation of the cell-free layer near top and bottom walls and a peak concentration at the centerline y=C. This prediction matches well with our experimental observation as well as previous studies under varying scenarios of C and $C_a^2$. By changing the values of the unknown coefficients, we can adjust the relative strength of the shear-induced diffusion to deformability-induced lift and thus observed a change of cell-free layer thickness as shown in FIG. 18A and FIG. 18B. With the addition of wall adsorption ($K_1$=100, $K_{-1}$=1) we observed in FIG. 3I a significant change of the concentration distribution profile. The cell-free layer thickness is significantly reduced and so is the peak concentration at the centerline. We set the rates of adsorption to different values (FIGS. 18C and 18D) and observed varying concentration profiles dependent on the strength of adhesion relative to the hydrodynamic effects (diffusion and lift)

Chemotaxis of Anti-PD-L1/Macrophage$_{plex}$

Culture of Tumor Spheroid

4T1 mammary carcinoma cell line was obtained from ATCC (VA, USA), 4T1 cells were cultured in a humidified incubator maintained at 37° C. and 5% $CO_2$. They were cultured in RPMI-1640 media supplemented with 10% FBS and 1% Pen-Strep. To generate 4T1 tumor spheroids, 1000 cells were seeded into Corning® spheroid microplates at a density of 10000 cells/mL and were cultured for 6 days. The medium was refreshed every two days.

Chemotaxis of PD-L1/Macrophage$_{plex}$

PD-L1/Macrophage$_{plex}$ was prepared according to a protocol as described before. PD-L1/Macrophage$_{plex}$ was resuspended in complete DMEM medium at a density of 10000 cells/mL. Tumor spheroid was cultured as described in the previous section. ~1000 PD-L1/Macrophage$_{plex}$ were added into the wells containing 4T1 tumor spheroids. 24 hours after co-culture, the cell nucleus was labeled by Hoechst 33342. The medium was discarded and tumor spheroids were washed three times using cold PBS. The tumor spheroids were then fixed using 4% paraformaldehyde. Tumor spheroids were transferred onto a glass slide and imaged using a Zeiss LSM 710 confocal microscope (Germany).

Statistical Analysis

All experiments were repeated at least three times. All statistical analyses were carried out using Origin 8.0 software. All data are presented as mean±SE (standard error), student's t test, one-way ANOVA with Tukey's HSD analysis, or Mann-Whitney test were used to determine significance. p values represent levels of significance (p<0.001***). All the flow cytometry analyses were carried out using FlowJo 10 software.

REFERENCE

1 Qi, Q. M. et al. In Vitro Measurement and Modeling of Platelet Adhesion on VWF-Coated Surfaces in Channel Flow. *Biophys.* 1 116, 1136-1151 (2019).

2 Rivera, R. G. H., Zhang, X. & Graham, M. D. Mechanistic theory of margination and flow-induced segregation in confined multicomponent suspensions: simple shear and Poiseuille flows. *Physical Review Fluids* 1, 060501 (2016).

3 Qi, Q. M. & Shaqfeh, E. S. Theory to predict particle migration and margination in the pressure-driven channel flow of blood. *Phys. Rev. Fluids* 2, 093102 (2017).

4 Leighton, D. & Acrivos, A. The shear-induced migration of particles in concentrated suspensions. *Journal of Fluid Mechanics* 181, 415-439 (1987).

5 Zhao, H., Spann, A. P. & Shaqfeh, E. S. The dynamics of a vesicle in a wall-bound shear flow. *Physics of Fluids* 23, 121901 (2011).

Example 3

The methods described herein differ from prior technologies at least in part because the assembly occurs on the surface of mammalian cells. The difficulty of surface modification of mammalian cells compared to synthetic surfaces is clear. A very large number of methods have been developed to modify synthetic surfaces including performing chemical reactions, chemical vapor deposition, self-assembled monolayers, layer by layer assembly etc. Yet, translation of these technologies to mammalian cells is severely restricted. Three factors limit the translation. First, the cargo itself can be denatured during the process. Delicate cargoes such as proteins cannot tolerate many surface modification methods. Second, the nature of the surfaces is very different. The surface of mammalian cells is very different from synthetic surfaces, and often not amenable to modification. More importantly, the surface of mammalian cells is dynamic. The attached cargo can be internalized by the cells. If that happens, the cargo ends up inside the cell and loses its functionality. Third, the cell itself can lose its biological activity. Since preservation of surface properties is essential to maintaining cellular function (viability, migration etc.). one cannot indiscriminately coat cellular surfaces. As demonstrated herein, Cellwrap overcomes these factors.

Example 4

AAV9 was attached to RBCs via the polyphenol-mediated approach described herein. This loading provided efficient binding of the AAV9 to the RBCs (FIGS. 25A-25D). When these AAV9-loaded RBCs were injected into mice, gene expression was increased specifically in the lung. Induction of gene expression in other organs was comparable to that induced by free AAV (FIGS. 26A-26F). Additionally, RBC-AAV enabled AAV re-dosing and targeted gene expression in the lung in the presence of existing immune responses (FIG. 27A-27E).

What is claimed herein is:

1. A mammalian hematopoietic cell comprising at least one nanocomplex comprising:
   a) one or more polyphenol molecules; and
   b) one or more biomolecules or one or more active agents: wherein the at least one nanocomplex is adhered to the surface of the mammalian hematopoietic cell.

2. The cell of claim 1, wherein the mammalian hematopoietic cell is an erythrocyte, T cell, monocyte, macrophage, neutrophil or natural killer cell.

3. The cell of claim 1, wherein the at least one nanocomplex collectively comprises 10 to 1 trillion biomolecules or active agents.

4. A method comprising:
   a) combining i) one or more polyphenol molecules and ii) one or more biomolecules or one or more active agents; and
   b) contacting a mammalian hematopoietic cell with the combination resulting from step a; whereby a nanocomplex forms and adheres to the surface of the mammalian hematopoietic cell.

5. A method of administering a biomolecule and/or active agent to a patient in need of treatment with the biomolecule and/or active agent, the method comprising administering a mammalian hematopoietic cell of claim 1 to the patient.

6. The method of claim 5, wherein the mammalian hematopoietic cell is autologous to the patient.

7. The mammalian hematopoietic cell of claim 1, wherein the one or more polyphenols collectively comprise at least one galloyl moiety and/or at least one catechol moiety.

8. The mammalian hematopoietic cell of claim 1, wherein the polyphenol is tannic acid.

9. The mammalian hematopoietic cell of claim 1, wherein the stoichiometric ratio of polyphenol molecules to biomolecules is 570 or less relative polyphenol.

10. The mammalian hematopoietic cell of claim 1, wherein the at least one biomolecule or at least one active agent is a nucleic acid, protein, a viral particle, a viral vector, alkaloid, polysaccharide, anthocyanin, lipid, antiviral drug, antibiotic, chemotherapeutic, or combination thereof.

11. The mammalian hematopoietic cell of claim 1, wherein at least one biomolecule or at least one active agent is an antibody specific for an immune checkpoint protein.

12. The mammalian hematopoietic cell of claim 1, wherein at least one biomolecule or at least one active agent is a viral particle or viral vector.

13. The mammalian hematopoietic cell of claim 12, wherein the viral particle or viral vector is an adeno-associated virus vector.

14. The mammalian hematopoietic cell of claim 13, wherein the adeno-associated virus vector is AAV9.

* * * * *